US009957282B2

(12) United States Patent
Ryckman et al.

(10) Patent No.: US 9,957,282 B2
(45) Date of Patent: May 1, 2018

(54) CRYSTALLINE FORMS OF QUINOLONE ANALOGS AND THEIR SALTS

(71) Applicant: Senhwa Biosciences, Inc., New Taipei (TW)

(72) Inventors: David M. Ryckman, San Diego, CA (US); Iching Grace Yu, San Diego, CA (US); Hshiou-ting Liu, Milpitas, CA (US)

(73) Assignee: SENHWA BIOSCIENCES, INC., New Taipei (TW)

( * ) Notice: Subject to any disclaimer, the term of this patent is extended or adjusted under 35 U.S.C. 154(b) by 0 days. days.

(21) Appl. No.: 14/967,574

(22) Filed: Dec. 14, 2015

(65) Prior Publication Data

US 2017/0166590 A1 Jun. 15, 2017

(51) Int. Cl.
C07D 513/14 (2006.01)
A61K 31/551 (2006.01)
A61K 45/06 (2006.01)

(52) U.S. Cl.
CPC .......... *C07D 513/14* (2013.01); *A61K 31/551* (2013.01); *A61K 45/06* (2013.01); *C07B 2200/13* (2013.01)

(58) Field of Classification Search
CPC ..... C07D 513/14; A61K 45/06; A61K 31/551
IPC .................. C07D 513/14; A61K 45/06,31/551
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,703,055 A | 12/1997 | Felgner et al. | |
| 7,179,805 B2 | 2/2007 | Grant, III et al. | |
| 7,928,100 B2 * | 4/2011 | Nagasawa | C07D 471/14 514/218 |
| 8,853,234 B2 | 10/2014 | Nagasawa et al. | |
| 2007/0099951 A1 | 5/2007 | Dube et al. | |
| 2009/0093455 A1 | 4/2009 | Nagasawa et al. | |
| 2010/0305136 A1 | 12/2010 | Nagasawa | |
| 2011/0218184 A1 | 9/2011 | Nagasawa et al. | |

FOREIGN PATENT DOCUMENTS

| | | |
|---|---|---|
| WO | WO 2000/059882 | 10/2000 |
| WO | WO 2003/050107 A1 | 6/2003 |
| WO | WO 2004/014893 A2 | 2/2004 |
| WO | WO 2006/034113 A2 | 3/2006 |
| WO | WO 2007/019295 | 2/2007 |
| WO | WO 2007/022474 A2 | 2/2007 |
| WO | WO 2007/056113 A2 | 5/2007 |
| WO | WO 2007/146813 | 12/2007 |
| WO | WO 2007/146831 A2 | 12/2007 |
| WO | WO 2008/060693 A2 | 5/2008 |
| WO | WO 2008/092681 A | 8/2008 |
| WO | WO 2008/131134 A1 | 10/2008 |
| WO | WO 2009/046383 | 4/2009 |

OTHER PUBLICATIONS

Braga et al. Struct Bond (2009)132: 25-50.*
International Search Report and Written Opinion for International Application No. PCT/US2008/078859, dated Dec. 24, 2008, 8 pages.
Supplementary European Search Report for European Patent Application No. 08731934.9, dated Jul. 22, 2009, 10 pages.
Supplementary European Search Report and Search Opinion for European Patent Application No. 08835342.0, dated Oct. 12, 2010, 6 pages.
Ansell, R.J. et al., "Molecularly imprinted polymers for bioanalysis: chromatography, binding assays and biomimetic sensors," Curr Opin Biotechnol 1996, 7:89-94.
Berge, S.M. et al., "Pharmaceutical Salts," J Pharm Sci 1977, 66:1-19.
Gibson, U.E.M. et al., "A Novel Method for Real Time Quantitative RT-PCR," Genome Res 1996, 6:995-1001.
Heid, C.A. et al., "Real Time Quantitative PCR," Genome Res 1996, 6:986-994.
Jin, C.H. et al., "Human Vitamin D Receptor-Dependent Transactivation in *Saccharomyces cerevisiae* Requires Retinoid X Receptor," Mol Endocrinol 1996, 10:196-205.
Kriz, D. et al., "Introducing Biomimetic Sensors Based on Molecularly Imprinted Polymers as Recognition Elements," Analytical Chemistry 1995, 67:2142-2144.
Mei, H. et al., "Rapid In Vivo Oral Screening in Rats: Reliability, Acceptance Criteria, and Filtering Efficiency," The AAPS Journal 2006, 8(3) Article 58:E493-E500.
Shea, K.J., "Molecular Imprinting of synthetic Network Polymers: The De Novo Synthesis of Macromolecular Binding and Catalytic Sites," Trends in Polymer Sci 1994, 2(5):166-173.
Vaickus, L. et al., "Immune markers in hematologic malignancies," Crit Rev in Oncol/Hematol 1991, 11:267-297.
Vlatakis, G. et al., "Drug assay using antibody mimics made by molecular imprinting," Nature 1993, 361:645-647.

* cited by examiner

*Primary Examiner* — Shirley V Gembeh
(74) *Attorney, Agent, or Firm* — Cooley LLP

(57) ABSTRACT

The present invention includes crystalline forms of 2-(4-Methyl-[1,4]diazepan-1-yl)-5-oxo-5H-7-thia-1,11b-diaza-benzo[c]fluorene-6-carboxylic acid (5-methyl-pyrazin-2-yl-methyl)-amide and crystalline forms of salts and/or solvates of 2-(4-Methyl-[1,4]diazepan-1-yl)-5-oxo-5H-7-thia-1,11b-diaza-benzo[c]fluorene-6-carboxylic acid (5-methyl-pyrazin-2-ylmethyl)-amide. Furthermore, the present invention provides compositions comprising the crystalline forms and therapeutic use of the crystalline forms and the compositions thereof.

81 Claims, 49 Drawing Sheets

CRYSTALLINE FORMS OF QUINOLONE ANALOGS AND THEIR SALTS

FIELD OF THE DISCLOSURE

The present invention relates to crystalline forms of tetracyclic quinolone compounds or the salts and/or solvates of the tetracyclic quinolone compounds, pharmaceutical composition containing them, and methods of using them.

BACKGROUND OF THE DISCLOSURE

A variety of tetracyclic quinolone compounds have been suggested to function by interacting with quadruplex-forming regions of nucleic acids and modulating ribosomal RNA transcription. See, for example, U.S. Pat. Nos. 7,928,100 and 8,853,234. Specifically, the tetracyclic quinolone compounds can stabilize the DNA G-quadruplexes (G4s) in cancer cells and thereby induce synthetic lethality in cancer cells. Since treatment of cells with G4-stabilizing agents can lead to the formation of DNA double strand breaks (DSBs), DSB formation induced by G4-stabilizing ligand/agent (such as the tetracyclic quinolones) treatment would be more pronounced in cells genetically deficient in, or chemically inhibited in, repair pathways including both non-homologous end joining (NHEJ) and homologous recombination repair (HRR). Furthermore, the tetracyclic quinolone compounds selectively inhibit rRNA synthesis by Pol I in the nucleolus, but do not inhibit mRNA synthesis by RNA Polymerase II (Pol II) and do not inhibit DNA replication or protein synthesis. It is suggested that targeting RNA polymerase I (Pol I) to activate p53 through the nucleolar stress pathway may results in selective activation of p53 in tumor cells. The p53 protein normally functions as a tumor suppressor by causing cancer cells to self-destruct. Activating p53 to kill cancer cells is a well validated anticancer strategy and many approaches are being employed to exploit this pathway. Selective activation of p53 in tumor cells would be an attractive method of treating, controlling, ameliorating tumor cells while not affecting normal healthy cells. The aforementioned tetracyclic quinolones are disclosed in U.S. Pat. Nos. 7,928,100 and 8,853,234, and the contents of this publication are herein incorporated by reference in their entirety for all intended purposes.

Those skilled in the pharmaceutical arts understand that crystallization of an active pharmaceutical ingredient offers the best method for controlling important physiochemical qualities, such as stability, solubility, bioavailability, particle size, bulk density, flow properties, polymorphic content, and other properties. Thus, there is a need for crystalline forms of the tetracyclic quinolones and processes to produce such forms. These crystalline forms should be suitable for pharmaceutical use.

SUMMARY OF THE DISCLOSURE

In one embodiment, the present invention provides a crystalline form of a tetracyclic quinolone compound or a pharmaceutically acceptable salt, ester, and/or solvate thereof. In one embodiment, a crystalline form of a tetracyclic quinolone compound is Compound I:

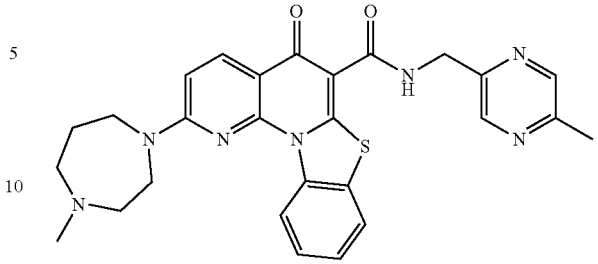

Compound I or a pharmaceutically acceptable salt, ester, and/or solvate thereof. In one embodiment, the crystalline form of Compound I is a free base of Compound I. In another embodiment, the crystalline form of Compound I is a salt or solvate of Compound I. In one embodiment, the crystalline from of Compound I is an acid salt of Compound I.

In some embodiment, the crystalline form of Compound I exhibits an X-ray powder diffraction (XRPD) pattern comprising peaks at about 7.730±0.3, 22.050±0.3, and 24.550±0.3 degrees two-theta. In a further embodiment, the crystalline form of Compound I further exhibits XRPD peaks at about 9.410±0.3 and 27.700±0.3 degrees two-theta. In another embodiment, the crystalline form of Compound I further exhibits XRPD peaks at about 17.950±0.3 and 25.400±0.3 degrees two-theta. In one embodiment, the crystalline form of Compound I further exhibits at least one XRPD peaks at about 11.230±0.3, 11.630±0.3, 16.900±0.3, 18.580±0.3, 23.300±0.3, and 26.700±0.3 degrees two-theta. In one embodiment, the crystalline form of Compound I exhibits an XRPD pattern comprising three or more peaks selected from the group consisting of 7.730±0.3, 9.410±0.3, 11.230±0.3, 11.630±0.3, 16.900±0.3, 17.950±0.3, 18.580±0.3, 22.050±0.3, 23.300±0.3, 24.550±0.3, 25.400±0.3, 26.700±0.3 and 27.700±0.3 degrees two-theta. In another embodiment, the crystalline form of Compound I exhibits XRPD pattern substantially similar to FIG. 1. In one embodiment, the crystalline form of Compound I exhibits a Differential Scanning calorimetry (DSC) thermogram having a peak characteristic value at about 215.41±2.0° C.

In one embodiment, the crystalline form of Compound I is polymorph A. In some embodiments, the crystalline form of Compound I and/or crystalline form of polymorph A of Compound I has a purity of about 95%, about 97%, about 99% or about 99.5% or higher.

In another embodiment, the crystalline form of Compound I exhibits an XRPD pattern comprising peaks at about 5.720±0.3 degrees two-theta. In another embodiment, the crystalline form of Compound I exhibits XRPD pattern substantially similar to FIG. 7. In one embodiment, the crystalline form of Compound I exhibits a DSC thermogram having a peak characteristic value at about 246.47±2.0° C.

In one embodiment, the crystalline form of Compound I is polymorph C. In some embodiments, the crystalline form of Compound I and/or crystalline form of polymorph C of Compound I has a purity of about 95%, about 97%, about 99% or about 99.5% or higher.

In some embodiments, the crystalline form of Compound I exhibits an XRPD pattern comprising peaks at about 5.680±0.2 degrees two-theta. In one embodiment, the crystalline form of Compound I further exhibits XRPD peaks at about 12.200±0.2, 12.600±0.3, 5.360±0.3 and 27.560±0.3 degrees two-theta. In one embodiment, the crystalline form of Compound I exhibits an XRPD pattern comprising two or more peaks selected from the group consisting of 5.680±0.2, 12.200±0.2, 12.600±0.3, 25.360±0.3 and 27.560±0.3. In another embodiment, the crystalline form of Compound I exhibits XRPD pattern substantially similar to FIG. 11. In one embodiment, the crystalline form of Compound I exhibits a DSC thermogram having a peak characteristic value at about 231.99±2.0° C.

In one embodiment, the crystalline form of Compound I is polymorph E. In some embodiments, the crystalline form of Compound I and/or crystalline form of polymorph E of Compound I has a purity of about 95%, about 97%, about 99% or about 99.5% or higher.

In one embodiment, the crystalline form of Compound I exhibits an XRPD pattern comprising peaks at about 5.000±0.3 and 6.060±0.4 degrees two-theta. In another embodiment, the crystalline form of Compound I exhibits XRPD pattern substantially similar to FIG. 16. In another embodiment, the crystalline form of Compound I exhibits a DSC thermogram having a peak characteristic value at about 222.11±2.0° C.

In one embodiment, the crystalline form of Compound I is polymorph G. In some embodiments, the crystalline form of Compound I and/or crystalline form of polymorph G of Compound I has a purity of about 95%, about 97%, about 99% or about 99.5% or higher.

In one embodiment, the crystalline form of Compound I exhibits greater than about 90%, 95%, 97%, 98%, 99%, or 95% purity of Compound I.

In one embodiment, the crystalline form of Compound I is an acid salt of Compound I which is selected from the group consisting of: hydrochloric acid salt, maleic acid salt, fumaric acid salt, citric acid salt, malic acid salt, acetic acid salt, sulfuric acid salt, phosphoric acid salt, L-(±)-tartaric acid salt, D-glucuronic acid salt, benzoic acid salt, succinic acid salt, ethane sulfonic acid salt, methane sulfonic acid salt, p-toluene sulfonic acid salt, malonic acid salt, benzene sulfonic acid salt, and 1-hydroxy-2-naphthoic acid salt. In one embodiment, the crystalline form of a slat of Compound I is selected from the group consisting of hydrochloric acid salt, maleic acid salt, fumaric acid salt, citric acid salt, and L-malic acid salt.

In one embodiment, the crystalline form of Compound I is a solvate of Compound I. In some embodiments, the crystalline form of Compound I is a NMP (N-methyl pyrrolidone) solvate of Compound I.

In one embodiment, the crystalline form of Compound I is a crystalline form of HCl salt of Compound I. In some embodiments, the crystalline form of HCl salt of Compound I exhibits an X-ray powder diffraction pattern (XRDP) comprising peaks at about 4.660±0.3 and 24.540±0.3 degrees two-theta. In one embodiment, the crystalline form of HCl salt of Compound I further exhibits one or more XRPD peaks at about 19.260±0.4, 20.160±0.4, 24.920±0.3, and 26.360±0.5 degrees two-theta. In another embodiment, the crystalline form of HCl salt of Compound I further exhibits one or more XRPD peaks at about 13.980±0.4, 14.540±0.3, 25.380±0.3, and 28.940±0.3 degrees two-theta. In another embodiment, the crystalline form of HCl salt of Compound I exhibits an X-ray powder diffraction pattern substantially similar to FIG. 21. In another embodiment, the crystalline form of HCl salt of Compound I exhibits a Differential Scanning calorimetry (DSC) thermogram having a peak characteristic value at about 266.27±2.0° C.

In one embodiment, the crystalline form of Compound I is a crystalline form of maleic acid salt of Compound I. In some embodiments, the crystalline form of maleic acid salt of Compound I exhibits an X-ray powder diffraction pattern (XRDP) comprising peaks at about 7.400±0.3, 18.440±0.5, and 26.500±0.4 degrees two-theta. In another embodiment, the crystalline form of maleic acid salt of Compound I further exhibits one or more XRPD peaks at about 22.320±0.4, 23.920±0.3, 24.300±0.4, and 25.240±0.7 degrees two-theta. In another embodiment, the crystalline form of maleic acid salt of Compound I further exhibits one or more XRPD peaks at about 5.040±0.3, 15.080±0.3, 15.880±0.4, 20.860±0.4, and 28.540±0.3 degrees two-theta. In another embodiment, the crystalline form of maleic acid salt of Compound I exhibits an X-ray powder diffraction pattern substantially similar to FIG. 26. In another embodiment, the crystalline form of maleic acid salt of Compound I exhibits a Differential Scanning calorimetry (DSC) thermogram having a peak characteristic value at about 217.32±2.0° C.

In one embodiment, the crystalline form of Compound I is a crystalline form of fumaric acid salt of Compound I. In some embodiments, the crystalline form of fumaric acid salt of Compound I exhibits an X-ray powder diffraction pattern (XRDP) comprising peaks at about 6.360±0.3 and 24.800±0.3 degrees two-theta. In another embodiment, the crystalline form of fumaric acid salt of Compound I further exhibits one or more XRPD peaks at about 19.660±0.3, 20.420±0.3, and 26.860±0.3 degrees two-theta. In another embodiment, the crystalline form of fumaric acid salt of Compound I further exhibits one or more XRPD peaks at about 12.680±0.3, 17.020±0.2, 25.180±0.2, and 28.280±0.3 degrees two-theta. In another embodiment, the crystalline form of fumaric acid salt of Compound I exhibits an X-ray powder diffraction pattern substantially similar to FIG. 31. In another embodiment, the crystalline form of fumaric acid salt of Compound I exhibits a Differential Scanning calorimetry (DSC) thermogram having a peak characteristic value at about 222.40±2.0° C.

In one embodiment, the crystalline form of Compound I is a crystalline form of citric acid salt of Compound I. In some embodiments, the crystalline form of citric acid salt of Compound I exhibits an X-ray powder diffraction pattern (XRDP) comprising peaks at about 4.900±0.3, 25.380±0.3, and 27.500±0.4 degrees two-theta. In another embodiment, the crystalline form of citric acid salt of Compound I further exhibits one or more XRPD peaks at about 15.360±0.3, 18.100±0.3, 19.300±0.3, and 26.140±0.4 degrees two-theta. In another embodiment, the crystalline form of citric acid salt of Compound I further exhibits one or more XRPD peaks at about 17.400±0.3, 18.680±0.4, 24.040±0.4, and 26.740±0.3 degrees two-theta. In another embodiment, the crystalline form of citric acid salt of Compound I exhibits an X-ray powder diffraction pattern substantially similar to FIG. 36. In another embodiment, the crystalline form of citric acid salt of Compound I exhibits a Differential Scanning calorimetry (DSC) thermogram having a peak characteristic value at about 196.86±2.0° C.

In one embodiment, the crystalline form of Compound I is a crystalline form of L-malic acid salt of Compound I. In some embodiments, the crystalline form of L-malic acid salt of Compound I exhibits an X-ray powder diffraction pattern (XRDP) comprising peaks at about 6.580±0.2, 6.780±0.3, and 25.560±0.4 degrees two-theta. In another embodiment, the crystalline form of L-malic acid salt of Compound I further exhibits one or more XRPD peaks at about 19.560±0.4, 23.660±0.4, 26.060±0.7, and 26.960±0.7 degrees two-theta. In another embodiment, the crystalline form of L-malic acid salt of Compound I further exhibits one or more XRPD peaks at about 8.800±0.3, 11.800±0.3, 18.600±0.3, 24.460±0.5, and 25.080±0.3 degrees two-theta.

In another embodiment, the crystalline form of L-malic acid salt of Compound I exhibits an X-ray powder diffraction pattern substantially similar to FIG. 41. In another embodiment, the crystalline form of L-malic acid salt of Compound I exhibits a Differential Scanning calorimetry (DSC) thermogram having a peak characteristic value at about 209.67±2.0° C.

In one embodiment, a composition is provided comprising a crystalline form of Compound I, or a pharmaceutically acceptable salt, ester, and/or solvate thereof, as described herein. In another embodiment, a composition is provided comprising a crystalline form of a free base of Compound I. In one embodiment, a composition is provided comprising a crystalline form of a salt or a solvate of Compound I. In one embodiment, a composition is provided comprising a crystalline form of an acid salt of Compound I. In one embodiment, a composition is provided comprising any one or more crystalline forms of Compound I as described herein. In some embodiment, any composition described herein, comprises at least one pharmaceutically acceptable carrier.

In one embodiment, a method of stabilizing G-quadruplexes (G4s) in a subject is provided where said method comprises administering to the subject a therapeutically effective amount of a crystalline form of Compound I, or a pharmaceutically acceptable salt, ester, and/or solvate thereof, as described herein.

In one embodiment, a method of modulating p53 activity in a subject is provided where said method comprises administering to the subject a therapeutically effective amount of a crystalline form of Compound I, or a pharmaceutically acceptable salt, ester, and/or solvate thereof, as described herein.

In one embodiment, a method for treating or ameliorating cell proliferation disorder in a subject is provided where said method comprises administering to a subject in need thereof a therapeutically effective amount of the crystalline form of compound I, or a pharmaceutically acceptable salt, ester, and/or solvate thereof, as described herein. In one embodiment, the method is provided for treating or ameliorating cancer.

In one embodiment, a method for treating or ameliorating cancer is provided where said method comprises administering to a subject in need thereof a therapeutically effective amount the crystalline form of compound I, or a pharmaceutically acceptable salt, ester, and/or solvate thereof, as described herein, wherein said cancer is selected from the group consisting of: heme cancer, colorectum cancer, breast cancer, lung cancer, liver cancer, ovarian cancer, cervical cancer, Ewing's sarcoma, pancreatic cancer, cancer of the lymph nodes, colon cancer, prostate cancer, brain cancer, cancer of the head and neck, skin cancer, kidney cancer, and cancer of the heart. In one embodiment, cancer treated or ameliorated by the said method is heme cancer which is selected from the group consisting of: leukemia, lymphoma, myeloma, and multiple myeloma. In one embodiment, cancer treated or ameliorated by the said method is homologous recombination (HR) dependent double strand break (DSB) repair deficient cancer or non-homologous end joining (NHEJ) DSB repair deficient cancer. In another embodiment, cancer treated or ameliorated by the said method comprises cancer cells harboring defects in breast cancer 1 (BRCA1), breast cancer 2 (BRCA2), and/or other members of the homologous recombination pathway. In another embodiment, the cancer cells are deficient in BRCA1 and/or BRCA2. In another embodiment, the cancer cells are homozygous for a mutation in BRCA1 and/or BRCA2. In another embodiment, the cancer cells are heterozygous for a mutation in BRCA1 and/or BRCA2.

In one embodiment, the methods provided herein further comprise administering one or more additional therapeutic agents. In some embodiments, said one or more additional therapeutic agent is an anticancer agent or immunotherapeutic agent. In one embodiment, the one or more therapeutically active agent is an immunotherapeutic agent. In some embodiments, one or more immunotherapeutic agents includes, but is not limited to, a monoclonal antibody, an immune effector cell, adoptive cell transfer, an immunotoxin, a vaccine, or a cytokine.

In one embodiment, a method for reducing or inhibiting cell proliferation is provided where said method comprises contacting cells with a therapeutically effective amount of Compound I, or a pharmaceutically acceptable salt, ester, and/or solvate thereof. In one embodiment, said cells are in a cancer cell line or in a cancer in a subject. In one embodiment, said cancer cell in the above described method is selected from the group consisting of: heme cancer, colorectum cancer, breast cancer, lung cancer, liver cancer, ovarian cancer, cervical cancer, Ewing's sarcoma, pancreatic cancer, cancer of the lymph nodes, colon cancer, prostate cancer, brain cancer, cancer of the head and neck, skin cancer, kidney cancer, and cancer of the heart. In some embodiment, said heme cancer cell in above described method is selected from the group consisting of: leukemia, lymphoma, myeloma, and multiple myeloma. In one embodiment, the cancer cell in the above described method is the cancer cells harboring defects in homologous recombination (HR) dependent double strand break (DSB) repair or non-homologous end joining (NHEJ) DSB repair. In one embodiment, the cancer cells are cancer cells harboring defects in breast cancer 1 (BRCA1), breast cancer 2 (BRCA2), and/or other members of the homologous recombination pathway. In another embodiment, the cancer cells are deficient in BRCA1 and/or BRCA2. In another embodiment, the cancer cells are homozygous for a mutation in BRCA1 and/or BRCA2. In another embodiment, the cancer cells are heterozygous for a mutation in BRCA1 and/or BRCA2.

DETAILED DESCRIPTIONS OF THE DISCLOSURE

Figure 1:
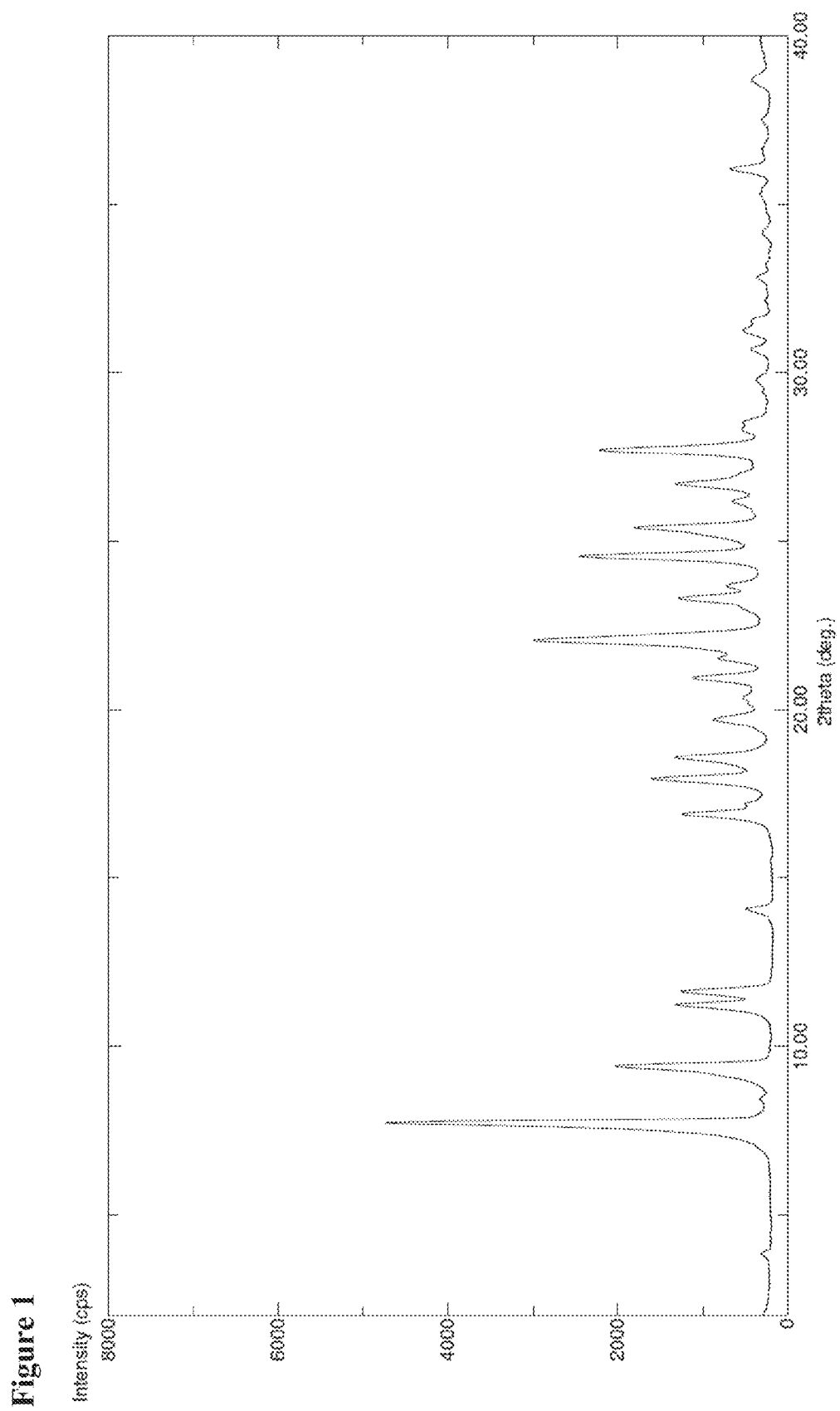
FIG. 1 is a graph of an x-ray powder diffraction (XRPD) of polymorph A of Compound I (free base).

The present invention relates to crystalline forms of tetracyclic quinolone compounds, which stabilize G-quadruplexes (G4s) and/or inhibit Pol I, as well as crystalline forms of the salts and/or solvates of the tetracyclic quinolone compounds. These crystalline materials can be formulated into pharmaceutical compositions and used for treating disorders characterized by proliferation of cells.

Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±15% or ±10%, in another example ±5%, in another example ±1%, and in yet another example±0.1% from the specified amount, as such variations are appropriate to perform the disclosed method.

The term "compound(s) of the present invention" or "present compound(s)" refers to the crystalline form of 2-(4-Methyl-[1,4]diazepan-1-yl)-5-oxo-5H-7-thia-1,11b-diaza-benzo[c]fluorene-6-carboxylic acid (5-methyl-pyrazin-2-ylmethyl)-amide (Compound I) or isomers, salts, esters, N-oxides, or solvates thereof. Alternatively the above terms may refer to salt or solvate or both form of Compound I. The crystalline forms of Compound I described throughout the application including a crystalline form of any single isomer of Compound I, a mixture of any number of isomers of Compound I.

Compound I

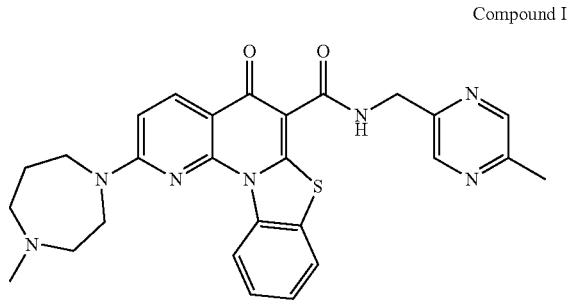 [SMILES: Cc1cnc(CNC(=O)c2c(=O)c3ccc(N4CCCN(C)CC4)nc3n3c2sc2ccccc23)cn1]

The term "co-administration" or "coadministration" refers to administration of (a) a crystalline form of Compound I, or a crystalline form of pharmaceutically acceptable salt, ester, solvate and/or prodrug of Compound I; and (b) one or more additional therapeutic agent and/or radio therapy, in combination, i.e., together in a coordinated fashion.

The term "isomer" refers to compounds having the same chemical formula but may have different stereochemical formula, structural formula, or special arrangements of atoms. Examples of isomers include stereoisomers, diastereomers, enantiomers, conformational isomers, rotamers, geometric isomers, and atropisomers.

"N-oxide", also known as amine oxide or amine-N-oxide, means a compound that derives from a compound of the present invention via oxidation of an amine group of the compound of the present invention. An N-oxide typically contains the functional group $R_3N^{\pm}$—$O^-$ (sometimes written as $R_3N=O$ or $R_3N \rightarrow O$).

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

The term "composition" denotes one or more substance in a physical form, such as solid, liquid, gas, or a mixture thereof. One example of composition is a pharmaceutical composition, i.e., a composition related to, prepared for, or used in medical treatment.

The term "carboxylic acid" refers to an organic acid characterized by one or more carboxyl groups, such as acetic acid and oxalic acid. "Sulfonic acid" refers to an organic acid with the general formula of R—$(S(O)_2$—$OH)_n$, wherein R is an organic moiety and n is an integer above zero, such as 1, 2, and 3. The term "polyhydroxy acid" refers to a carboxylic acid containing two or more hydroxyl groups. Examples of polyhydroxy acid include, but are not limited to, lactobionic acid, gluconic acid, and galactose.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The term "substantially similar" as used herein means an analytical spectrum, such as XRPD patterns, Raman spectroscopy, and etc., which resembles the reference spectrum to a great degree in both the peak locations and their intensity.

The terms "excipient", "carrier", and "vehicle" are used interchangeably throughout this application and denote a substance with which a compound of the present invention is administered.

"Therapeutically effective amount" means the amount of a crystalline form that, when administered to a patient for treating a disease or other undesirable medical condition, is sufficient to have a beneficial effect with respect to that disease or condition. The therapeutically effective amount will vary depending on the crystalline form, the disease or condition and its severity, and the age, weight, etc. of the patient to be treated. Determining the therapeutically effective amount of a given crystalline form is within the ordinary skill of the art and requires no more than routine experimentation.

As used herein, the phrase "a disorder characterized by cell proliferation" or "a condition characterized by cell proliferation" include, but are not limited to, cancer, benign and malignant tumors. Examples of cancer and tumors include, but are not limited to, cancers or tumor growth of the colorectum, breast, lung, liver, pancreas, lymph node, colon, prostate, brain, head and neck, skin, kidney, blood and heart (e.g., leukemia, lymphoma, and carcinoma).

The terms "treat", "treating" or "treatment" in reference to a particular disease or disorder includes prevention of the disease or disorder, and/or lessening, improving, ameliorating or abrogating the symptoms and/or pathology of the disease or disorder. Generally the terms as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the terms "inhibiting" or "reducing" cell proliferation is meant to slow down, to decrease, or, for example, to stop the amount of cell proliferation, as measured using methods known to those of ordinary skill in the art, by, for example, 10%, 20%, 30%, 40%, 50%, 60%, 70%, 80%, 90%, 95%, or 100%, when compared to proliferating cells that are not subjected to the methods and compositions of the present application.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Crystalline Materials

In one embodiment, the present invention provides a crystalline form of Compound I (free base). In another embodiment, the present invention provides a crystalline form of a salt and/or solvate of Compound I. In one embodiment, the salt is a hydrochloric acid addition salt. In one embodiment, the salt is a sulfuric acid addition salt. In one embodiment, the salt is a sulfonic acid addition salt. In one embodiment, the salt is a carboxylic acid addition salt. In one embodiment, the salt is a polyhydroxy acid addition salt.

Examples of the crystalline salt include, but are not limited to, hydrochloric acid salt, maleic acid salt, fumaric acid salt, citric acid salt, malic acid salt, sulfuric acid salt, acetic acid salt, phosphoric acid salt, L-(+)-tartaric acid salt, D-glucuronic acid salt, benzoic acid salt, succinic acid salt, ethane sulfonic acid salt, methane sulfonic acid salt, p-toluene sulfonic acid salt, malonic acid salt, benzene sulfonic acid salt, and 1-hydroxy-2-naphthoic acid salt. In one embodiment, the ratio of the Compound I to acid in the crystalline salt is about 1:0.5 to about 1:3.

An example of crystalline solvate includes, but not limited to NMP (N-methyl-2-pyrrolidone) solvate of Compound I.

In one embodiment, the crystalline forms are characterized by the interlattice plane intervals determined by an X-ray powder diffraction pattern (XRDP). The spectrum of XRDP is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRDP can be selected according to the peak locations and their relative intensity to conveniently distinguish this crystalline structure from others. The % intensity of the peaks relative to the most intense peak may be represented as I/Io.

Those skilled in the art recognize that the measurements of the XRDP peak locations and/or intensity for a given crystalline form of the same compound will vary within a margin of error. The values of degree 2θ allow appropriate error margins. Typically, the error margins are represented by "±". For example, the degree 2θ of about "8.716±0.3" denotes a range from about 8.716+0.3, i.e., about 9.016, to about 8.716−0.3, i.e., about 8.416. Depending on the sample preparation techniques, the calibration techniques applied to the instruments, human operational variation, and etc., those skilled in the art recognize that the appropriate error of margins for a XRDP can be about ±0.7; ±0.6; ±0.5; ±0.4; ±0.3; ±0.2; ±0.1; ±0.05; or less.

Additional details of the methods and equipment used for the XRDP analysis are described in the Examples section.

In one embodiment, the crystalline forms are characterized by Differential Scanning calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. A peak characteristic value of a DSC thermogram is often used as the characteristic peak to distinguish this crystalline structure from others.

Those skilled in the art recognize that the measurements of the DSC thermogram for a given crystalline form of the same compound will vary within a margin of error. The values of a single peak characteristic value, expressed in degree C., allow appropriate error margins. Typically, the error margins are represented by "±". For example, the single peak characteristic value of about "53.09±2.0" denotes a range from about 53.09+2, i.e., about 55.09, to about 53.09−2, i.e., about 51.09. Depending on the sample preparation techniques, the calibration techniques applied to the instruments, human operational variations, and etc., those skilled in the art recognize that the appropriate error of margins for a single peak characteristic value can be ±2.5; ±2.0; ±1.5; ±1.0; ±0.5; or less.

Additional details of the methods and equipment used for the DSC thermogram analysis are described in the Examples section.

In one embodiment, the crystalline forms are characterized by Raman spectroscopy. The Raman spectrum is typically represented by a diagram plotting the Raman intensity of the peaks versus the Raman shift of the peaks. The "peaks" of Raman spectroscopy are also known as "absorption bands". The intensities are often given in parenthesis with the following abbreviations: strong=st; medium=m; and weak=w. The characteristic peaks of a given Raman spectrum can be selected according to the peak locations and their relative intensity to conveniently distinguish this crystalline structure from others.

Those skilled in the art recognize that the measurements of the Raman peak shifts and/or intensity for a given crystalline form of the same compound will vary within a margin of error. The values of peak shift, expressed in reciprocal wave numbers ($cm^{-1}$), allow appropriate error margins. Typically, the error margins are represented by "±". For example, the Raman shift of about "1310±10" denotes a range from about 1310+10, i.e., about 1320, to about 1310−10, i.e., about 1300. Depending on the sample preparation techniques, the calibration techniques applied to the instruments, human operational variations, and etc., those skilled in the art recognize that the appropriate error of margins for a Raman shift can be ±12; ±10; ±8; ±5; ±3; ±1; or less.

Additional details of the methods and equipment used for the Raman spectroscopy analysis are described in the Examples section.

In one embodiment, the crystalline form of Compound I (free base). In some embodiments, crystalline form of Compound I (free base) exhibits different polymorphs. Examples of the crystalline form of Compound I (free base) include, but are not limited to, Polymorphs A, C, E, and G, as defined in the following sections.

In some embodiments, one form of polymorph is more stable than the other forms. In one embodiment, crystalline form of polymorph A of compound I (free base) exhibits high stability. In some embodiments, different polymorphs of Compound I (free base) convert to another polymorph forms under certain conditions. In some embodiments, polymorphs C, E, and/or G convert to polymorph A under suitable conditions. In one embodiment, each of polymorphs C, E, and G independently convert to polymorph A in a solution at room temperature or at an elevated temperature. Polymorph A is the most thermodynamically stable form; however, other forms may be formed or favored kinetically under certain conditions.

In one embodiment of the present disclosure, the crystalline form of Compound I may comprise of a mixture of one or more forms of polymorphs of Compound I. In some embodiments, the crystalline form of Compound I may comprise of substantially pure form of one polymorph type.

In one embodiment, the crystalline form of Compound I may comprise of over about 99.9%, about 99.8%, about 99.7%, about 99.6%, about 99.5%, about 99.4%, about 99.3%, about 99.2%, about 99.1%, or about 99.0% of one polymorph of Compound I. In another embodiment, the crystalline form of Compound I may comprise over about 99%, 98%, 97%, 96%, 95%, 94%, 93%, 92%, 91%, or 90% of one polymorph of Compound I. In some embodiments, the crystalline form of Compound I may comprise over about 90%, 85%, 80%, 75%, 70%, 65%, 60%, 55%, 50%, 45%, or 40% of one polymorph of Compound I.

In one embodiment of the present disclosure, the crystalline form of Compound I may comprise of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, or about 85% of polymorph A of Compound I (free base).

In one embodiment of the present disclosure, the crystalline form of Compound I may be polymorph A of Compound I (free base) comprising about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 18%, or 20% of polymorphs C, E, or G, or mixtures thereof.

In one embodiment of the present disclosure, the crystalline form of Compound I may be polymorph C of Compound I (free base) comprising about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 18%, or 20% of polymorph A.

In one embodiment of the present disclosure, the crystalline form of Compound I may be polymorph E of Compound I (free base) comprising about 0.1%, 0.2%, 0.3%, 0.4%, 0.50%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 18%, or 20% of polymorph A.

In one embodiment of the present disclosure, the crystalline form of Compound I may be polymorph G of Compound I (free base) comprising about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 18%, or 20% of polymorph A.

In one embodiment, the present disclosure provides crystalline form of Compound I that is highly pure. In one embodiment of the present disclosure, the purity of the crystalline form of Compound I may be at least 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, or about 90% pure with respect to Compound I.

Additional methods to characterize the present crystalline forms are described in the Example section of this application.

Polymorph A

In one embodiment, Polymorph A of Compound I (free base) exhibits an XRDP comprising peaks at about 7.730, 22.050, and 24.550 degrees two-theta with the margin of error of about ±0.5; about ±0.4; about ±0.3; about ±0.2; about ±0.1; about ±0.05; or less. In another embodiment, the XRDP of the crystalline polymorph A of Compound I (free base) further comprises peaks at about 9.410 and 27.700 degrees two-theta with the margin of error of about ±0.5; about ±0.4; about ±0.3; about ±0.2; about ±0.1; about ±0.05; or less. In further embodiment, the crystalline form of polymorph A of Compound I (free base) further comprises peaks at about 17.950 and 25.400 degrees two-theta with the margin of error of about ±0.5; about ±0.4; about ±0.3; about ±0.2; about ±0.1; about ±0.05; or less. In another embodiment, the crystalline form of polymorph A of Compound I (free base) further comprises at least one peaks at about 11.230, 11.630, 16.900, 18.580, 23.300, and 26.700 degrees two-theta with the margin of error of about ±0.5; about ±0.4; about ±0.3; about ±0.2; about ±0.1; about ±0.05; or less. In yet another embodiment, the crystalline form of polymorph A of Compound I (free base) exhibits an XRDP comprising peaks shown in Table 1 below:

TABLE 1

XRDP Table of Polymorph A of Compound I (free base)

| 2Theta | Flex Width | d-value | Intensity | I/Io |
|---|---|---|---|---|
| 3.830 | ***** | 23.0507 | 312 | 7 |
| 7.730 | 0.200 | 11.4275 | 4749 | 100 |
| 9.410 | 0.224 | 9.3908 | 2036 | 43 |
| 11.230 | 0.200 | 7.8726 | 1322 | 28 |
| 11.630 | 0.224 | 7.6027 | 1254 | 27 |
| 14.060 | 0.224 | 6.2937 | 485 | 11 |
| 16.900 | 0.224 | 5.2419 | 1246 | 27 |
| 17.190 | 0.141 | 5.1541 | 507 | 11 |
| 17.950 | 0.224 | 4.9376 | 1599 | 34 |
| 18.580 | 0.235 | 4.7716 | 1338 | 29 |
| 19.700 | 0.259 | 4.5027 | 875 | 19 |
| 20.210 | 0.129 | 4.3903 | 467 | 10 |
| 20.360 | 0.176 | 4.3582 | 528 | 12 |
| 20.940 | 0.247 | 4.2388 | 1115 | 24 |
| 21.510 | 0.188 | 4.1278 | 816 | 18 |
| 22.050 | 0.247 | 4.0279 | 2994 | 64 |
| 23.300 | 0.235 | 3.8145 | 1285 | 28 |
| 23.690 | 0.224 | 3.7526 | 714 | 16 |
| 24.550 | 0.235 | 3.6231 | 2447 | 52 |
| 25.400 | 0.212 | 3.5037 | 1804 | 38 |
| 26.180 | 0.212 | 3.4011 | 646 | 14 |
| 26.700 | 0.235 | 3.3360 | 1330 | 28 |
| 27.700 | 0.235 | 3.2178 | 2224 | 47 |
| 28.300 | 0.212 | 3.1509 | 531 | 12 |
| 28.540 | 0.200 | 3.1250 | 533 | 12 |
| 30.700 | 0.247 | 2.9099 | 436 | 10 |
| 31.230 | 0.282 | 2.8617 | 518 | 11 |
| 31.560 | 0.176 | 2.8325 | 436 | 10 |
| 36.040 | 0.247 | 2.4900 | 670 | 15 |
| 38.680 | 0.353 | 2.3259 | 422 | 9 |

In one specific embodiment, the crystalline form of polymorph A of Compound I (free base) exhibits an XRDP that is substantially similar to FIG. 1.

Figure 2:
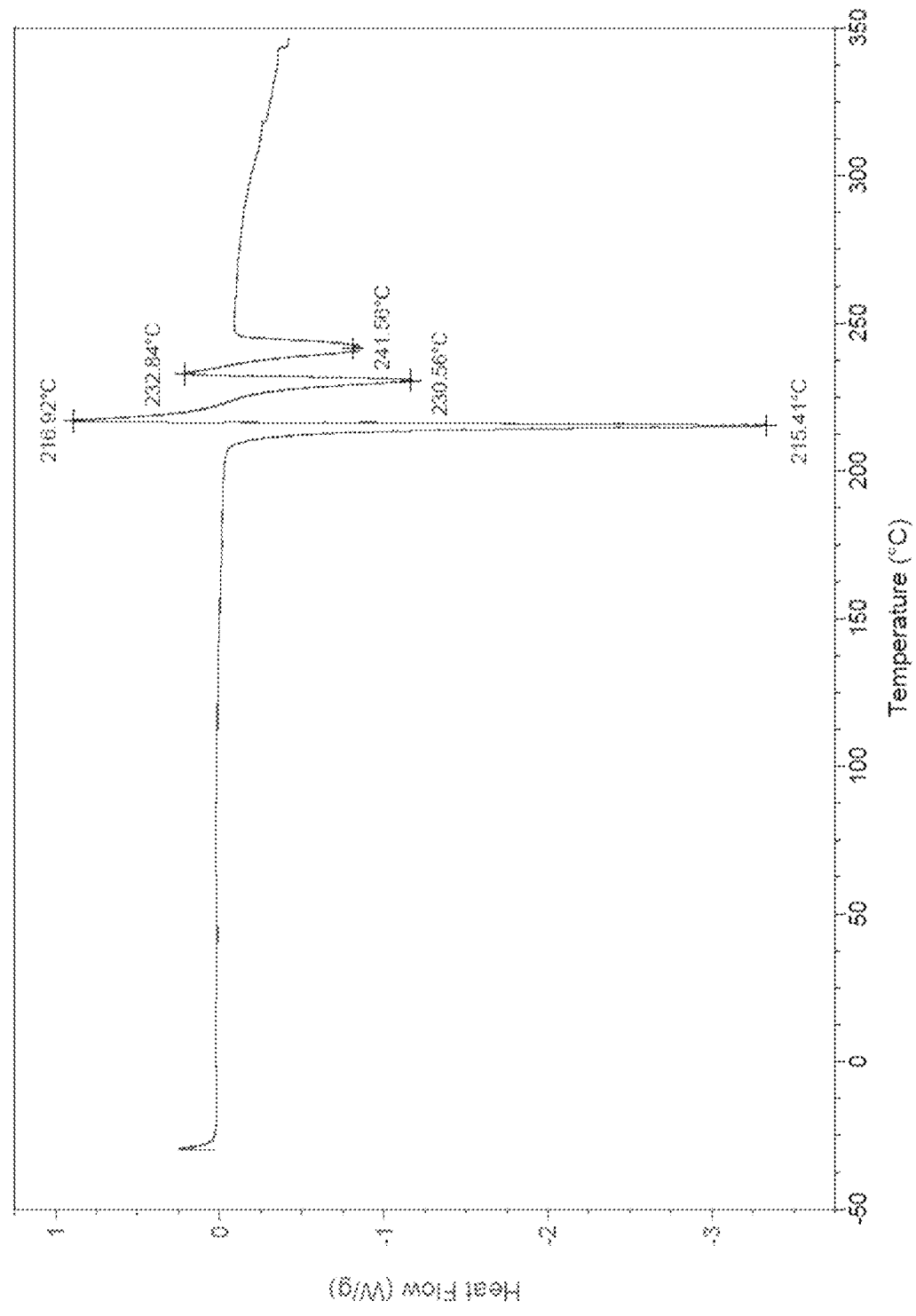
FIG. 2 is a differential scanning calorimetry (DSC) thermogram of polymorph A of Compound I (free base).

In one embodiment, the crystalline form of polymorph A of Compound I (free base) exhibits a DSC thermogram comprising a sharp endotherm at about 215.41° C. with the error of margin of about ±2.5; about ±2.0; about ±1.5; about ±1.0; about ±0.5; or less. In another embodiment, the crystalline form of polymorph A of Compound I (free base) further exhibits a DSC thermogram comprising one or more of the following peaks: exothertn at about 216.92±2.0° C., endotherm at about 230.56±2.0° C., exotherm at about 232.84±2.0° C., and endotherm at about 241.56±2.0° C. In one specific embodiment, the crystalline form of polymorph A of Compound I (free base) exhibits a DSC thermogram that is substantially similar to FIG. 2.

Figure 5:
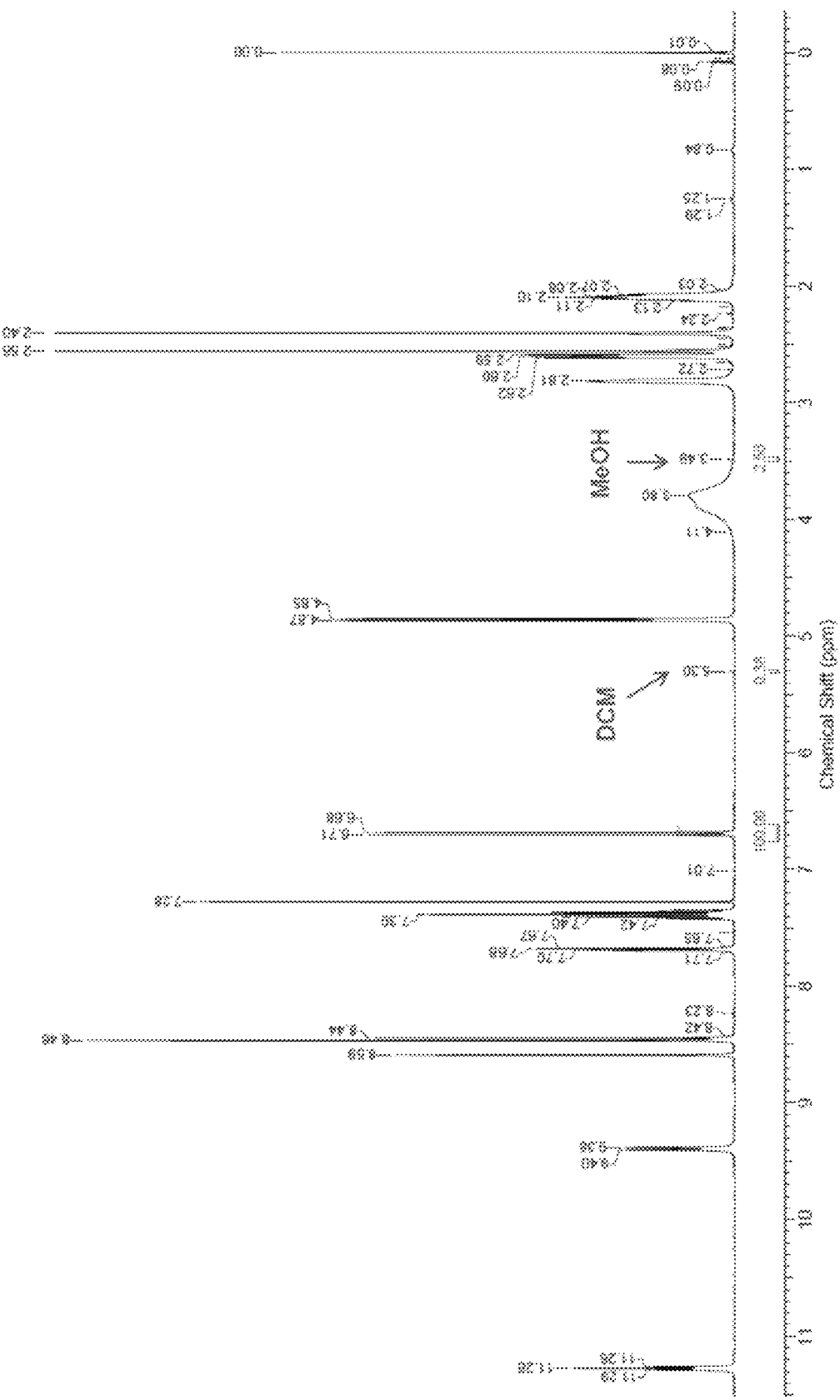
FIG. 5 is a $^1$H NMR spectrum of polymorph A of Compound I (free base).
Figure 6A:
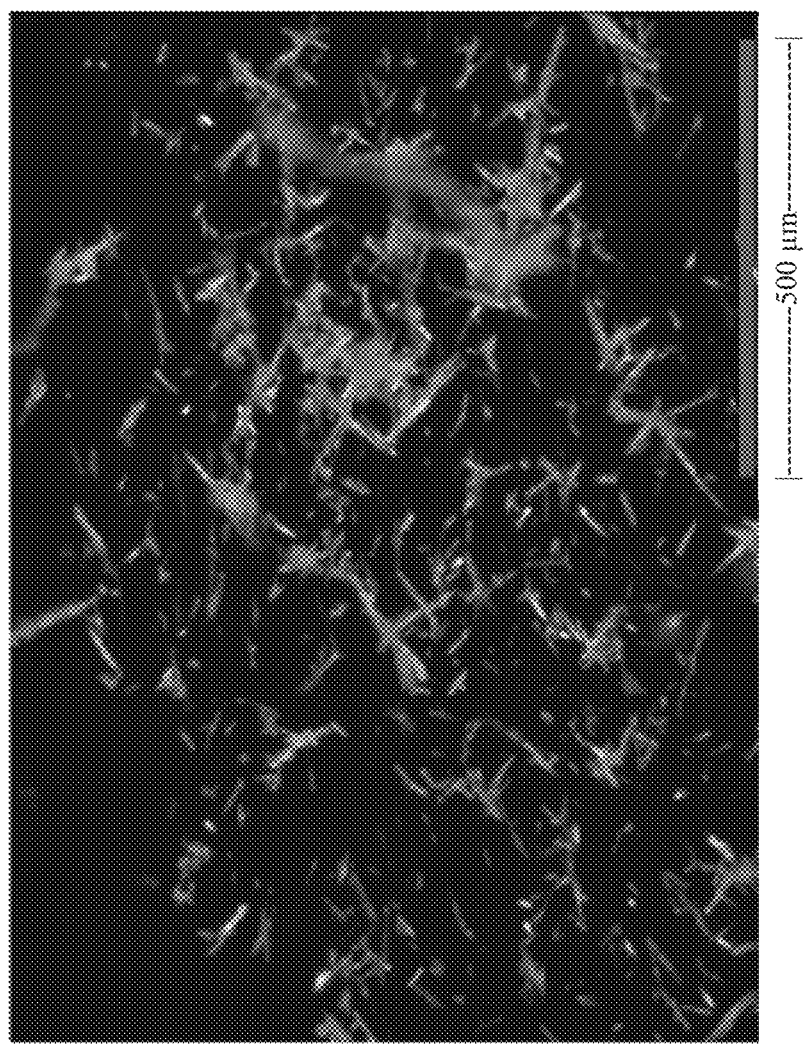
FIG. 6A is a microscopy picture of polymorph A of Compound I (free base) using crossed polarization filters and FIG. 6B is a microscopy picture of polymorph A of Compound I (free base) with no polarization filters.
Figure 6B:

In one embodiment, the crystalline form of polymorph A of Compound I (free base) exhibits a $^1$H NMR spectrum that is substantially similar to FIG. 5 In another embodiment, the crystalline form of polymorph A of Compound I (free base) may have the crystal habit of thin needles that form loosely bound lumps on a macroscopic scale, which are substantially similar to FIGS. 6A and 6B.

Polymorph C

In one embodiment, polymorph C of Compound I (free base) exhibits an XRDP comprising peaks at about 5.720 degrees two-theta with the margin of error of about ±0.5, about ±0.4; about ±0.3; about ±0.2; about ±0.1; about ±0.05; or less. In another embodiment, the crystalline form of polymorph C of Compound I (free base) exhibits an XRDP comprising peaks shown in Table 2 below:

TABLE 2

XRDP Table of Polymorph C of Compound I (free base)

| 2Theta | Flex Width | d-value | Intensity | I/Io |
|---|---|---|---|---|
| 4.700 | 0.259 | 18.7856 | 1578 | 8 |
| 5.720 | 0.282 | 15.4378 | 21302 | 100 |
| 7.900 | 0.306 | 11.1820 | 355 | 2 |
| 10.940 | 0.282 | 8.0806 | 597 | 3 |
| 11.360 | 0.306 | 7.7828 | 852 | 4 |
| 12.480 | 0.212 | 7.0867 | 1205 | 6 |
| 12.640 | 0.306 | 6.9974 | 1422 | 7 |
| 15.700 | 0.400 | 5.6398 | 803 | 4 |
| 17.420 | 0.329 | 5.0866 | 778 | 4 |
| 17.940 | 0.329 | 4.9403 | 770 | 4 |
| 22.220 | 0.329 | 3.9974 | 364 | 2 |
| 23.540 | 0.376 | 3.7762 | 808 | 4 |
| 24.860 | 0.259 | 3.5786 | 448 | 3 |
| 25.940 | 0.329 | 3.4320 | 866 | 5 |
| 27.080 | 0.353 | 3.2901 | 597 | 3 |
| 29.200 | 0.282 | 3.0558 | 793 | 4 |

Figure 7:
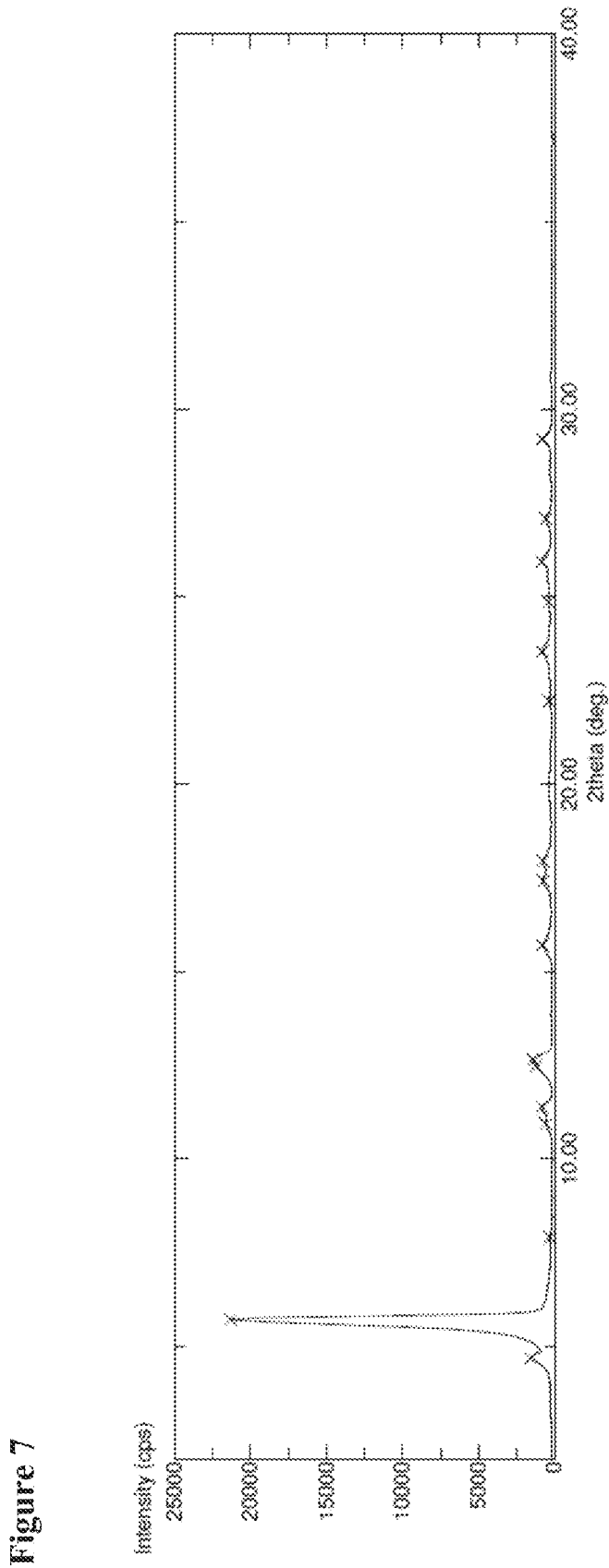
FIG. 7 is a graph of an XRPD pattern of polymorph C of Compound I (free base).

In one specific embodiment, the crystalline form of polymorph C of Compound I (free base) exhibits an XRDP that is substantially similar to FIG. 7.

Figure 8:
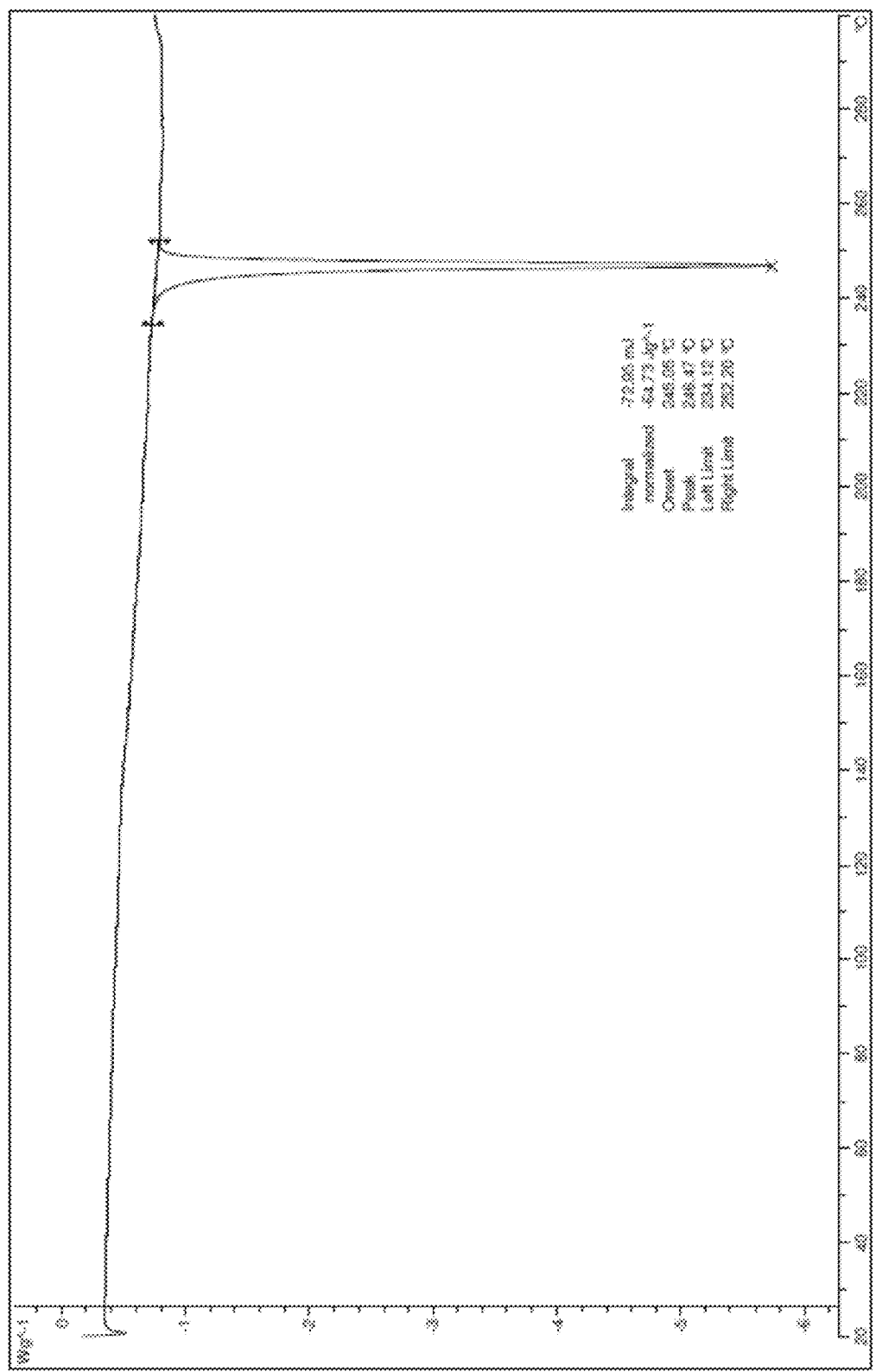
FIG. 8 is a DSC thermogram of polymorph C of Compound I (free base).

In one embodiment, the crystalline form of polymorph C of Compound I (free base) exhibits a DSC thermogram comprising a peak characteristic value at about 246.47° C. with the error of margin of about ±2.5; about ±2.0; about ±1.5; about ±1.0; about ±0.5; or less. In one specific embodiment, the crystalline form of polymorph C of Compound I (free base) exhibits a DSC thermogram that is substantially similar to FIG. 8.

Figure 9:
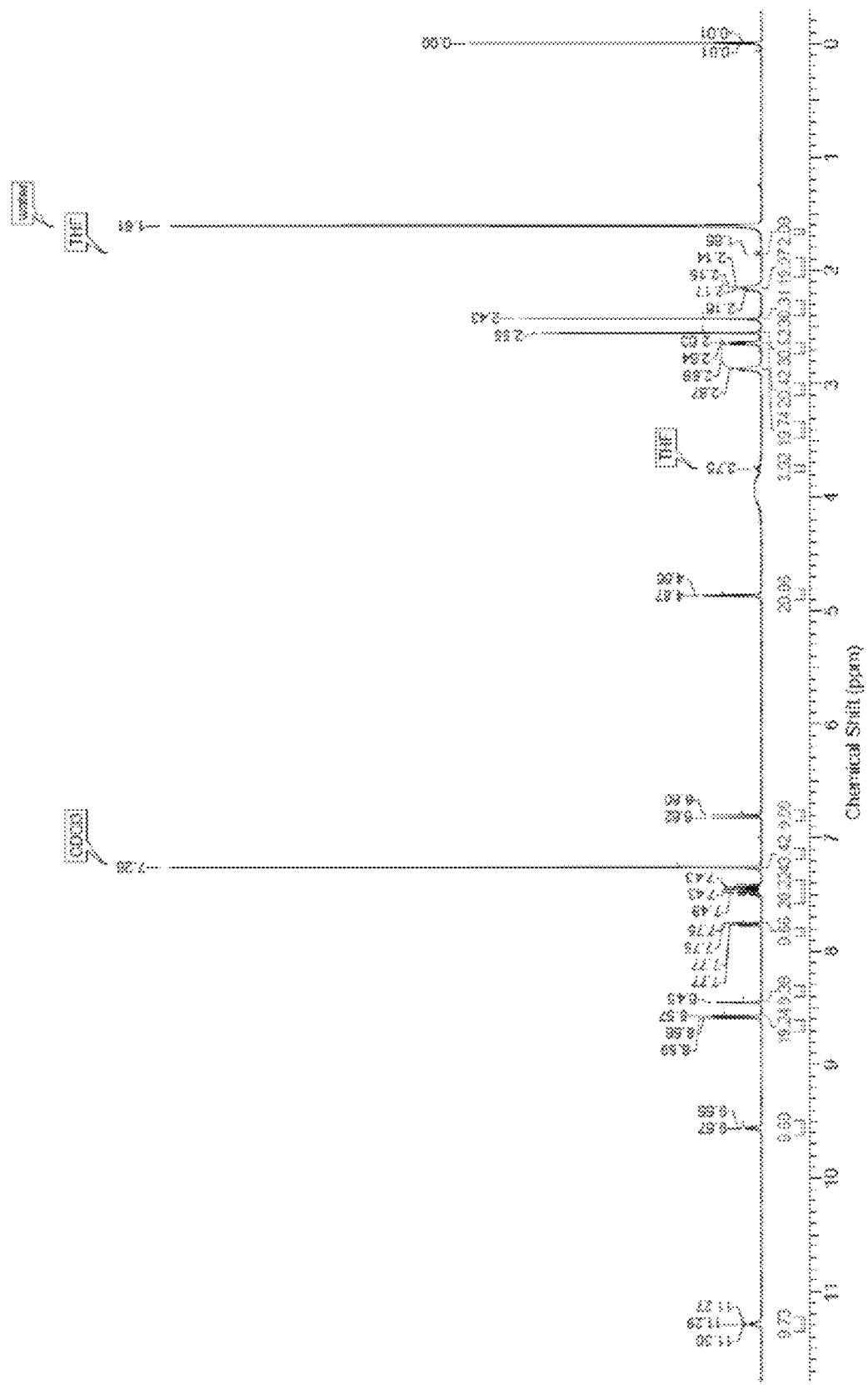
FIG. 9 is a $^1$H NMR spectrum of polymorph C of Compound I (free base).
Figure 10A:
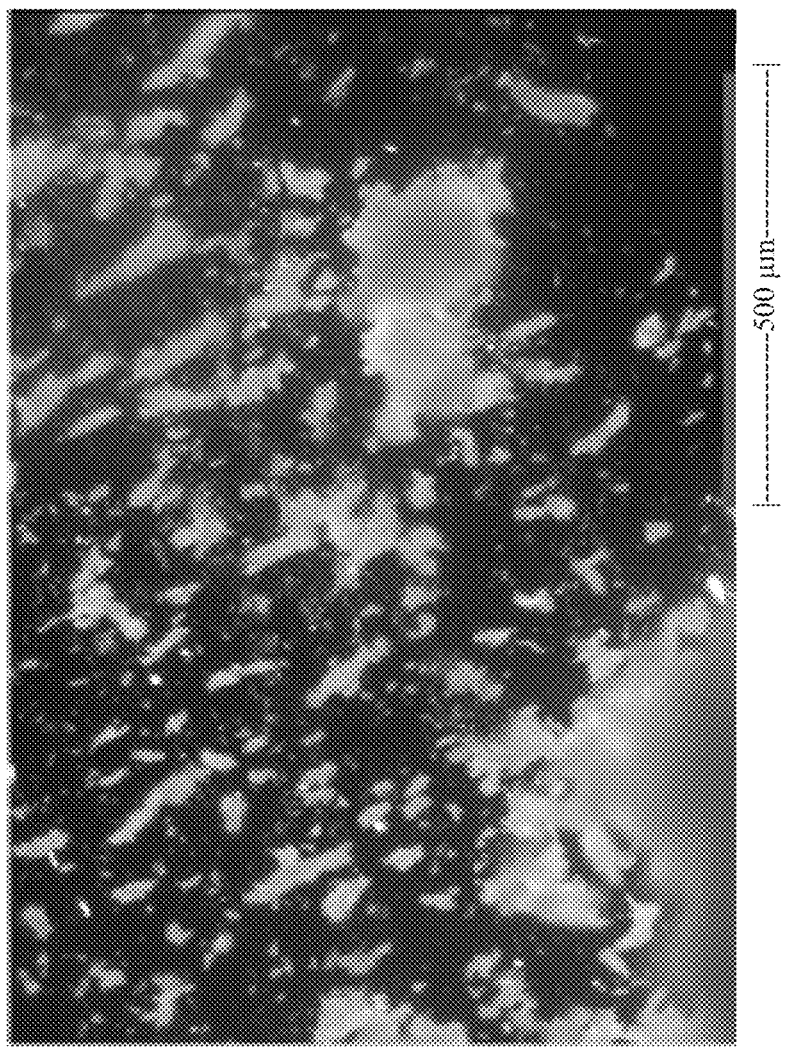
FIG. 10A is a microscopy picture of polymorph C of Compound I (free base) using crossed polarization filters and FIG. 10B is a microscopy picture of polymorph C of Compound I (free base) with no polarization filters.
Figure 10B:
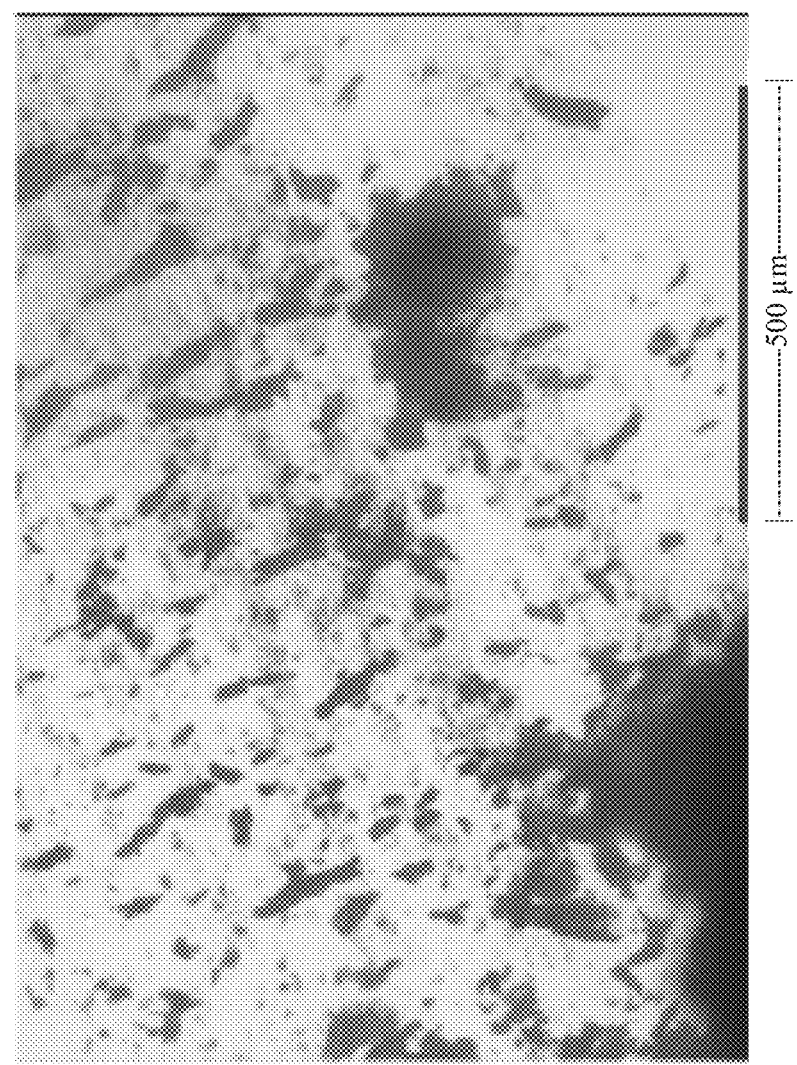

In one embodiment, the crystalline form of polymorph C of Compound I (free base) exhibits a $^1$H NMR spectrum that is substantially similar to FIG. 9. In another embodiment, the crystalline form of polymorph C of Compound I (free base) may consist of agglomerates of needles on a macroscopic scale, which are substantially similar to FIGS. 10A and 10B.

Polymorph E

In one embodiment, Polymorph E of Compound I (free base) exhibits an XRDP comprising peaks at about 5.680 degrees two-theta with the margin of error of about ±0.5; about ±0.4; about ±0.3; about ±0.2; about ±0.1; about ±0.05; or less. In another embodiment, the XRDP of the crystalline polymorph E of Compound I (free base) further comprises at least one peak at about 12.200, 12.600, 25.360, and 27.560 degrees two-theta with the margin of error of about ±0.5; about ±0.4; about ±0.3; about ±0.2; about ±0.1; about ±0.05; or less. In yet another embodiment, the crystalline form of polymorph E of Compound I (free base) exhibits an XRDP comprising peaks shown in the Table 3 below:

TABLE 3

XRDP Table of Polymorph E of Compound I (free base)

| 2Theta | Flex Width | d-value | Intensity | I/Io |
|---|---|---|---|---|
| 5.680 | 0.188 | 15.5465 | 22340 | 100 |
| 7.700 | 0.188 | 11.4720 | 450 | 3 |
| 10.020 | 0.188 | 8.8204 | 427 | 2 |
| 11.340 | 0.282 | 7.7965 | 1248 | 6 |
| 11.720 | 0.165 | 7.5445 | 562 | 3 |
| 12.200 | 0.188 | 7.2487 | 1655 | 8 |
| 12.600 | 0.212 | 7.0195 | 2116 | 10 |
| 13.300 | 0.188 | 6.6516 | 417 | 2 |
| 13.660 | 0.188 | 6.4771 | 358 | 2 |
| 14.820 | 0.188 | 5.9726 | 834 | 4 |
| 15.040 | 0.141 | 5.8857 | 523 | 3 |
| 15.500 | 0.282 | 5.7121 | 401 | 2 |
| 16.220 | 0.282 | 5.4601 | 1410 | 7 |
| 16.720 | 0.165 | 5.2979 | 458 | 3 |
| 17.060 | 0.212 | 5.1931 | 506 | 3 |
| 18.000 | 0.188 | 4.9240 | 773 | 4 |
| 18.460 | 0.212 | 4.8023 | 575 | 3 |
| 19.080 | 0.235 | 4.6476 | 350 | 2 |
| 20.280 | 0.400 | 4.3753 | 538 | 3 |
| 20.680 | 0.235 | 4.2915 | 1016 | 5 |
| 21.060 | 0.212 | 4.2149 | 493 | 3 |
| 21.460 | 0.165 | 4.1373 | 476 | 3 |
| 21.980 | 0.259 | 4.0405 | 462 | 3 |
| 22.560 | 0.188 | 3.9380 | 917 | 5 |
| 22.940 | 0.212 | 3.8736 | 1385 | 7 |
| 23.680 | 0.188 | 3.7542 | 838 | 4 |
| 23.980 | 0.188 | 3.7079 | 1432 | 7 |
| 24.500 | 0.235 | 3.6304 | 472 | 3 |
| 25.360 | 0.212 | 3.5092 | 1579 | 8 |
| 27.560 | 0.212 | 3.2338 | 1975 | 9 |
| 28.120 | 0.353 | 3.1707 | 500 | 3 |
| 28.680 | 0.212 | 3.1100 | 1112 | 5 |
| 29.360 | 0.235 | 3.0395 | 393 | 2 |
| 30.000 | 0.282 | 2.9761 | 476 | 3 |
| 30.700 | 0.165 | 2.9099 | 552 | 3 |
| 30.980 | 0.165 | 2.8842 | 455 | 3 |
| 31.840 | 0.259 | 2.8082 | 492 | 3 |
| 39.800 | ***** | 2.2630 | 402 | 2 |

Figure 11:
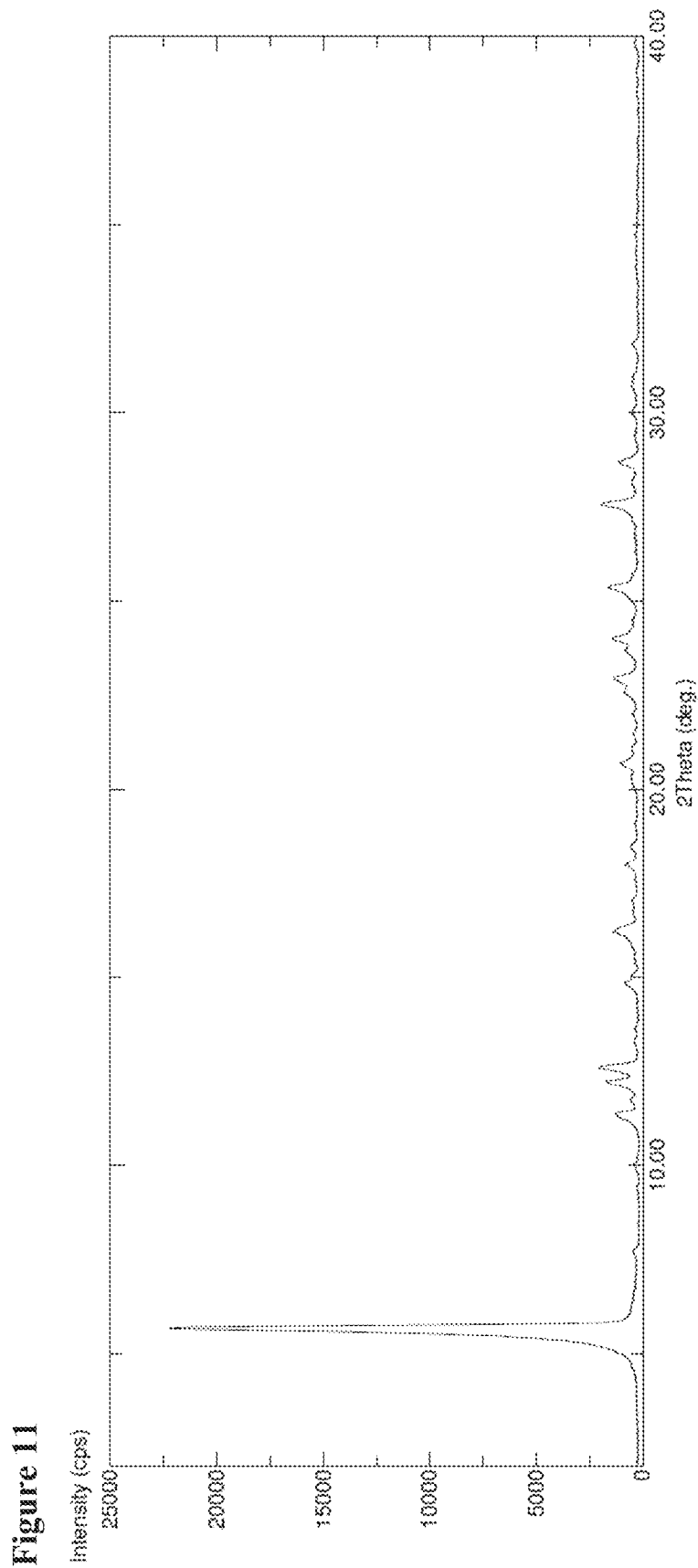
FIG. 11 is a graph of an XRPD pattern of polymorph E of Compound I (free base).

In one specific embodiment, the crystalline form of polymorph E of Compound I (free base) exhibits an XRDP that is substantially similar to FIG. 11.

Figure 12:
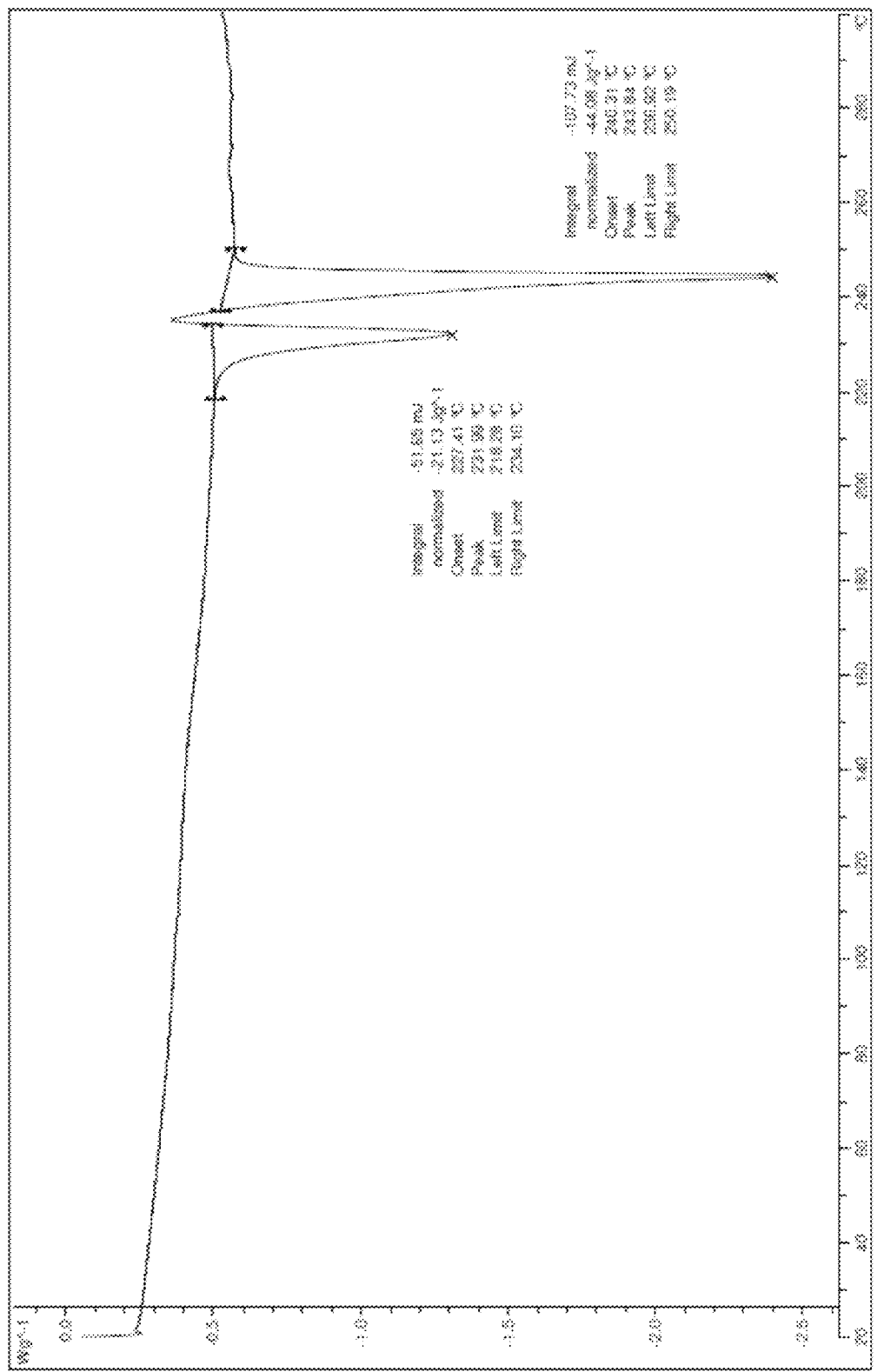
FIG. 12 is a DSC thermogram of polymorph E of Compound I (free base).

In one embodiment, the crystalline form of polymorph E of Compound I (free base) exhibits a DSC thermogram comprising a peak characteristic value at about 231.99° C. with the error of margin of about ±2.5; about ±2.0; about ±1.5; about ±1.0; about ±0.5; or less. In one specific embodiment, the crystalline form of polymorph E of Compound I (free base) exhibits a DSC thermogram that is substantially similar to FIG. 12.

Figure 13:
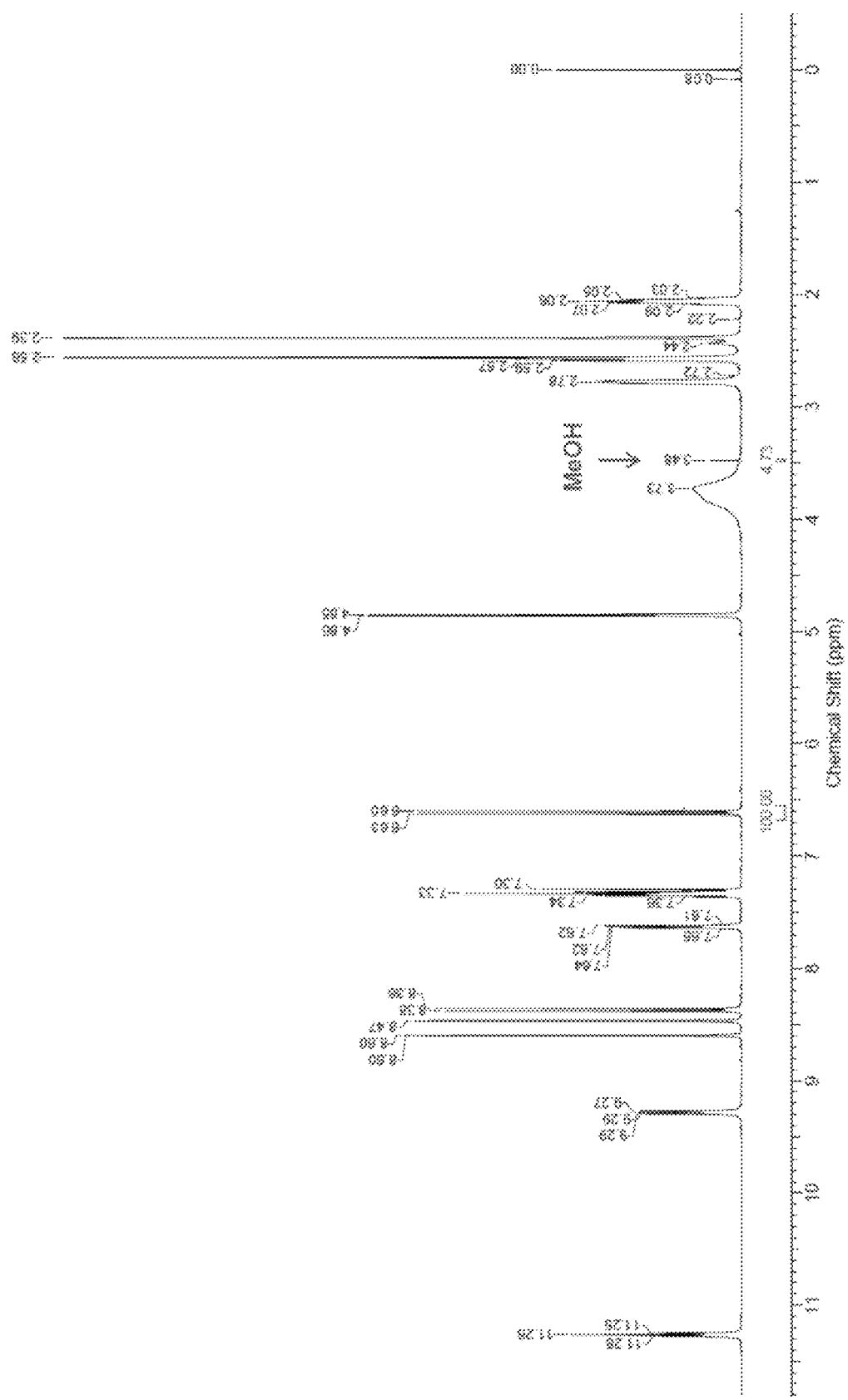
FIG. 13 is a $^1$H NMR spectrum of polymorph E of Compound I (free base).
Figure 14A:
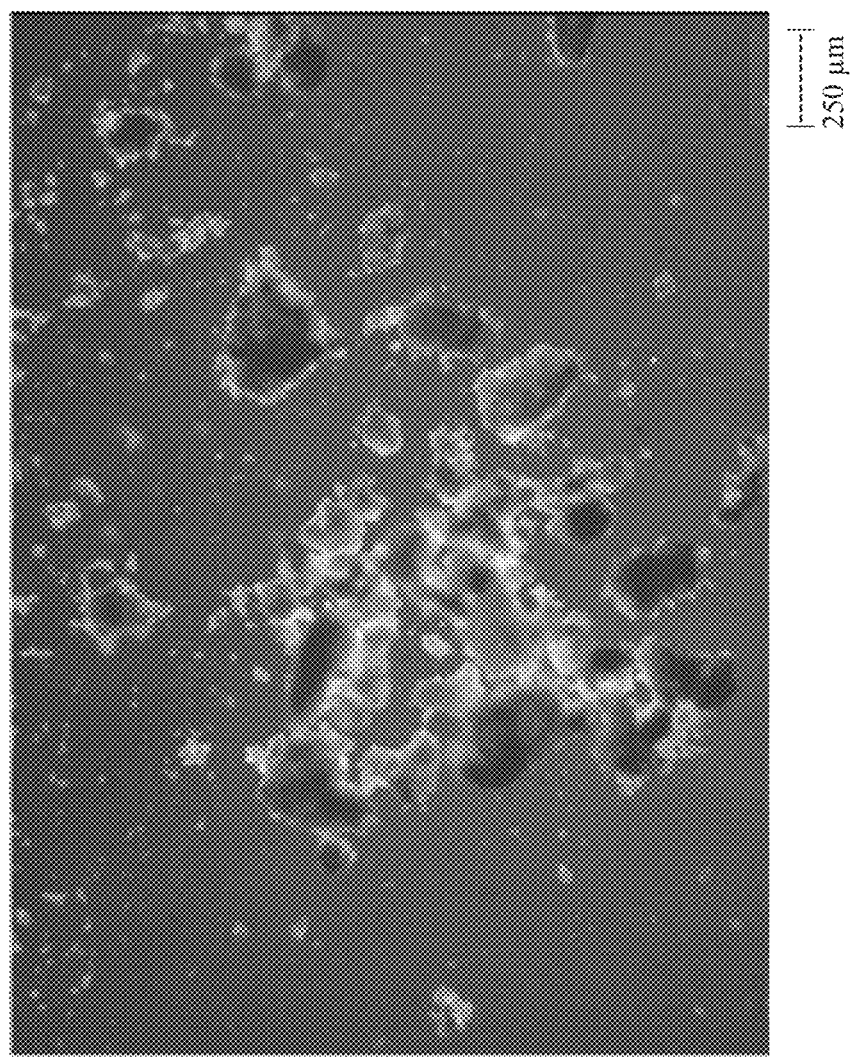
FIG. 14A is a microscopy picture of polymorph E of Compound I (free base) using crossed polarization filters and FIG. 14B is a microscopy picture of polymorph E of Compound I (free base) with no polarization filters.
Figure 14B:
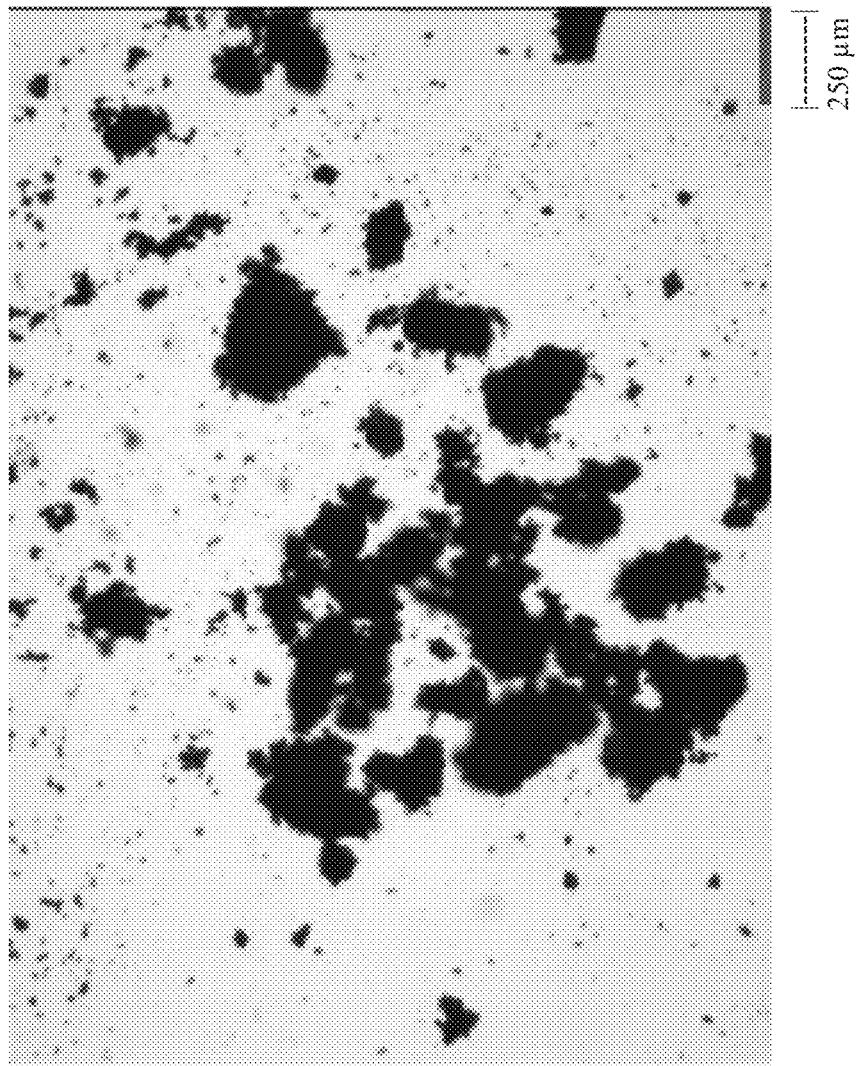
Figure 15:
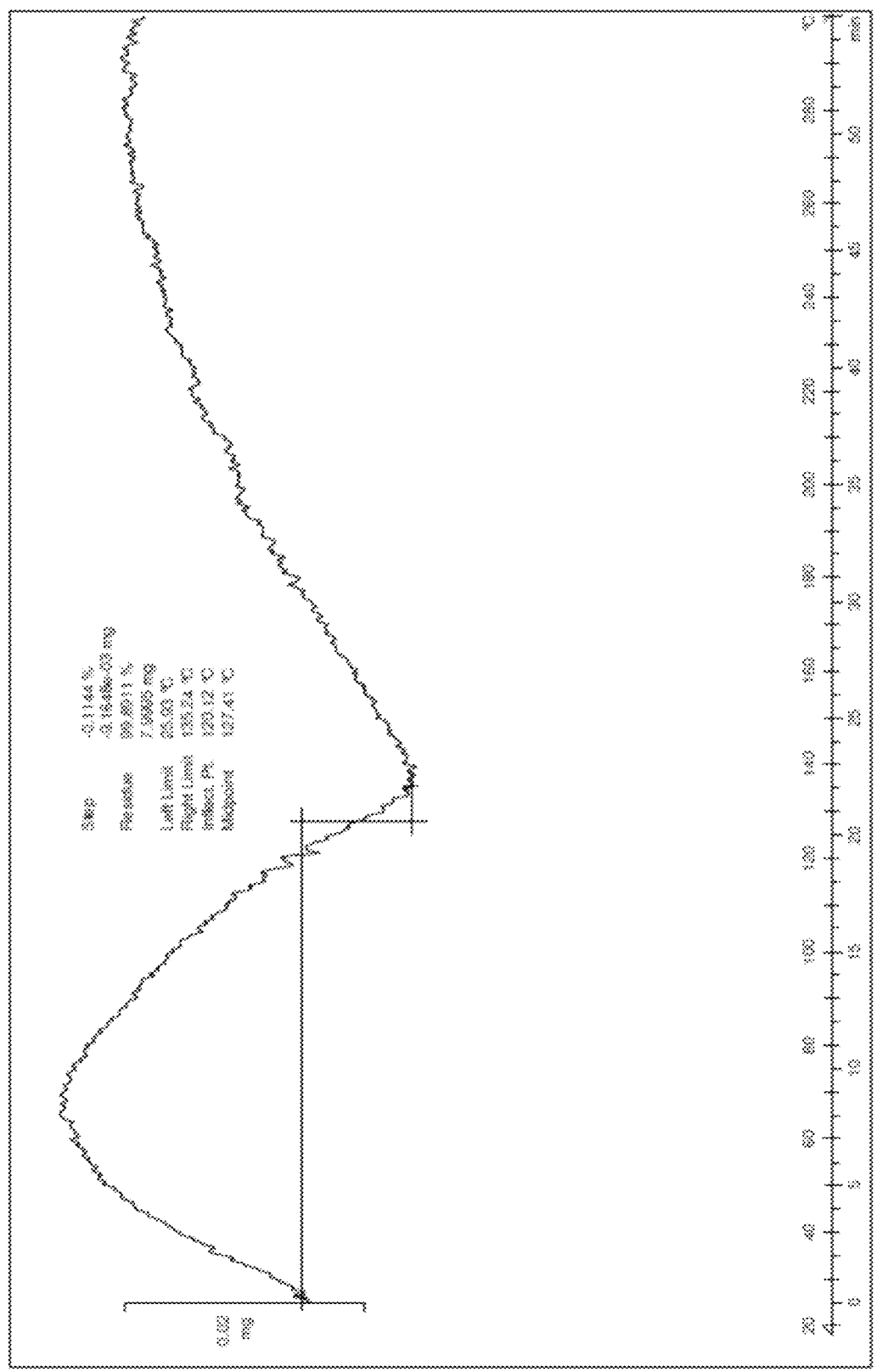
FIG. 15 is a thermogravimetric analysis (TGA) thermogram of polymorph E of Compound I (free base).

In one embodiment, the crystalline form of polymorph E of Compound I (free base) exhibits a $^1$H NMR spectrum that is substantially similar to FIG. 13. In another embodiment, the crystalline form of polymorph E of Compound I (free base) may be substantially similar to FIGS. 14A and 14B.

Polymorph G

In one embodiment, polymorph G of Compound I (free base) exhibits an XRDP comprising peaks at about 5.000 and 6.060 degrees two-theta with the margin of error of about ±0.5; about ±0.4; about ±0.3; about ±0.2; about ±0.1; about ±0.05; or less. In another embodiment, the crystalline form of polymorph G of Compound I (free base) exhibits an XRDP comprising peaks shown in Table 4 below:

TABLE 4

XRDP Table of Polymorph G of Compound I (free base)

| 2Theta | Flex Width | d-value | Intensity | I/Io |
|---|---|---|---|---|
| 5.000 | 0.212 | 17.6591 | 3953 | 32 |
| 6.060 | 0.306 | 14.5724 | 12680 | 100 |
| 7.800 | 0.282 | 11.3251 | 485 | 4 |
| 9.760 | 0.259 | 9.0548 | 503 | 4 |
| 10.360 | 0.282 | 8.5317 | 412 | 4 |
| 13.400 | 0.259 | 6.6022 | 868 | 7 |
| 15.000 | 0.329 | 5.9014 | 625 | 5 |
| 15.980 | 0.541 | 5.5416 | 709 | 6 |
| 18.120 | 0.212 | 4.8916 | 393 | 4 |
| 19.120 | 0.282 | 4.6380 | 390 | 4 |
| 22.320 | 0.306 | 3.9798 | 480 | 4 |
| 23.480 | 0.259 | 3.7857 | 1035 | 9 |
| 26.000 | 0.259 | 3.4242 | 729 | 6 |
| 26.400 | 0.259 | 3.3732 | 865 | 7 |
| 27.700 | 0.282 | 3.2178 | 505 | 4 |

Figure 16:
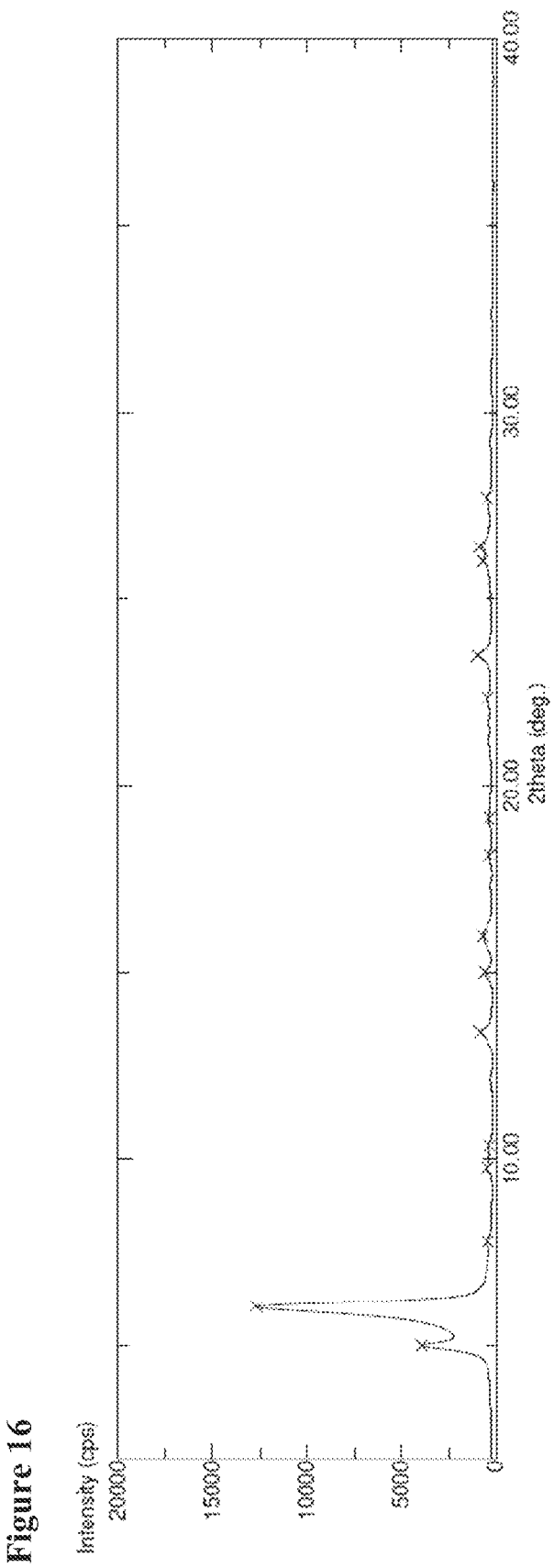
FIG. 16 is a graph of an XRPD pattern of polymorph G of Compound I (free base).

In one specific embodiment, the crystalline form of polymorph G of Compound I (free base) exhibits an XRDP that is substantially similar to FIG. 16.

Figure 17:
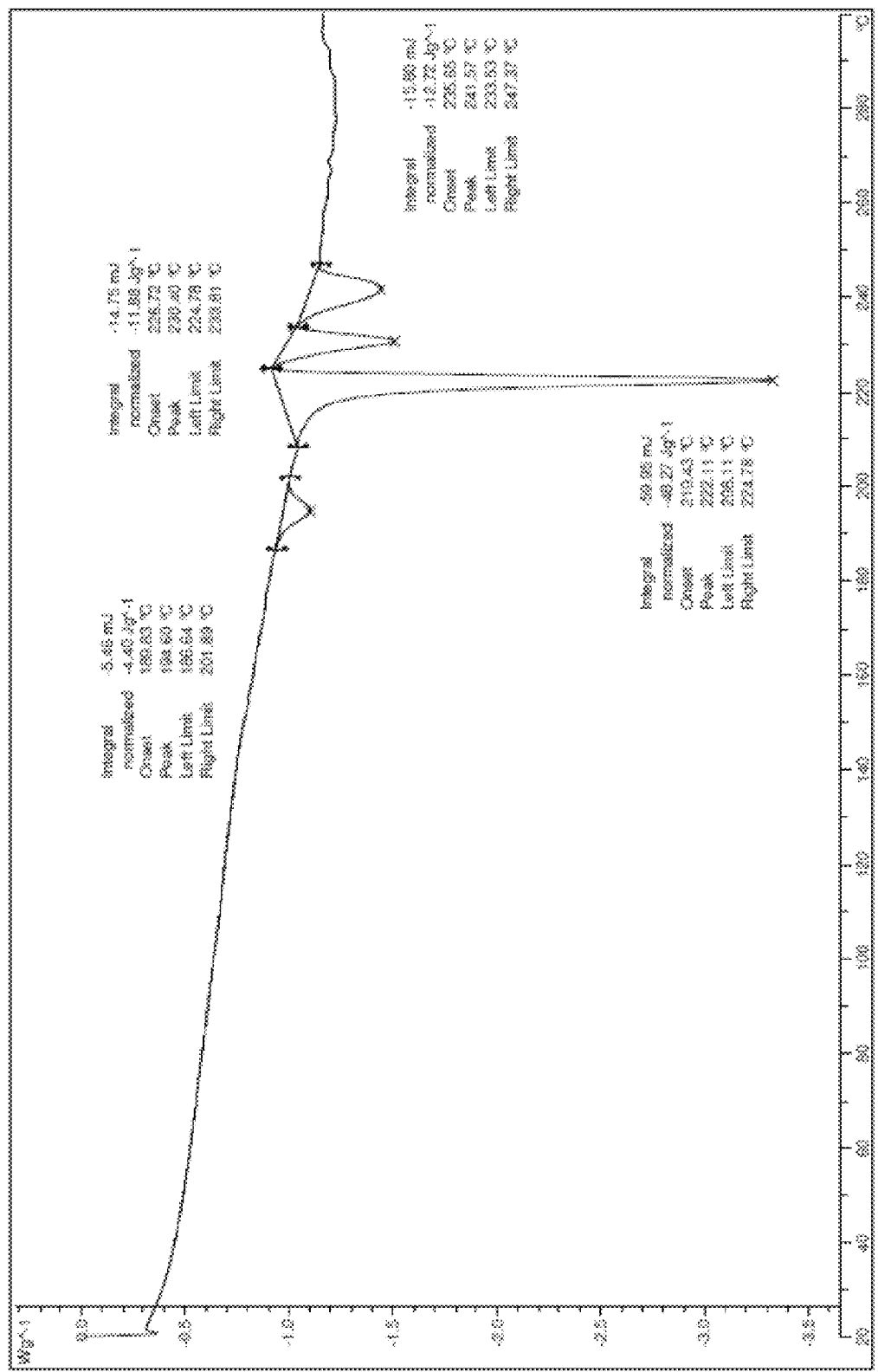
FIG. 17 is a DSC thermogram of polymorph G of Compound I (free base).

In one embodiment, the crystalline form of polymorph G of Compound I (free base) exhibits a DSC thermogram comprising a peak characteristic value at about 222.11° C. with the error of margin of about ±2.5; about ±2.0; about ±1.5; about ±1.0; about ±0.5; or less. In one specific embodiment, the crystalline form of polymorph G of Compound I (free base) exhibits a DSC thermogram that is substantially similar to FIG. 17.

Figure 18:
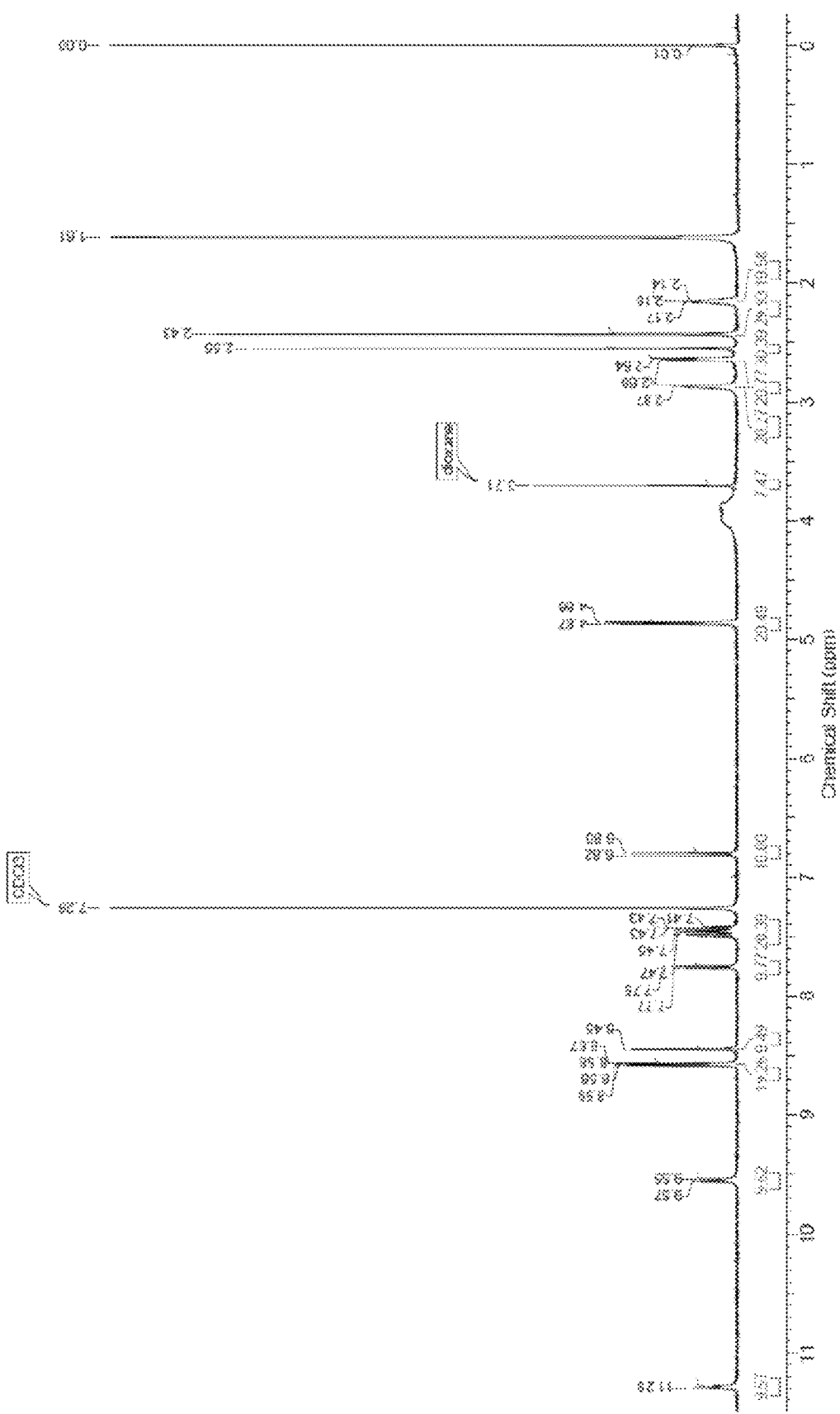
FIG. 18 is a $^1$H NMR spectrum of polymorph G of Compound I (free base).
Figure 19A:
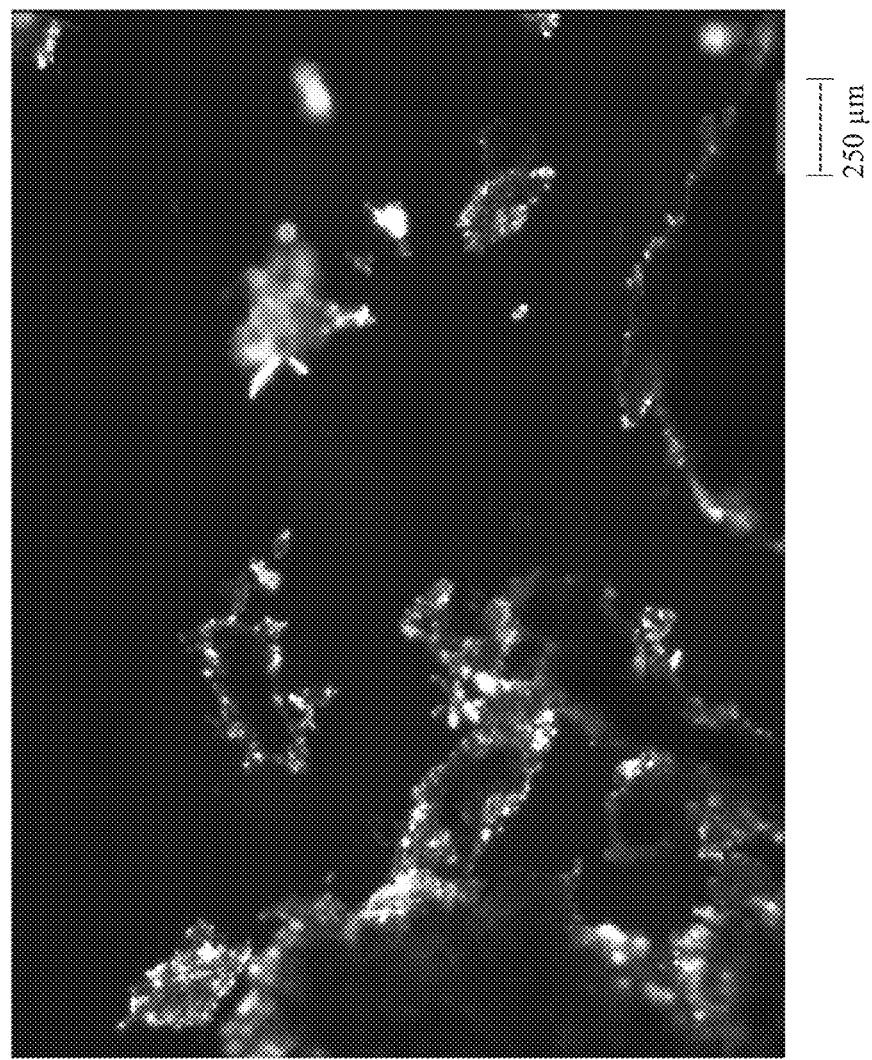
FIG. 19A is a microscopy picture of polymorph G of Compound I (free base) using crossed polarization filters and FIG. 19B is a microscopy picture of polymorph G of Compound I (free base) with no polarization filters.
Figure 19B:
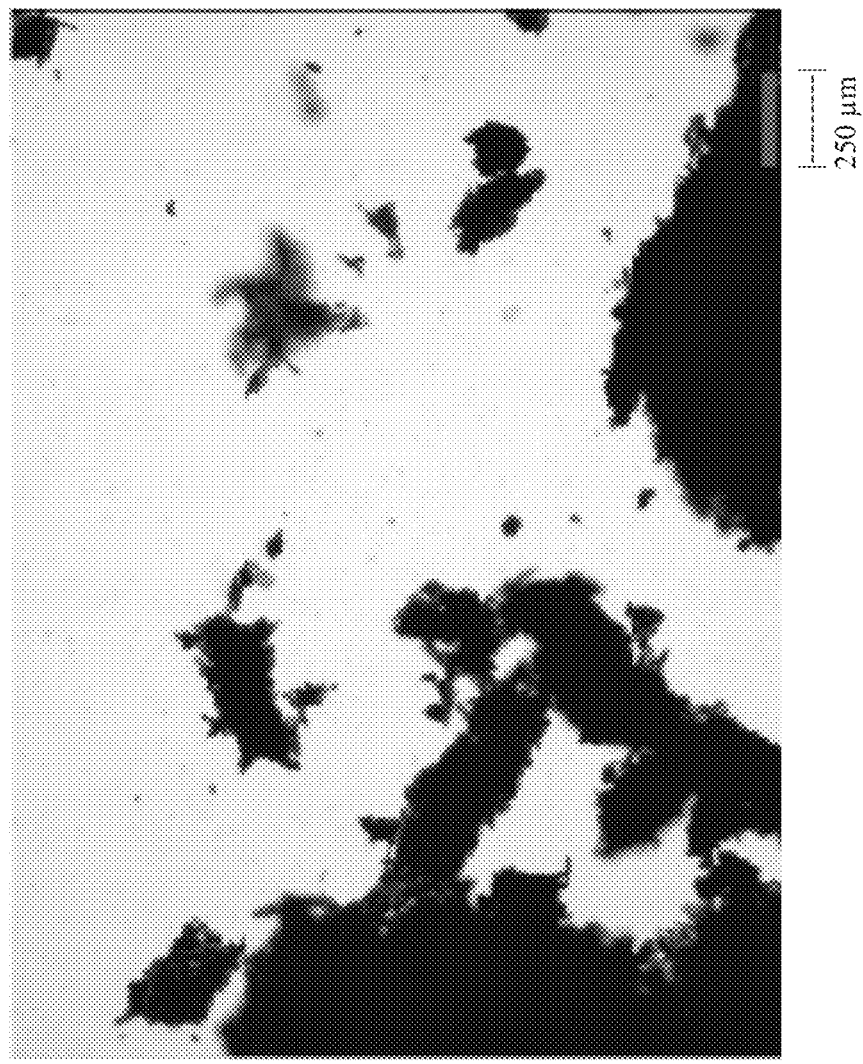

In one embodiment, the crystalline form of polymorph G of Compound I (free base) exhibits a $^1$H NMR spectrum that is substantially similar to FIG. 18. In another embodiment, the crystalline form of polymorph G of Compound I (free base) may be substantially similar to FIGS. 19A and 19B.

HCl Salt of Compound I

In one embodiment, the crystalline form of HCl salt of Compound I exhibits an XRDP comprising peaks at about 4.660 and 24.540 degrees two-theta with the margin of error of about ±0.5; about ±0.4; about ±0.3; about ±0.2; about ±0.1; about ±0.05; or less. In another embodiment, the XRDP of the crystalline form of HCl salt of Compound I further comprises one, two, three, or four peaks selected from at about 19.260, 20.160, 24.920, and 26.360 degrees two-theta with the margin of error of about ±0.5; about ±0.4; about ±0.3; about ±0.2; about ±0.1; about ±0.05; or less. In another embodiment, the XRDP of the crystalline form of HCl salt of Compound I further comprises one, two, or three peaks selected from at about 13.980, 14.540, 25.380 and 28.940 degrees two-theta with the margin of error of about ±0.5; about ±0.4; about ±0.3; about ±0.2; about ±0.1; about ±0.05; or less. In yet another embodiment, the crystalline form of a HCl salt of Compound I exhibits an XRDP comprising peaks shown in the table below:

TABLE 6

XRDP Table of a HCl Salt of Compound I

| 2Theta | Flex Width | d-value | Intensity | I/Io |
|---|---|---|---|---|
| 4.660 | 0.212 | 18.9468 | 4530 | 100 |
| 9.680 | 0.259 | 9.1294 | 622 | 14 |
| 13.980 | 0.306 | 6.3295 | 792 | 18 |
| 14.540 | 0.259 | 6.0870 | 790 | 18 |
| 15.720 | 0.306 | 5.6326 | 534 | 12 |
| 15.980 | 0.235 | 5.5416 | 600 | 14 |
| 16.740 | 0.400 | 5.2917 | 491 | 11 |
| 17.340 | 0.306 | 5.1099 | 460 | 11 |

TABLE 6-continued

XRDP Table of a HCl Salt of Compound I

| 2Theta | Flex Width | d-value | Intensity | I/Io |
|---|---|---|---|---|
| 18.580 | 0.353 | 4.7716 | 507 | 12 |
| 19.260 | 0.306 | 4.6046 | 895 | 20 |
| 20.160 | 0.329 | 4.4010 | 874 | 20 |
| 20.680 | 0.212 | 4.2915 | 418 | 10 |
| 22.160 | 0.212 | 4.0081 | 437 | 10 |
| 22.900 | 0.259 | 3.8803 | 523 | 12 |
| 23.360 | 0.188 | 3.8049 | 484 | 11 |
| 23.680 | 0.188 | 3.7542 | 446 | 10 |
| 24.540 | 0.282 | 3.6245 | 2963 | 66 |
| 24.920 | 0.212 | 3.5701 | 1581 | 35 |
| 25.380 | 0.259 | 3.5064 | 777 | 18 |
| 26.360 | 0.471 | 3.3783 | 998 | 23 |
| 26.940 | 0.212 | 3.3068 | 662 | 15 |
| 28.160 | 0.259 | 3.1663 | 580 | 13 |
| 28.500 | 0.188 | 3.1293 | 671 | 15 |
| 28.940 | 0.259 | 3.0827 | 797 | 18 |
| 29.380 | 0.188 | 3.0375 | 589 | 13 |
| 29.620 | 0.259 | 3.0134 | 554 | 13 |
| 30.440 | 0.188 | 2.9341 | 420 | 10 |

Figure 21:
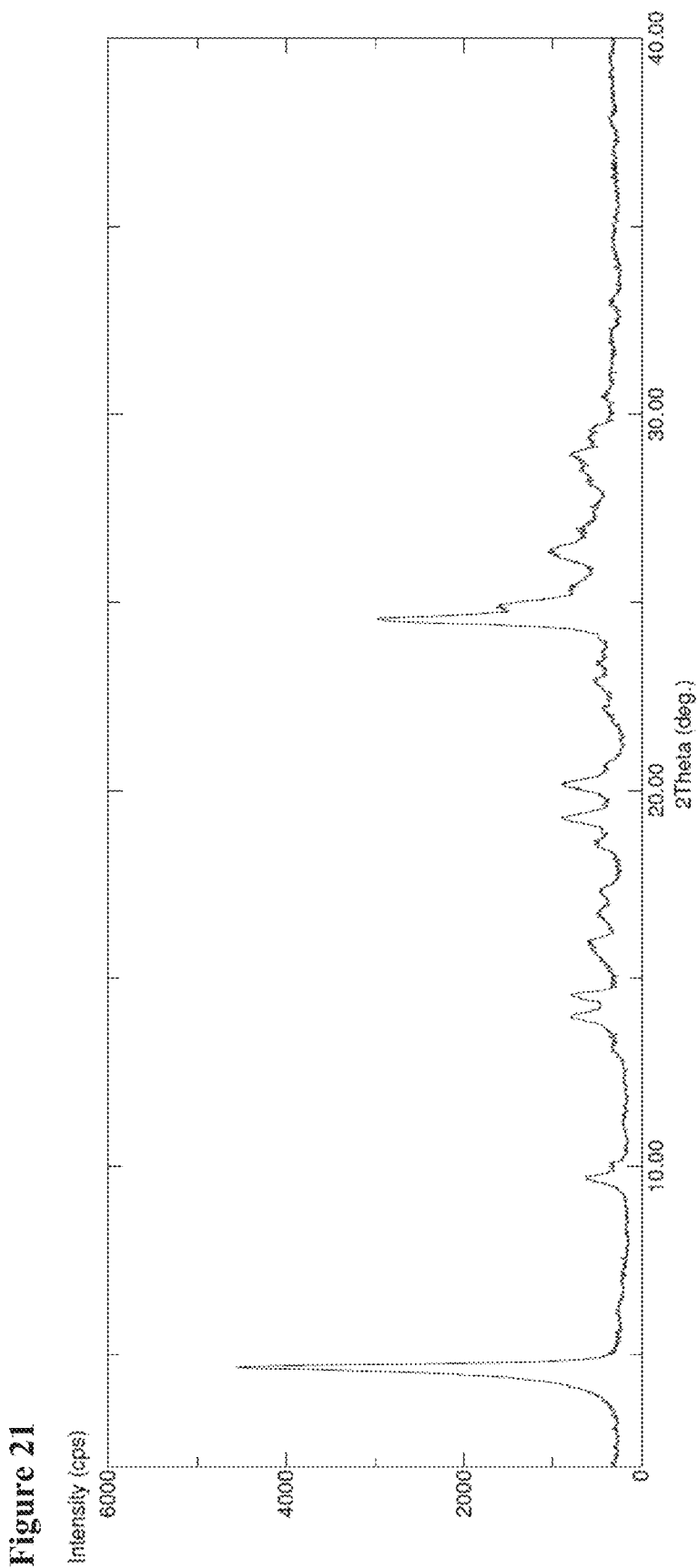
FIG. 21 is a graph of an XRPD pattern of HCl salt of Compound I.

In one specific embodiment, the crystalline form of a HCl salt of Compound I exhibits an XRDP that is substantially similar to FIG. 21.

Figure 22:
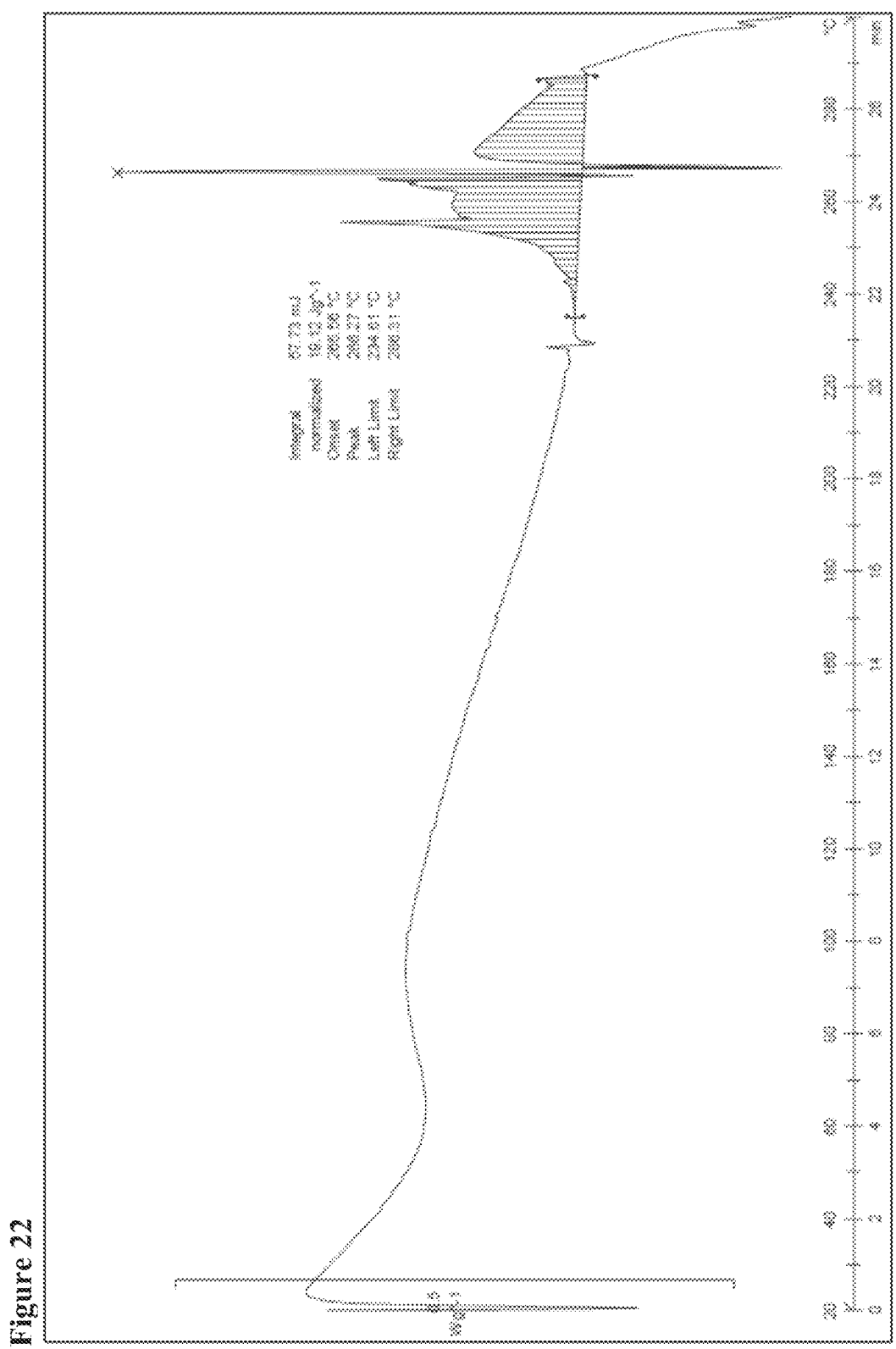
FIG. 22 is a DSC thermogram of HCl salt of Compound I.

In one embodiment, the crystalline form of a HCl salt of Compound I exhibits a DSC thermogram comprising a peak characteristic value at about 266.27° C. with the error of margin of about ±2.5; about ±2.0; about ±1.5; about ±1.0; about ±0.5; or less. In one specific embodiment, the crystalline form of a HCl salt of Compound I exhibits a DSC thermogram that is substantially similar to FIG. 22. In one embodiment, there is no clear melting point for the crystalline form of a HCl salt of Compound I.

Figure 23:
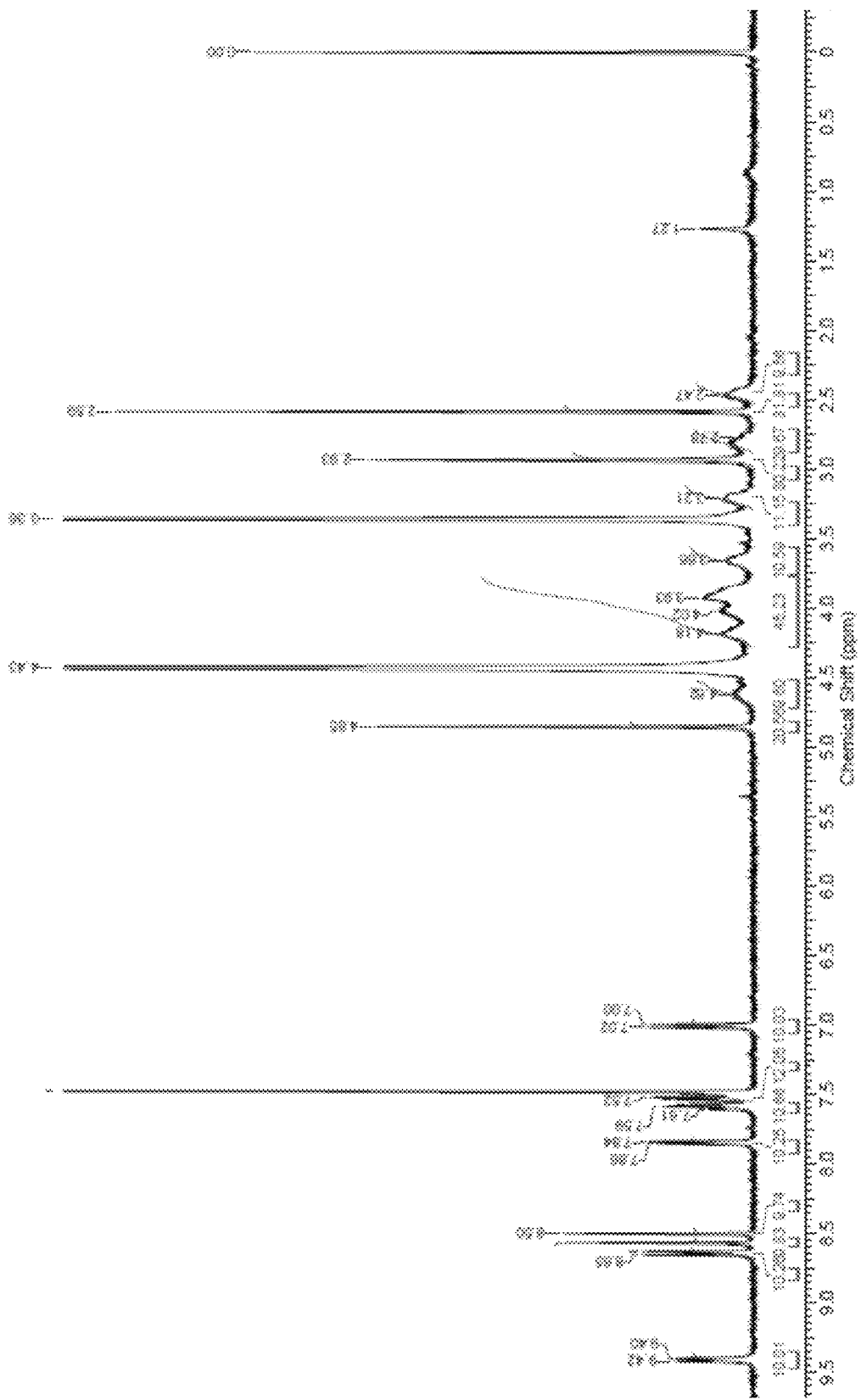
FIG. 23 is a $^1$H NMR spectrum of HCl salt of Compound I.
Figure 24:
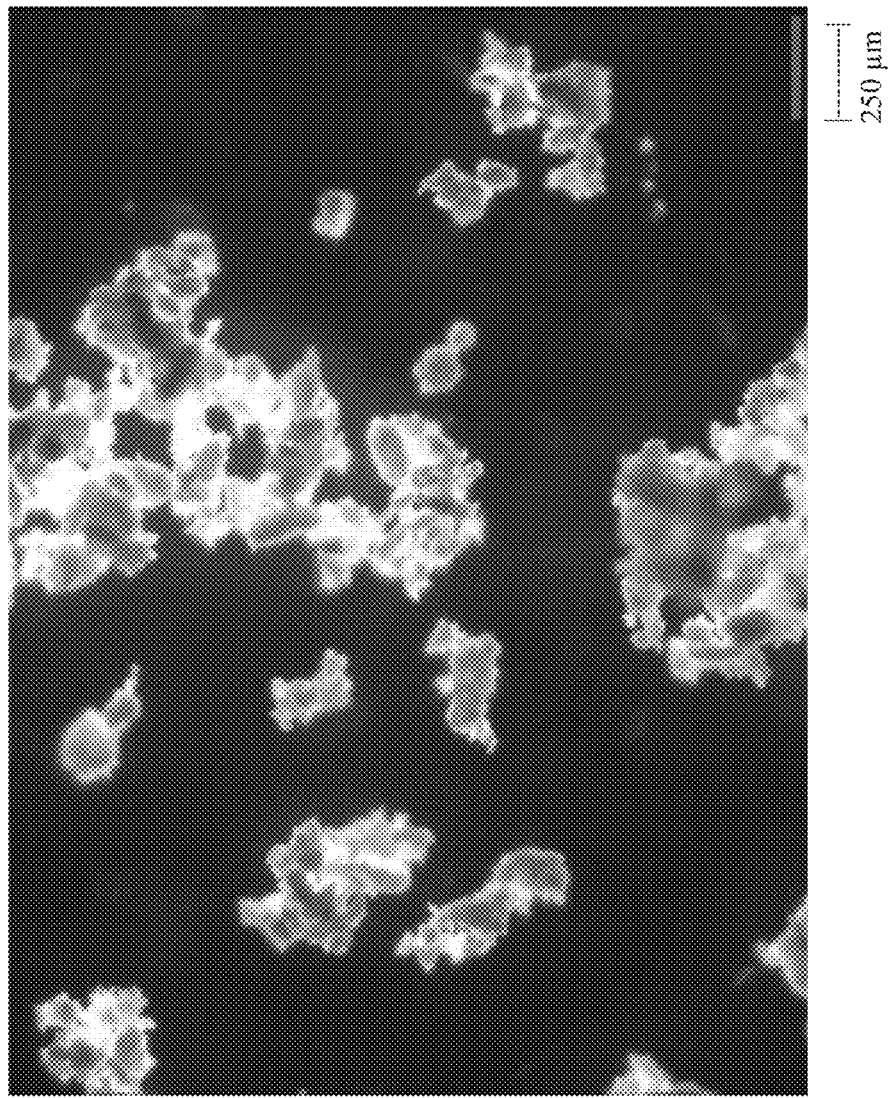
FIG. 24 is a microscopy picture of HCl salt of Compound I using polarization filters.

In one embodiment, the crystalline form of a HCl salt of Compound I exhibits a $^1$H NMR spectrum that is substantially similar to FIG. 23. In another embodiment, the crystalline form of a HCl salt of Compound I may consist of small needles that form agglomerates on a macroscopic scale, which may be substantially similar to FIG. 24. In one embodiment, the ratio of HCl and Compound I in the HCl salt of Compound I is about 1:1.

Maleic Acid Salt of Compound I

In one embodiment, the crystalline form of a maleic acid salt of Compound I exhibits an XRDP comprising peaks at about 7.400, 18.440, and 26.500 degrees two-theta with the margin of error of about ±0.5; about ±0.4; about ±0.3; about ±0.2; about ±0.1; about ±0.05; or less. In another embodiment, the XRDP of the crystalline maleic acid salt of Compound I further comprises one, two, three, or four peaks selected from at about 22.320, 23.920, 24.300, and 25.240 degrees two-theta with the margin of error of about ±0.5; about ±0.4; about ±0.3; about ±0.2; about ±0.1; about ±0.05; or less. In another embodiment, the XRDP of the crystalline maleic acid salt of Compound I further comprises one, two, three, or four peaks selected from at about 5.040, 15.080, 15.880, 20.860, and 28.540 degrees two-theta with the margin of error of about ±0.5; about ±0.4; about ±0.3; about ±0.2; about ±0.1; about ±0.05; or less. In yet another embodiment, the crystalline form of a maleic acid salt of Compound I exhibits an XRDP comprising peaks shown in the table below:

TABLE 7

XRDP Table of a Maleic Acid Salt of Compound I

| 2Theta | Flex Width | d-value | Intensity | I/Io |
|---|---|---|---|---|
| 5.040 | 0.235 | 17.5191 | 1648 | 48 |
| 6.280 | 0.212 | 14.0624 | 393 | 12 |
| 7.400 | 0.212 | 11.9364 | 3113 | 90 |
| 7.900 | 0.212 | 11.1820 | 424 | 13 |
| 8.480 | ***** | 10.4184 | 357 | 11 |
| 10.120 | 0.329 | 8.7335 | 435 | 13 |
| 10.400 | 0.188 | 8.4989 | 407 | 12 |
| 11.560 | 0.212 | 7.6486 | 577 | 17 |
| 12.180 | 0.329 | 7.2606 | 1336 | 39 |
| 13.100 | 0.282 | 6.7527 | 967 | 28 |
| 13.640 | 0.259 | 6.4865 | 1094 | 32 |
| 15.080 | 0.259 | 5.8702 | 1433 | 42 |
| 15.440 | 0.165 | 5.7342 | 707 | 21 |
| 15.880 | 0.306 | 5.5763 | 1600 | 46 |
| 17.220 | 0.259 | 5.1452 | 957 | 28 |
| 18.440 | 0.494 | 4.8075 | 2650 | 76 |
| 19.520 | 0.212 | 4.5439 | 691 | 20 |
| 19.800 | 0.235 | 4.4802 | 875 | 26 |
| 20.860 | 0.353 | 4.2549 | 1512 | 44 |
| 21.280 | 0.235 | 4.1719 | 946 | 28 |
| 22.320 | 0.329 | 3.9798 | 2242 | 65 |
| 23.580 | 0.165 | 3.7699 | 839 | 25 |
| 23.920 | 0.282 | 3.7171 | 1719 | 50 |
| 24.300 | 0.306 | 3.6598 | 2156 | 62 |
| 25.240 | 0.612 | 3.5256 | 1719 | 50 |
| 26.500 | 0.306 | 3.3607 | 3491 | 100 |
| 27.200 | 0.259 | 3.2758 | 681 | 20 |
| 27.880 | 0.306 | 3.1974 | 676 | 20 |
| 28.540 | 0.259 | 3.1250 | 1552 | 45 |
| 28.900 | 0.235 | 3.0869 | 1337 | 39 |
| 29.800 | 0.235 | 2.9957 | 757 | 22 |
| 30.220 | 0.165 | 2.9550 | 574 | 17 |
| 30.900 | 0.188 | 2.8915 | 565 | 17 |
| 31.180 | 0.165 | 2.8661 | 614 | 18 |
| 31.760 | 0.165 | 2.8151 | 612 | 18 |
| 33.560 | 0.282 | 2.6681 | 629 | 19 |
| 33.980 | 0.165 | 2.6361 | 531 | 16 |
| 34.300 | 0.259 | 2.6122 | 594 | 17 |
| 36.020 | 0.518 | 2.4913 | 608 | 18 |
| 37.360 | 0.306 | 2.4050 | 594 | 18 |

Figure 26:
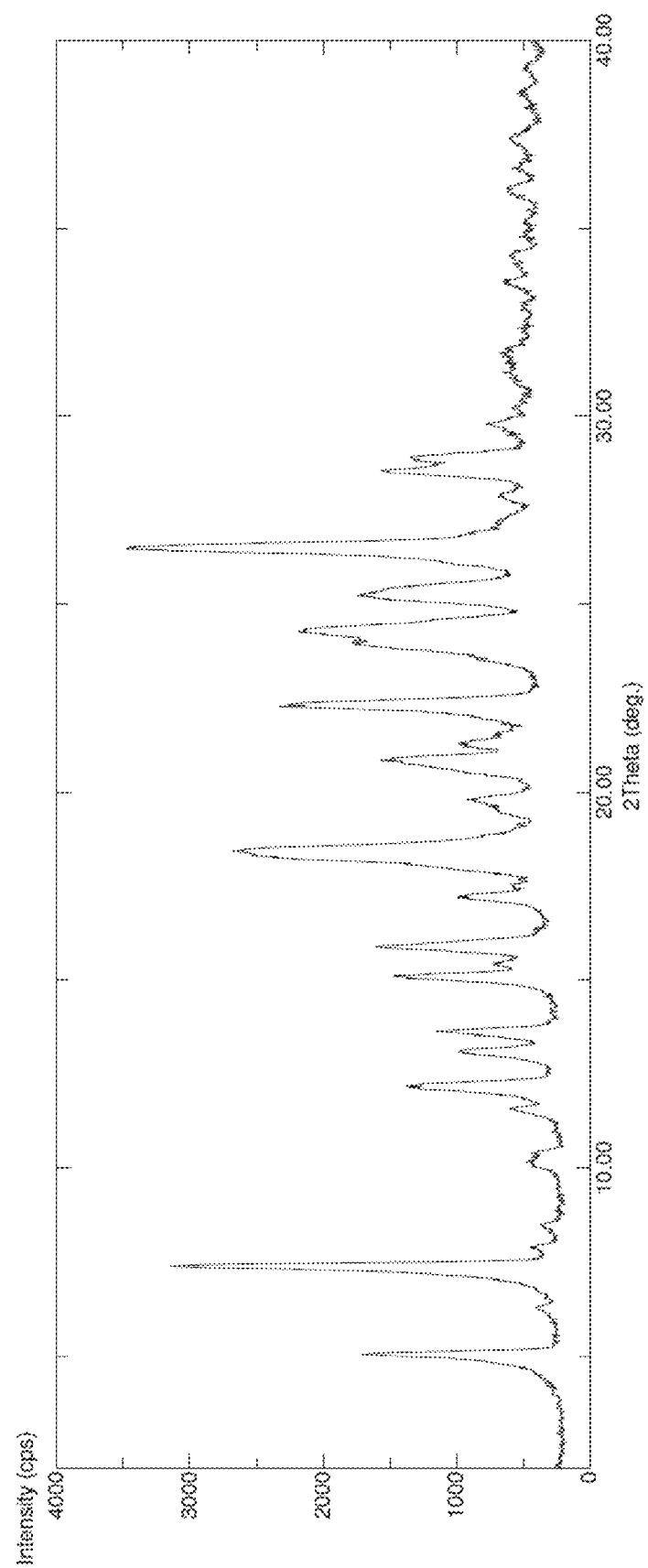
FIG. 26 is a graph of an XRPD pattern of maleic acid salt of Compound I.

In one specific embodiment, the crystalline form of a maleic acid salt of Compound I exhibits an XRDP that is substantially similar to FIG. 26.

Figure 27:
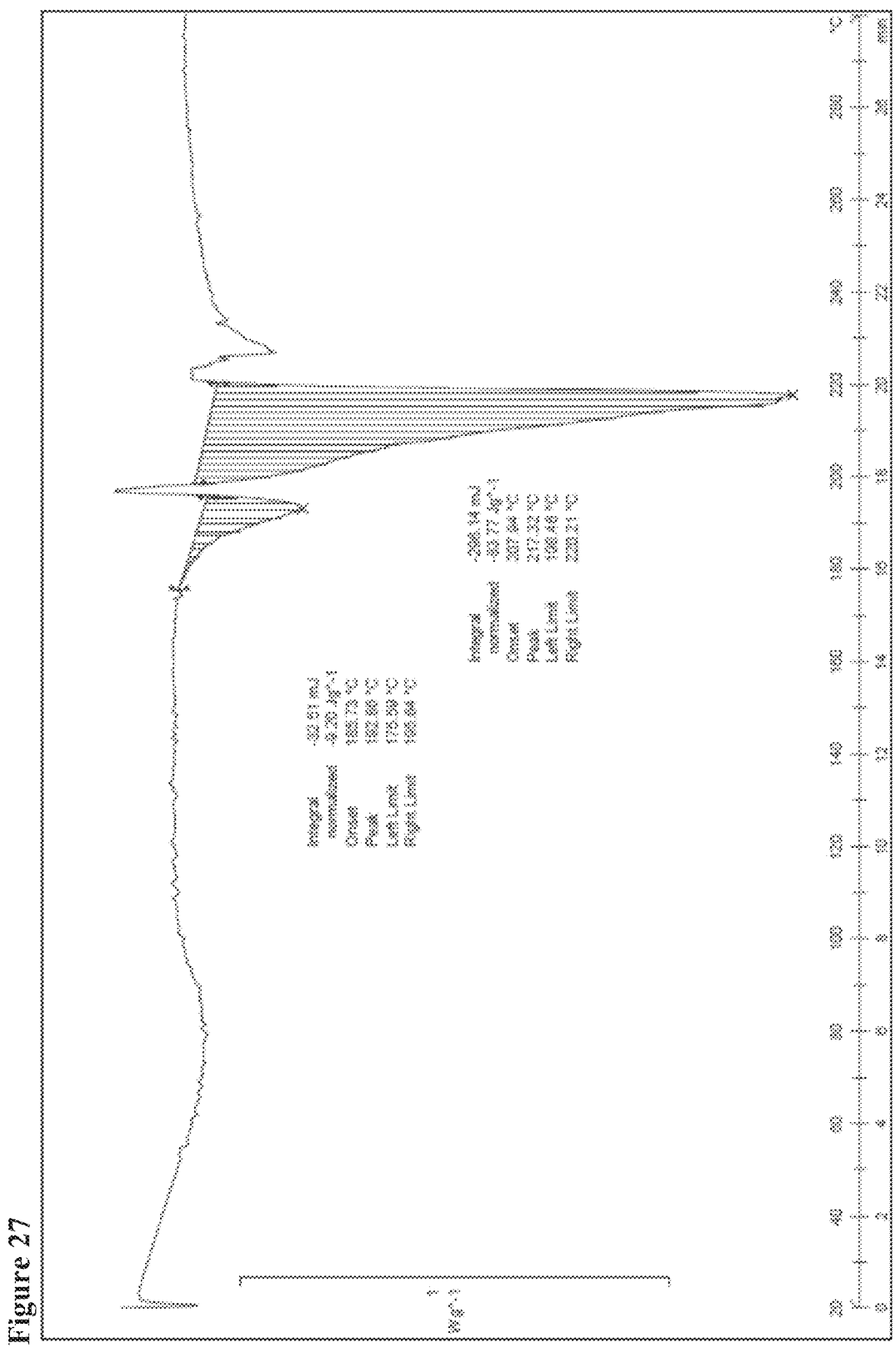
FIG. 27 is a DSC thermogram of maleic acid salt of Compound I.

In one embodiment, the crystalline form of maleic acid salt of Compound I exhibits a DSC thermogram comprising a peak characteristic value at about 217.32° C. with the error of margin of about ±2.5; about ±2.0; about ±1.5; about ±1.0; about ±0.5; or less. In one specific embodiment, the crystalline form of a maleic acid salt of Compound I exhibits a DSC thermogram that is substantially similar to FIG. 27.

Figure 28:
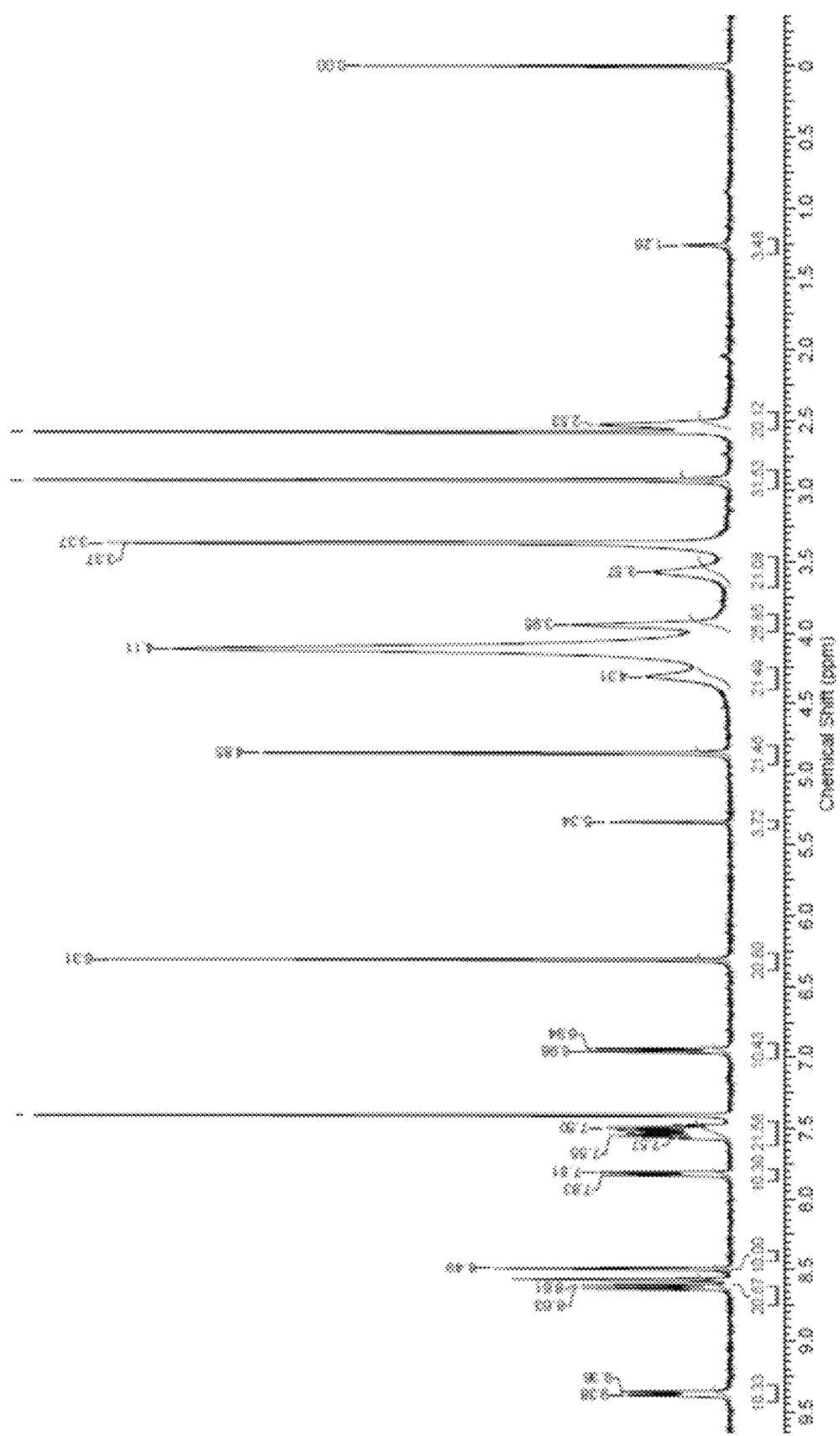
FIG. 28 is a $^1$H NMR spectrum of maleic acid salt of Compound I.
Figure 29:
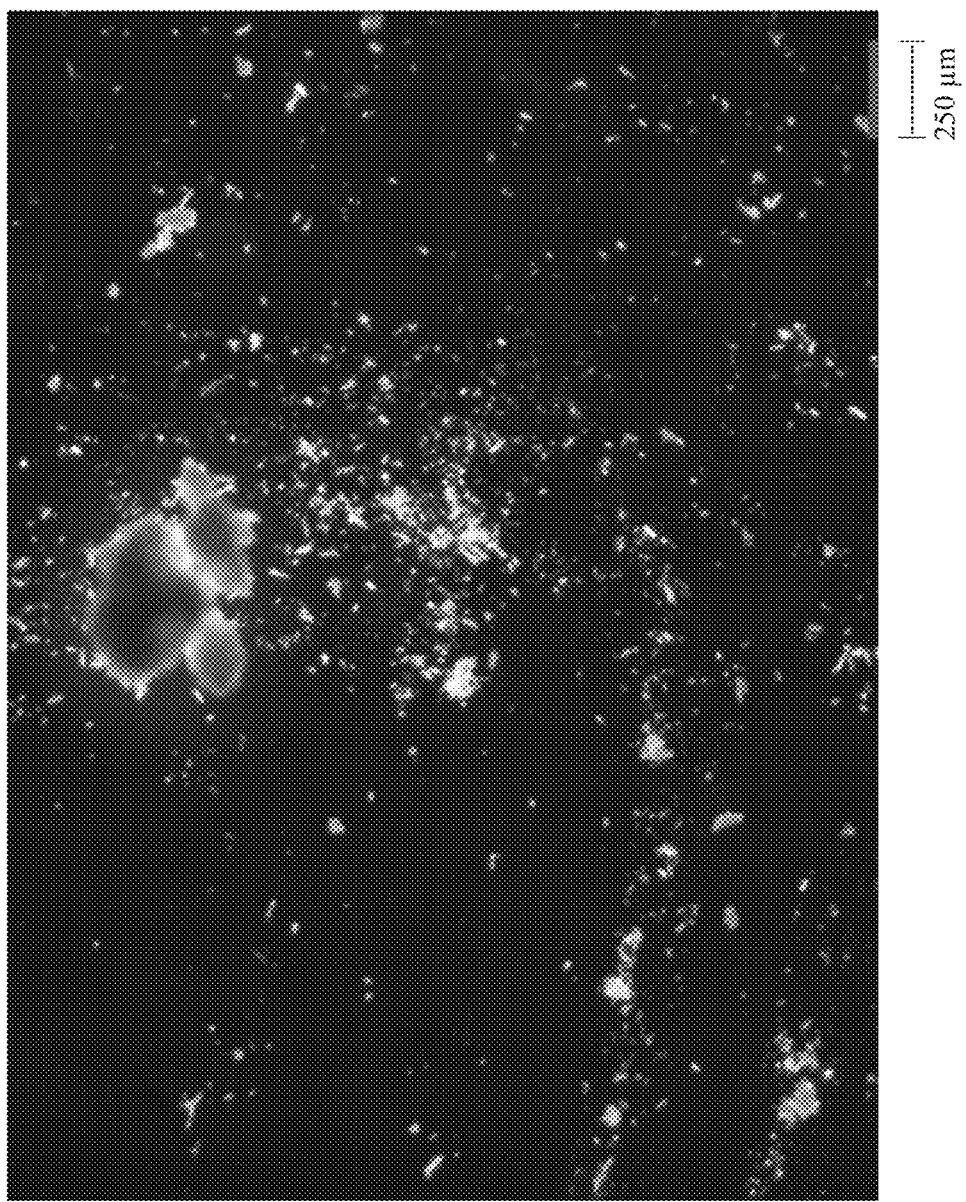
FIG. 29 is a microscopy picture of maleic acid salt of Compound I using polarization filters.

In one embodiment, the crystalline form of a maleic acid salt of Compound I exhibits a $^1$H NMR spectrum that is substantially similar to FIG. 28. In another embodiment, the crystalline form of a maleic salt of Compound I may consist of small needles that form agglomerates on a macroscopic scale, which may be substantially similar to FIG. 29. In one embodiment, the ratio of maleic acid and Compound I in the maleic acid salt of Compound I is about 1:1.

Fumaric Acid Salt of Compound I

In one embodiment, the crystalline form of a fumaric acid salt of Compound I exhibits an XRDP comprising peaks at about 6.360 and 24.800 degrees two-theta with the margin of error of about ±0.5; about ±0.4; about ±0.3; about ±0.2; about ±0.1; about ±0.05; or less. In another embodiment, the XRDP of the crystalline fumaric acid salt of Compound I further comprises at least one, two, or three peaks selected from at about 19.660, 20.420, and 26.860 degrees two-theta with the margin of error of about ±0.5; about ±0.4; about ±0.3; about ±0.2; about ±0.1; about ±0.05; or less. In another embodiment, the XRDP of the crystalline fumaric acid salt of Compound I further comprises at least one, two, three, or four peaks at about 12.680, 17.020, 25.180, and 28.280 degrees two-theta with the margin of error of about ±0.5; about ±0.4; about ±0.3; about ±0.2; about ±0.1; about ±0.05; or less. In yet another embodiment, the crystalline form of a fumaric acid salt of Compound I exhibits an XRDP comprising peaks shown in the table below:

TABLE 8

XRDP Table of a Fumaric Acid Salt of Compound I

| 2Theta | Flex Width | d-value | Intensity | I/Io |
|--------|------------|---------|-----------|------|
| 6.360  | 0.212      | 13.8857 | 3416      | 100  |
| 8.500  | 0.212      | 10.3940 | 599       | 18   |
| 10.860 | 0.212      | 8.1400  | 985       | 29   |
| 12.680 | 0.235      | 6.9754  | 1095      | 33   |
| 15.500 | 0.282      | 5.7121  | 822       | 25   |
| 16.360 | 0.212      | 5.4137  | 763       | 23   |
| 17.020 | 0.188      | 5.2052  | 1050      | 31   |
| 17.620 | 0.165      | 5.0293  | 451       | 14   |
| 18.040 | 0.259      | 4.9132  | 882       | 26   |
| 18.480 | 0.235      | 4.7972  | 611       | 18   |
| 19.660 | 0.235      | 4.5118  | 1654      | 49   |
| 20.420 | 0.259      | 4.3456  | 1917      | 57   |
| 21.260 | 0.212      | 4.1757  | 405       | 12   |
| 21.740 | 0.212      | 4.0846  | 519       | 16   |
| 22.020 | 0.165      | 4.0333  | 425       | 13   |
| 22.480 | 0.329      | 3.9518  | 455       | 14   |
| 23.100 | 0.541      | 3.8471  | 907       | 27   |
| 23.880 | 0.235      | 3.7232  | 711       | 21   |
| 24.180 | 0.212      | 3.6777  | 740       | 22   |
| 24.800 | 0.235      | 3.5871  | 2792      | 82   |
| 25.180 | 0.165      | 3.5338  | 1122      | 33   |
| 25.800 | 0.447      | 3.4503  | 938       | 28   |
| 26.300 | 0.259      | 3.3858  | 881       | 26   |
| 26.860 | 0.235      | 3.3165  | 1494      | 44   |
| 27.340 | 0.235      | 3.2594  | 905       | 27   |
| 27.900 | 0.188      | 3.1952  | 865       | 26   |
| 28.280 | 0.259      | 3.1531  | 1112      | 33   |
| 28.920 | 0.212      | 3.0848  | 720       | 22   |
| 30.200 | 0.282      | 2.9569  | 724       | 22   |

Figure 31:
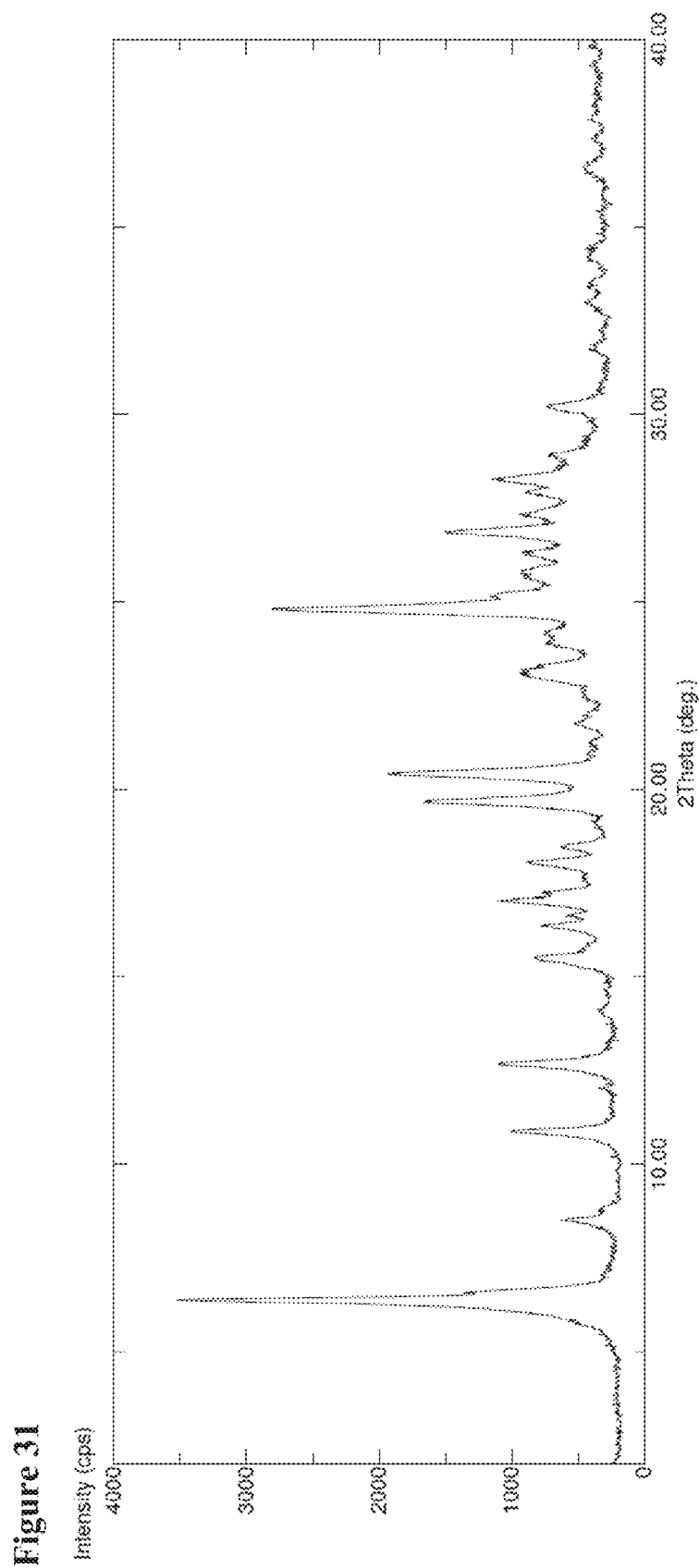
FIG. 31 is a graph of an XRPD pattern of fumaric acid salt of Compound I.

In one specific embodiment, the crystalline form of a fumaric acid salt of Compound I exhibits an XRDP that is substantially similar to FIG. 31.

Figure 32:
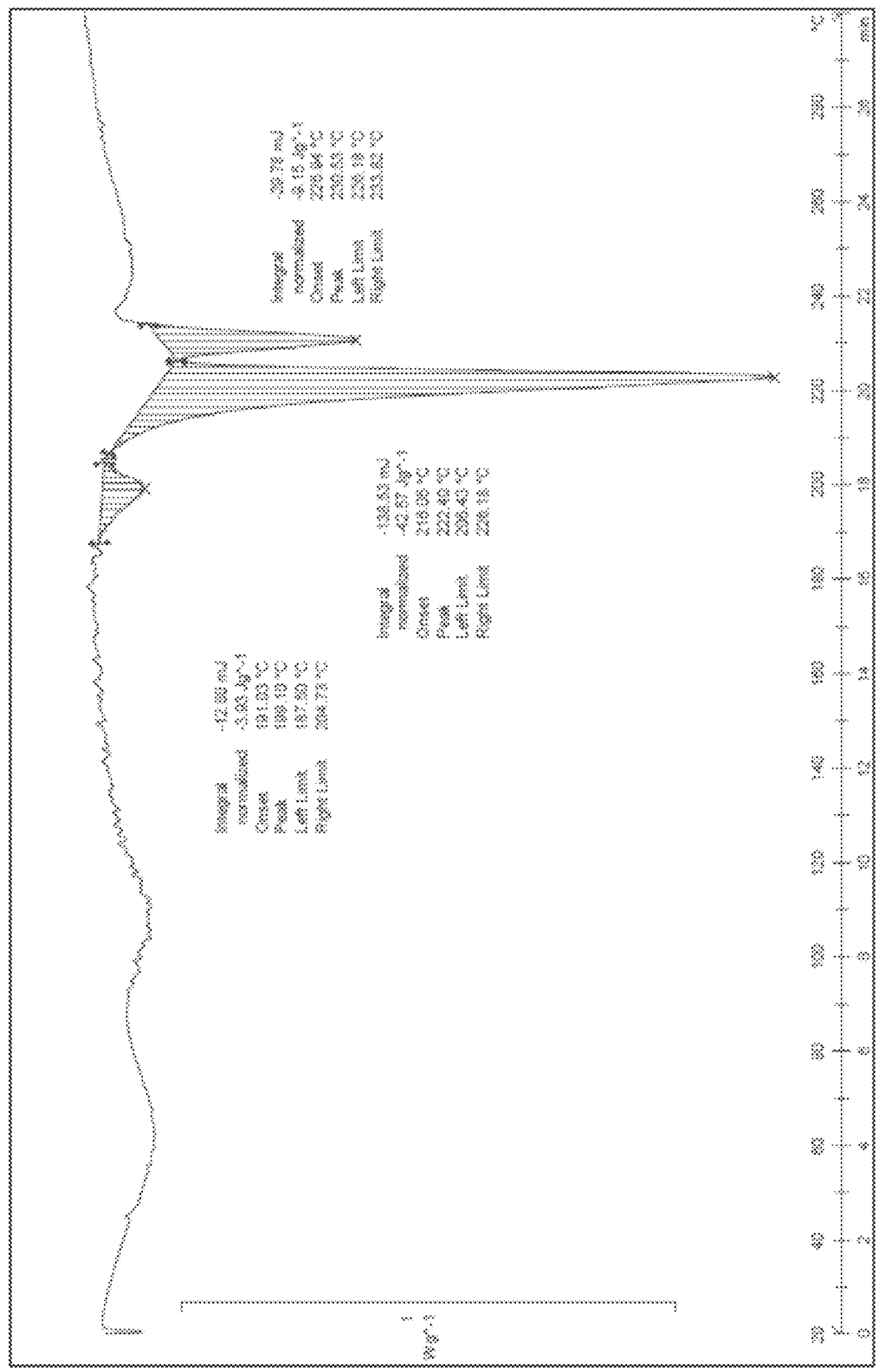
FIG. 32 is a DSC thermogram of fumaric acid salt of Compound I.

In one embodiment, the crystalline form of a fumaric acid salt of Compound I exhibits a DSC thermogram comprising a peak characteristic value at about 222.40° C. with the error of margin of about ±2.5; about ±2.0; about ±1.5; about ±1.0; about ±0.5; or less. In one specific embodiment, the crystalline form of a fumaric acid salt of Compound I exhibits a DSC thermogram that is substantially similar to FIG. 32.

Figure 33:
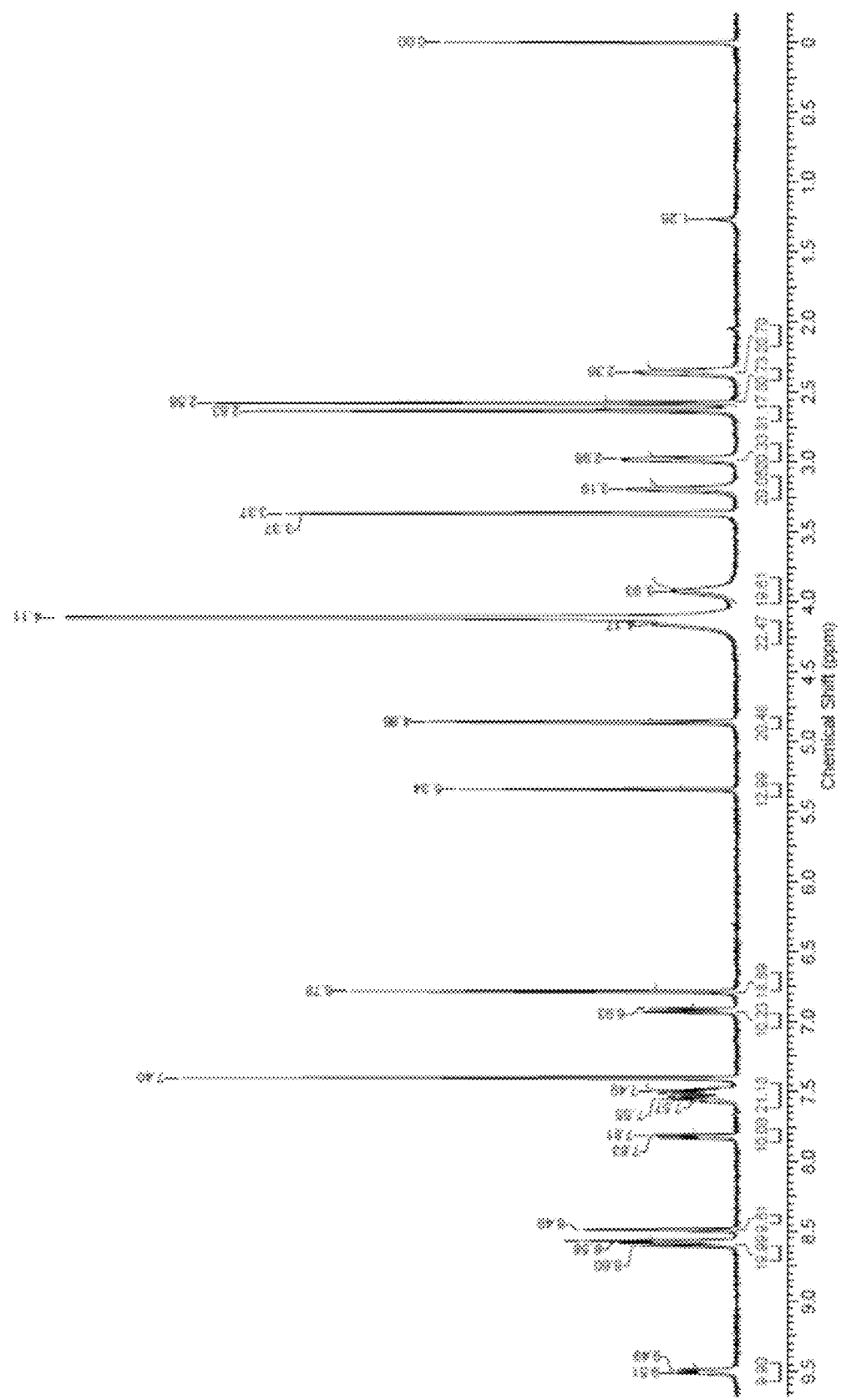
FIG. 33 is a $^1$H NMR spectrum of fumaric acid salt of Compound I.
Figure 34:
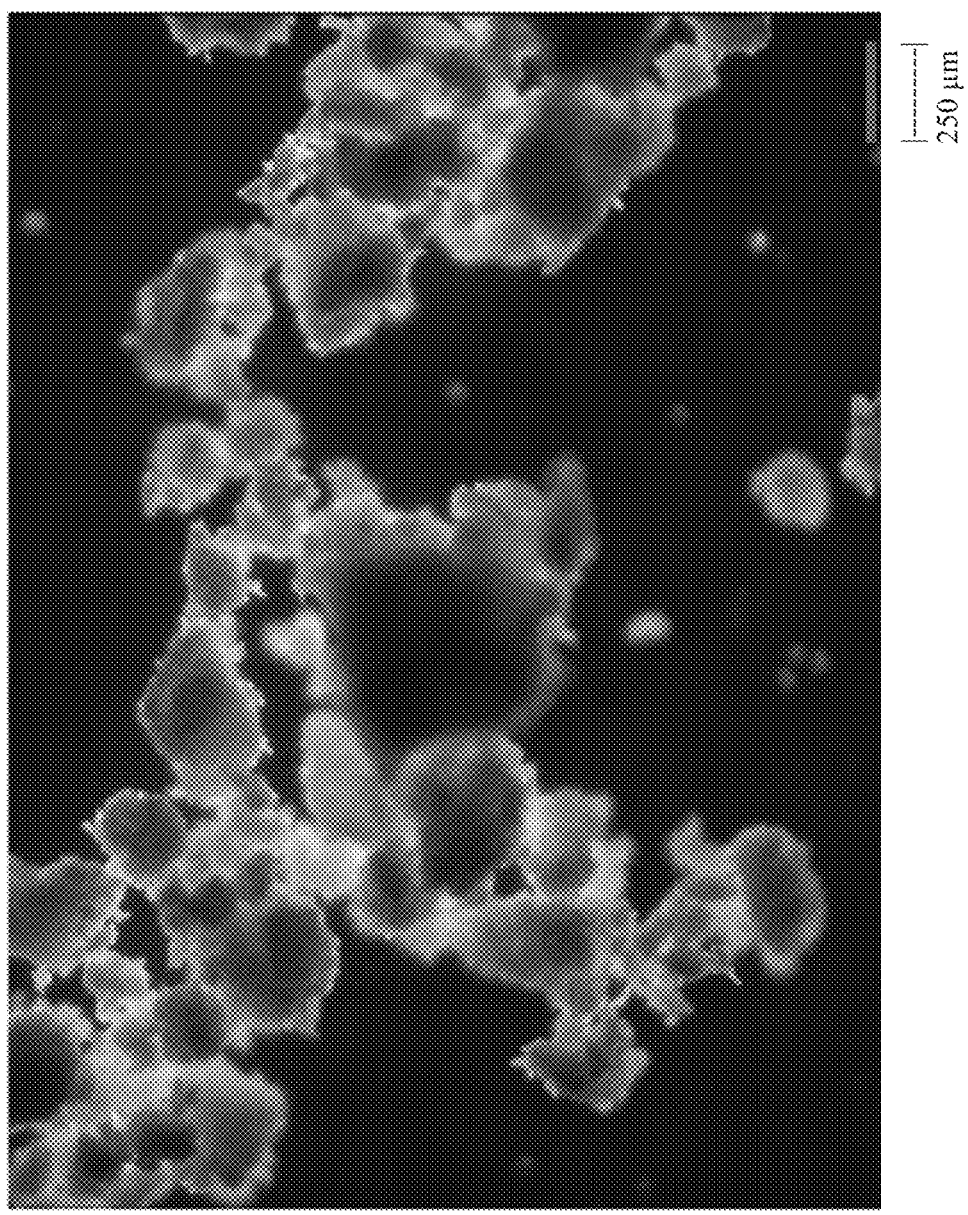
FIG. 34 is a microscopy picture of fumaric acid salt of Compound I using polarization filters.

In one embodiment, the crystalline form of a fumaric acid salt of Compound I exhibits a $^1$H NMR spectrum that is substantially similar to FIG. 33. In another embodiment, the crystalline form of a fumaric acid salt of Compound I may consist of small needles that form agglomerates on a macroscopic scale, which may be substantially similar to FIG. 34. In one embodiment, the ratio of fumaric acid and Compound I in the fumaric acid salt of Compound I is about 1:1.

Citric Acid Salt of Compound I

In one embodiment, the crystalline form of a citric acid salt of Compound I exhibits an XRDP comprising peaks at about 4.900, 25.380, and 27.500 degrees two-theta with the margin of error of about ±0.5; about ±0.4; about ±0.3; about ±0.2; about ±0.1; about ±0.05, or less. In another embodiment, the XRDP of the crystalline citric acid salt of Compound I further comprises at least one, two, three, or four peaks at about 15.360, 18.100, 19.300, and 26.140 degrees two-theta with the margin of error of about ±0.5; about ±0.4; about ±0.3; about ±0.2; about ±0.1; about ±0.05; or less. In another embodiment, the XRDP of the crystalline citric acid salt of Compound I further comprises at least one, two, three, or four peaks at about 17.400, 18.680, 24.040, and 26.740 degrees two-theta with the margin of error of about ±0.5; about ±0.4; about ±0.3; about ±0.2; about ±0.1; about ±0.05; or less. In yet another embodiment, the crystalline form of a citric acid salt of Compound I exhibits an XRDP comprising peaks shown in the table below:

TABLE 9

XRDP Table of a Citric Acid Salt of Compound I

| 2Theta | Flex Width | d-value | Intensity | I/Io |
|--------|------------|---------|-----------|------|
| 4.900  | 0.235      | 18.0193 | 1520      | 68   |
| 5.860  | 0.518      | 15.0693 | 606       | 28   |
| 9.560  | 0.212      | 9.2437  | 438       | 20   |
| 11.080 | 0.235      | 7.9788  | 898       | 41   |
| 12.820 | 0.235      | 6.8995  | 446       | 20   |
| 13.280 | 0.306      | 6.6616  | 506       | 23   |
| 14.480 | 0.188      | 6.1121  | 440       | 20   |
| 15.360 | 0.282      | 5.7638  | 1215      | 55   |
| 15.920 | 0.329      | 5.5623  | 585       | 27   |
| 16.200 | 0.165      | 5.4668  | 509       | 23   |
| 17.400 | 0.259      | 5.0924  | 1088      | 49   |
| 18.100 | 0.259      | 4.8970  | 1158      | 52   |
| 18.680 | 0.353      | 4.7462  | 984       | 44   |
| 19.300 | 0.282      | 4.5952  | 1209      | 55   |
| 19.700 | 0.235      | 4.5027  | 728       | 33   |
| 20.120 | 0.188      | 4.4097  | 740       | 34   |
| 20.380 | 0.306      | 4.3540  | 796       | 36   |
| 20.960 | 0.306      | 4.2348  | 649       | 30   |
| 21.380 | 0.212      | 4.1526  | 724       | 33   |
| 21.700 | 0.212      | 4.0920  | 654       | 30   |
| 22.120 | 0.212      | 4.0153  | 577       | 26   |
| 22.520 | 0.188      | 3.9449  | 607       | 28   |
| 23.140 | 0.259      | 3.8406  | 796       | 36   |
| 23.360 | 0.165      | 3.8049  | 706       | 32   |
| 24.040 | 0.306      | 3.6988  | 1055      | 48   |
| 24.580 | 0.282      | 3.6187  | 781       | 35   |
| 25.380 | 0.259      | 3.5064  | 2237      | 100  |
| 26.140 | 0.376      | 3.4062  | 1137      | 51   |
| 26.740 | 0.282      | 3.3311  | 1024      | 46   |
| 27.500 | 0.306      | 3.2408  | 2149      | 97   |
| 28.040 | 0.212      | 3.1796  | 620       | 28   |
| 28.540 | 0.188      | 3.1250  | 573       | 26   |
| 28.920 | 0.235      | 3.0848  | 616       | 28   |
| 30.280 | 0.471      | 2.9493  | 634       | 29   |

Figure 36:
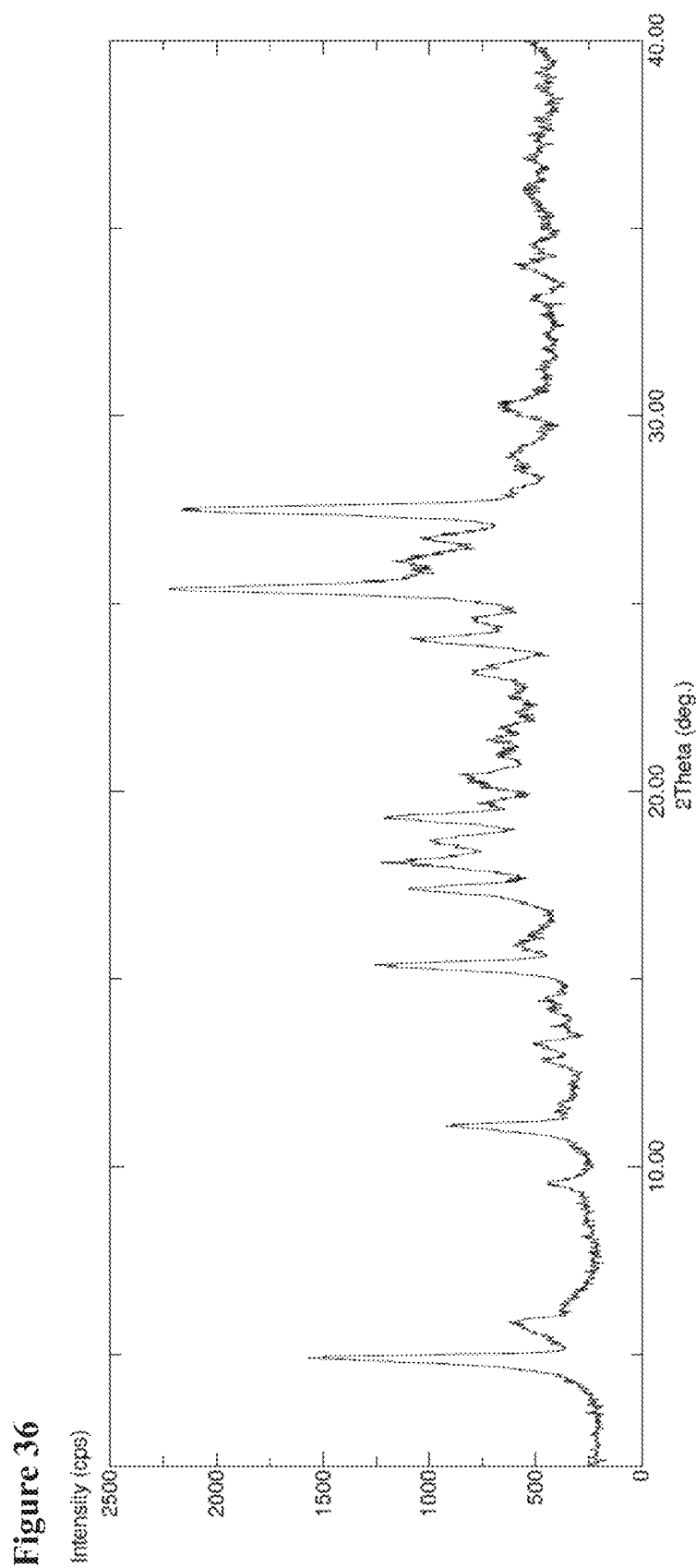
FIG. 36 is a graph of an XRPD pattern of citric acid salt of Compound I.

In one specific embodiment, the crystalline form of a citric acid salt of Compound I exhibits an XRDP that is substantially similar to FIG. 36.

Figure 37:
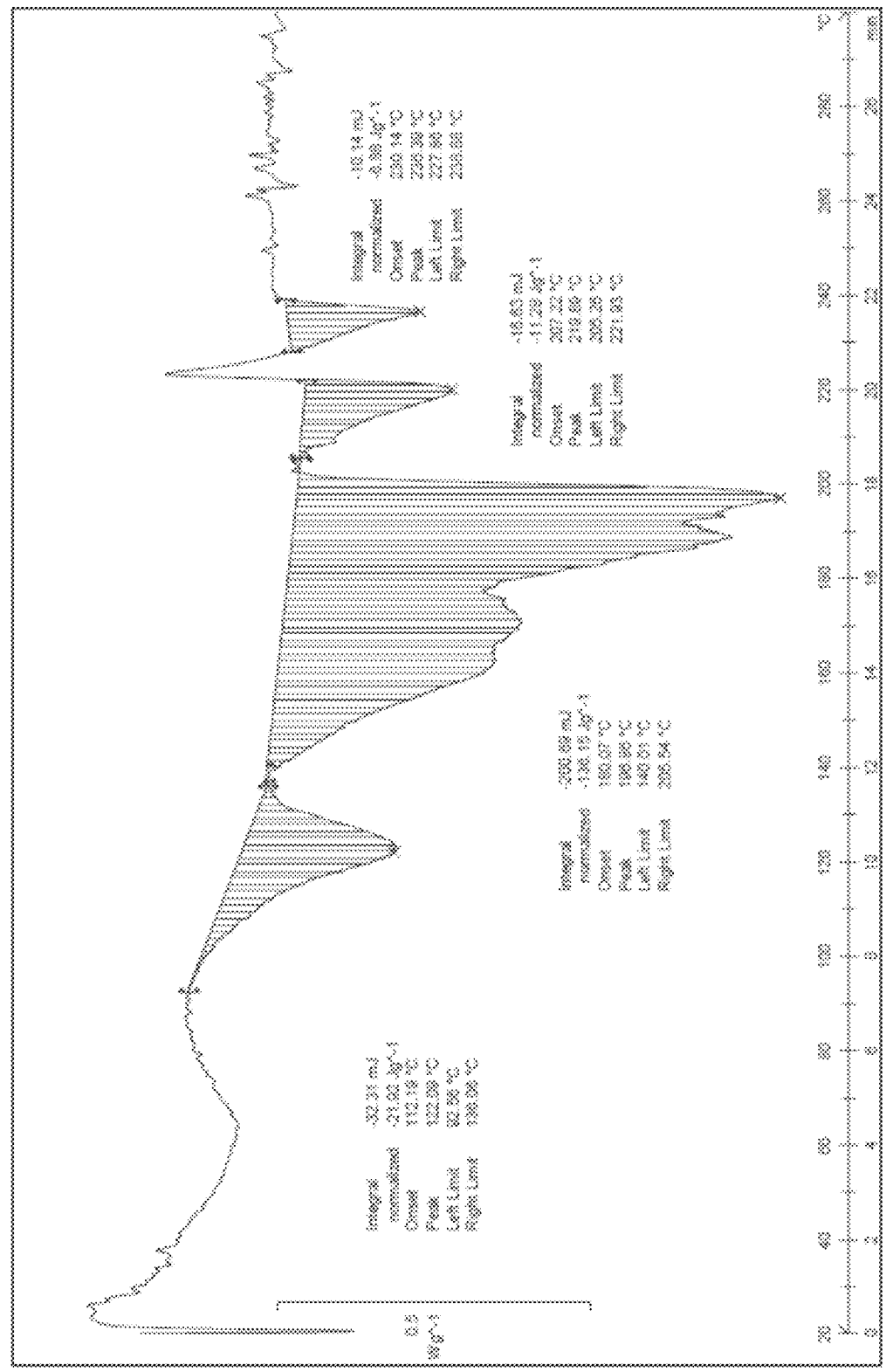
FIG. 37 is a DSC thermogram of citric acid salt of Compound I.

In one embodiment, the crystalline form of a citric acid salt of Compound I exhibits a DSC thermogram comprising a peak characteristic value at about 196.86° C. with the error of margin of about ±2.5; about ±2.0; about ±1.5; about ±1.0; about ±0.5; or less. In one specific embodiment, the crystalline form of a citric acid salt of Compound I exhibits a DSC thermogram that is substantially similar to FIG. 37.

Figure 38:
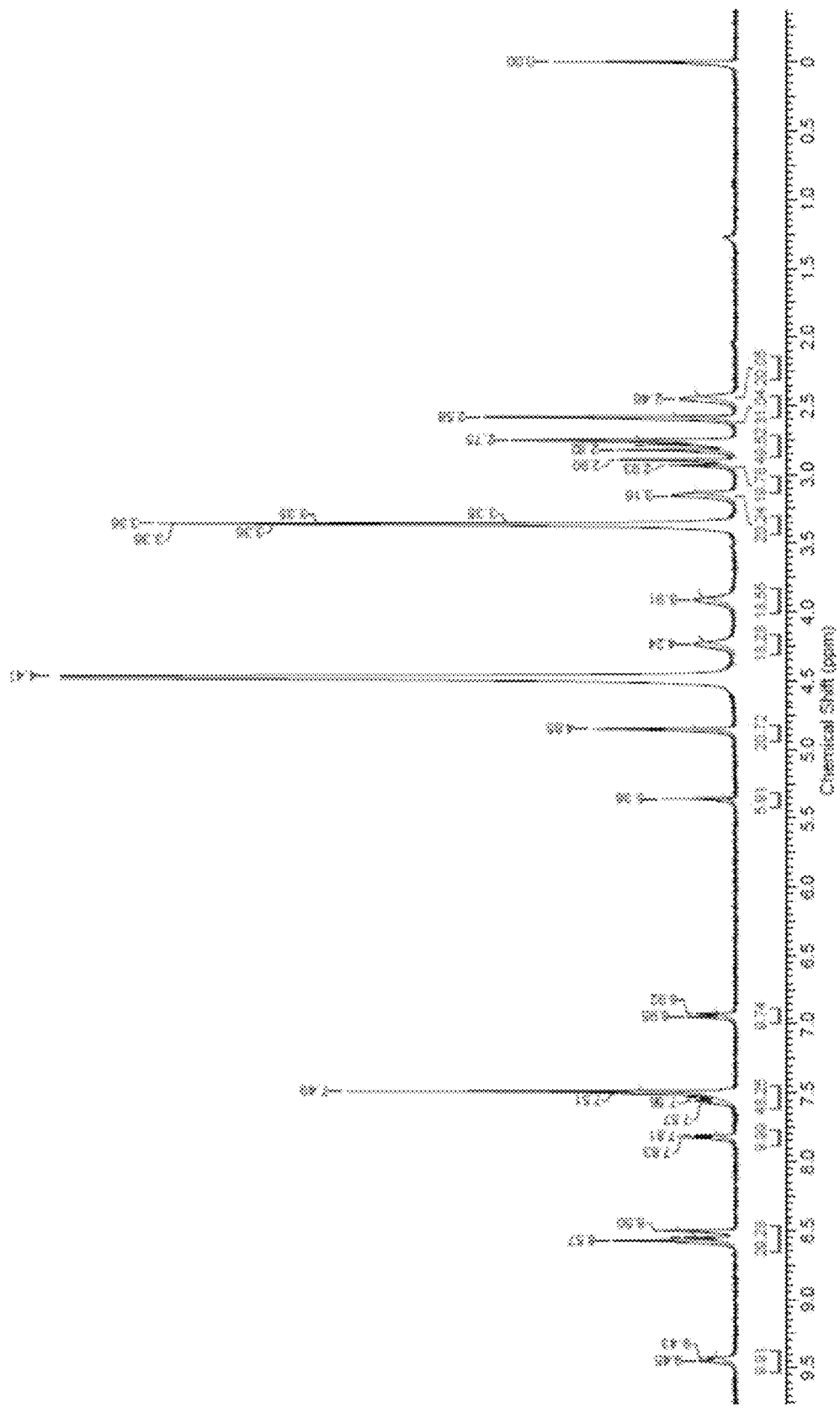
FIG. 38 is a $^1$H NMR spectrum of citric acid salt of Compound I.
Figure 39:
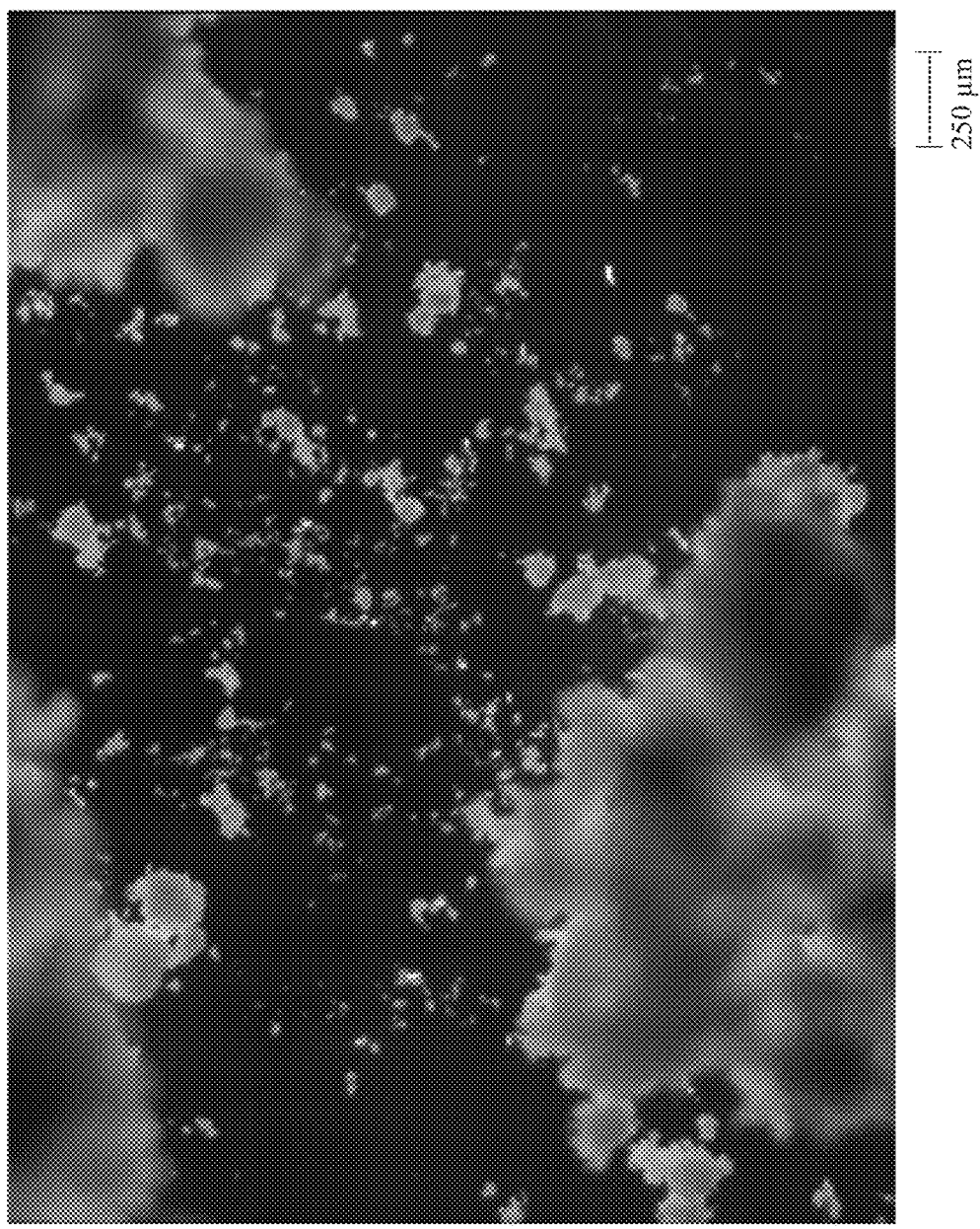
FIG. 39 is a microscopy picture of citric acid salt of Compound I using polarization filters.

In one embodiment, the crystalline form of a citric acid salt of Compound I exhibits a $^1$H NMR spectrum that is substantially similar to FIG. 38. In another embodiment, the crystalline form of a citric acid salt of Compound I may consist of small needles that form agglomerates on a macroscopic scale, which may be substantially similar to FIG. 39. In one embodiment, the ratio of citric acid and Compound I in the citric acid salt of Compound I is about 1:1.

L-Malic Acid Salt of Compound I

In one embodiment, the crystalline form of an L-malic acid salt of Compound I exhibits an XRDP comprising peaks at about 6.580, 6.780, and 25.560 degrees two-theta with the margin of error of about ±0.5; about ±0.4; about ±0.3; about ±0.2; about ±0.1; about ±0.05; or less. In another embodiment, the XRDP of the crystalline L-malic acid salt of Compound I further comprises one, two, three, or four peaks selected from at about 19.560, 23.660, 26.060, and 26.960 degrees two-theta with the margin of error of about ±0.7; about ±0.6; about ±0.5; about ±0.4; about ±0.3; about ±0.2; about ±0.1; about ±0.05; or less. In another embodiment, the XRDP of the crystalline L-malic acid salt of Compound I further comprises one, two, three, four or five peaks selected from at about 8.800, 11.800, 18.600, 24.460, and 25.080 degrees two-theta with the margin of error of about ±0.5; about ±0.4; about ±0.3; about ±0.2; about ±0.1; about 10.05; or less.

In yet another embodiment, the crystalline form of an L-malic add salt of Compound I exhibits an XRDP comprising peaks shown in the table below:

TABLE 10

XRDP Table of an L-Malic Acid Salt of Compound I

| 2Theta | Flex Width | d-value | Intensity | I/Io |
|---|---|---|---|---|
| 6.580 | 0.188 | 13.4219 | 1468 | 78 |
| 6.780 | 0.212 | 13.0264 | 1476 | 79 |
| 8.800 | 0.259 | 10.0403 | 959 | 51 |
| 11.800 | 0.259 | 7.4935 | 965 | 52 |
| 13.040 | 0.259 | 6.7836 | 565 | 31 |
| 14.200 | ***** | 6.2320 | 426 | 23 |
| 15.080 | 0.329 | 5.8702 | 561 | 30 |
| 15.940 | 0.353 | 5.5554 | 766 | 41 |
| 16.800 | 0.376 | 5.2729 | 617 | 33 |
| 17.240 | 0.259 | 5.1393 | 675 | 36 |
| 17.660 | 0.165 | 5.0180 | 768 | 41 |
| 18.080 | 0.282 | 4.9024 | 812 | 44 |
| 18.600 | 0.259 | 4.7665 | 963 | 52 |
| 19.560 | 0.329 | 4.5347 | 1207 | 65 |
| 20.160 | 0.165 | 4.4010 | 725 | 39 |
| 20.580 | 0.188 | 4.3121 | 687 | 37 |
| 21.360 | 0.212 | 4.1564 | 539 | 29 |
| 22.020 | 0.212 | 4.0333 | 500 | 27 |
| 22.860 | 0.424 | 3.8870 | 728 | 39 |
| 23.660 | 0.329 | 3.7573 | 1135 | 61 |
| 24.460 | 0.424 | 3.6362 | 1059 | 57 |
| 25.080 | 0.212 | 3.5477 | 1018 | 55 |
| 25.560 | 0.353 | 3.4822 | 1882 | 100 |
| 26.060 | ***** | 3.4165 | 1148 | 61 |
| 26.960 | 0.612 | 3.3044 | 1167 | 63 |
| 27.660 | 0.188 | 3.2224 | 734 | 40 |
| 28.080 | 0.329 | 3.1751 | 785 | 42 |
| 28.740 | 0.353 | 3.1037 | 636 | 34 |
| 29.840 | 0.353 | 2.9917 | 591 | 32 |
| 30.780 | ***** | 2.9025 | 508 | 27 |
| 31.660 | 0.212 | 2.8238 | 553 | 30 |
| 31.900 | 0.188 | 2.8031 | 534 | 29 |

Figure 41:
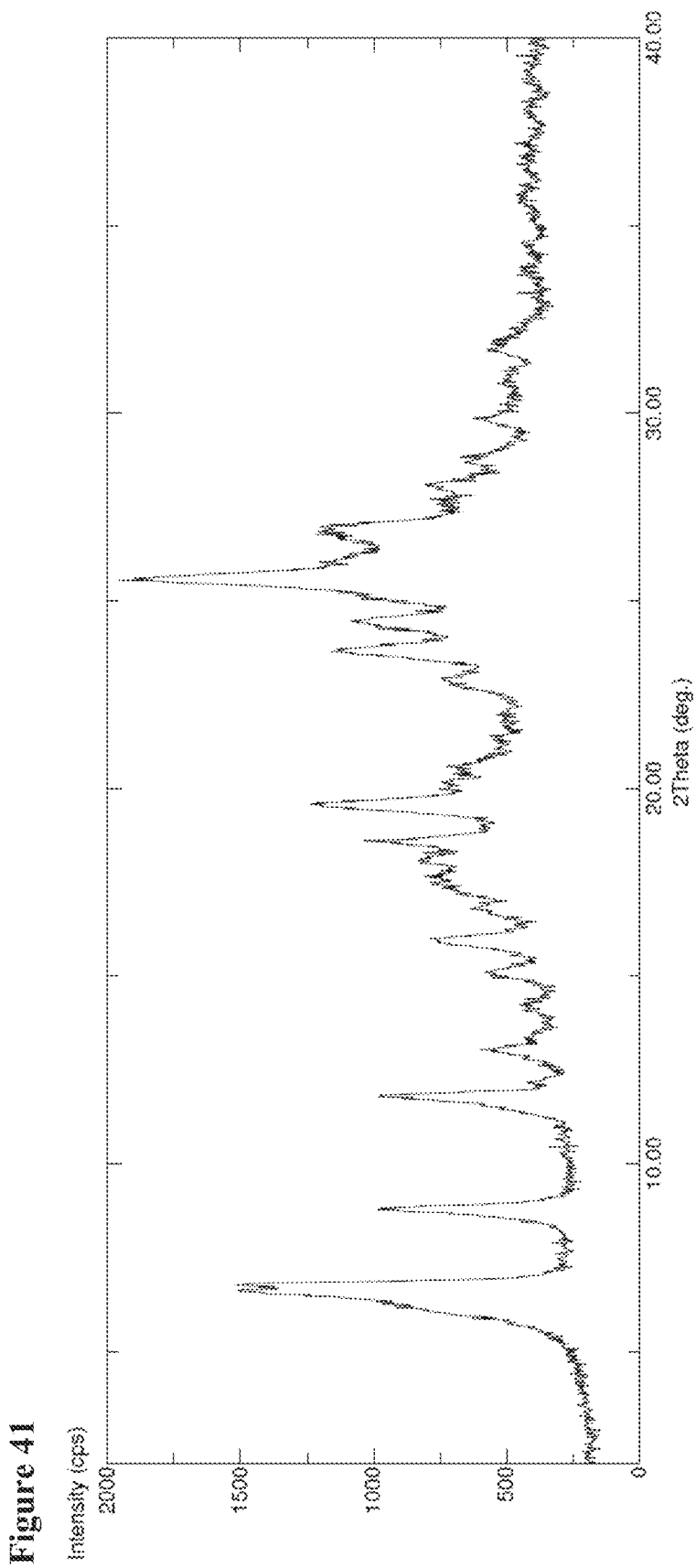
FIG. 41 is a graph of an XRPD pattern of L-malic acid salt of Compound I.

In one specific embodiment, the crystalline form of an L-malic acid salt of Compound I exhibits an XRDP that is substantially similar to FIG. 41.

Figure 42:
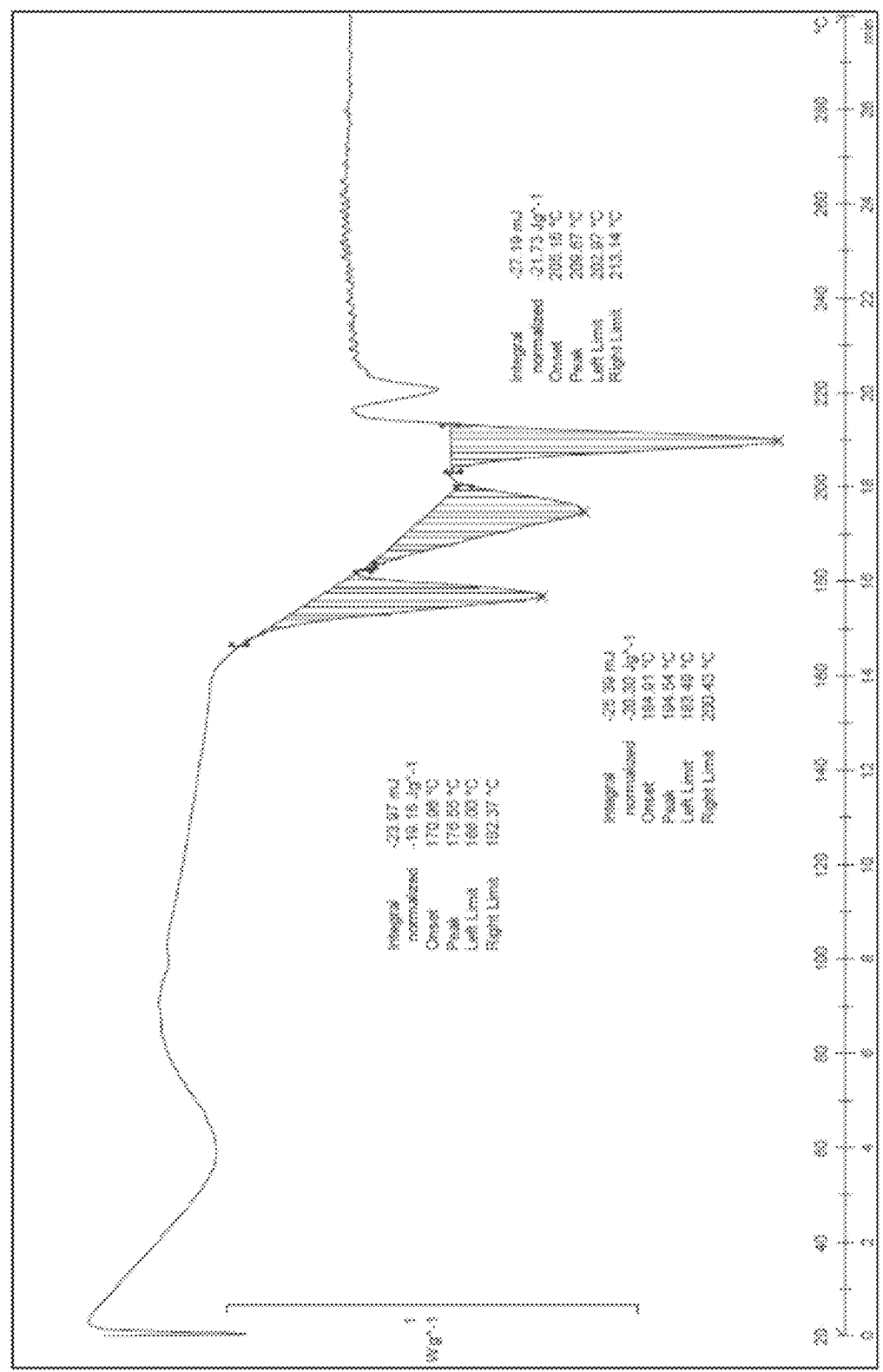
FIG. 42 is a DSC thermogram of L-malic acid salt of Compound I.

In one embodiment, the crystalline form of an L-malic acid salt of Compound I exhibits a DSC thermogram comprising a peak characteristic value at about 209.67° C. with the error of margin of about ±2.5; about ±2.0; about ±1.5; about ±1.0; about ±0.5; or less. In one specific embodiment, the crystalline form of an L-malic acid salt of Compound I exhibits a DSC thermogram that is substantially similar to FIG. 42.

Figure 43:
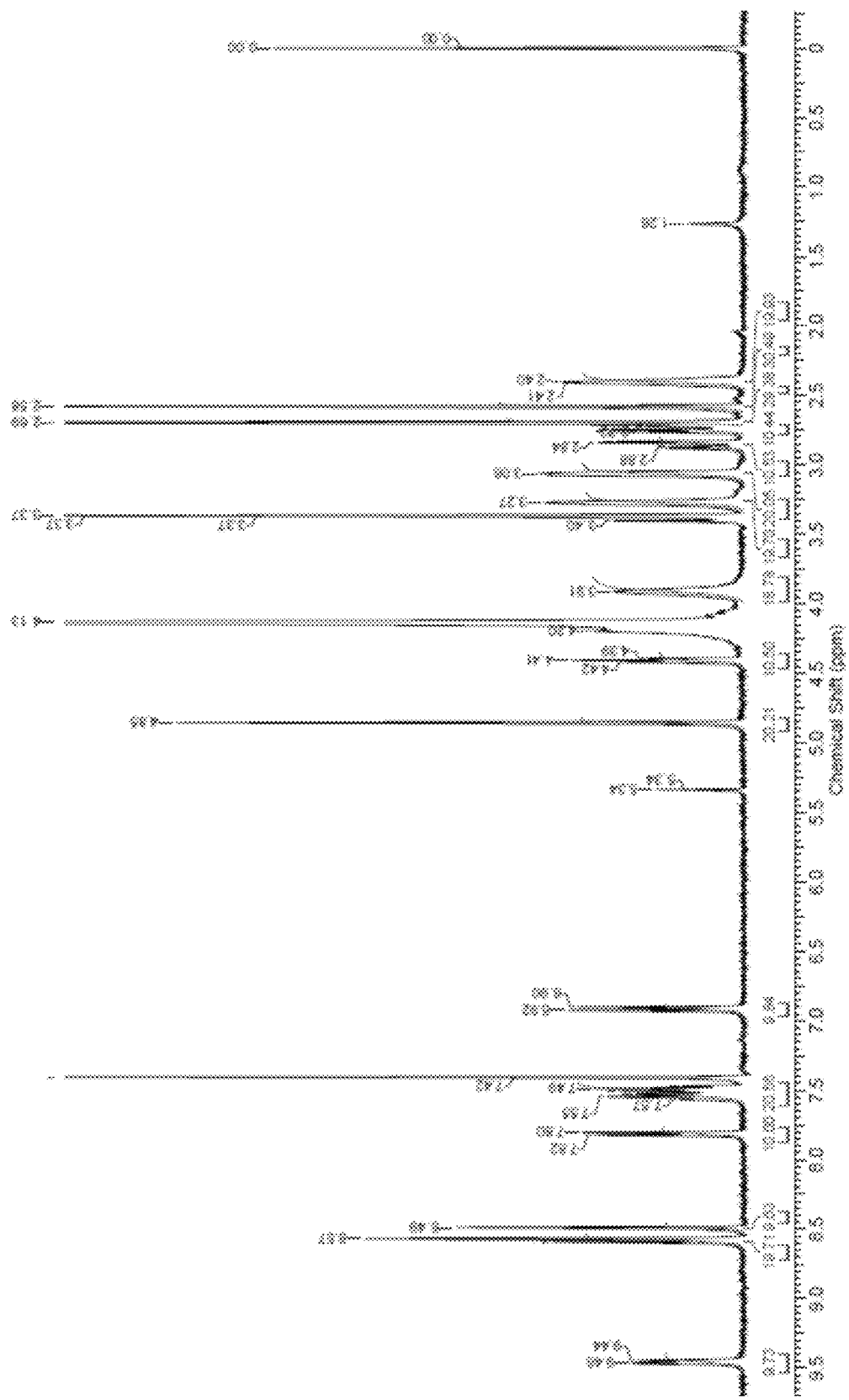
FIG. 43 is a $^1$H NMR spectrum of L-malic acid salt of Compound I.
Figure 44:
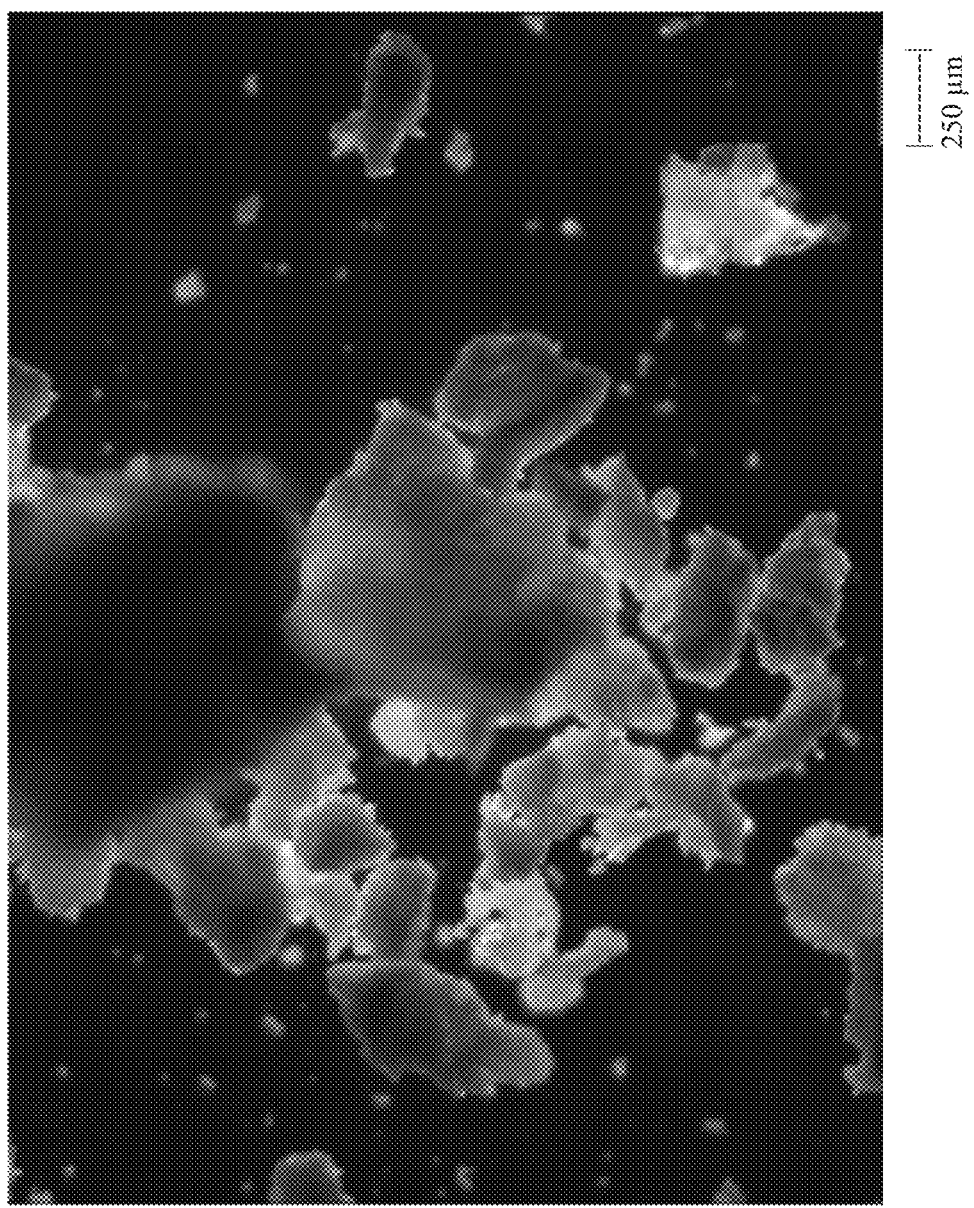
FIG. 44 is a microscopy picture of L-malic acid salt of Compound I using polarization filters.

In one embodiment, the crystalline form of an L-malic acid salt of Compound I exhibits a $^1$H NMR spectrum that is substantially similar to FIG. 43. In another embodiment, the crystalline form of an L-malic acid salt of Compound I may consist of small needles that form agglomerates on a macroscopic scale, which may be substantially similar to FIG. 44. In one embodiment, the ratio of L-malic acid and Compound I in the L-malic acid salt of Compound I is about 1:1.

Pharmaceutical Formulations

In another embodiment, the present invention provides a pharmaceutical composition comprising a therapeutically effective amount of a crystalline form of Compound I, or a pharmaceutically acceptable salt, ester, and/or solvate thereof, as disclosed herein, as the active ingredient, combined with a pharmaceutically acceptable excipient or carrier. The excipients are added to the formulation for a variety of purposes.

Diluents may be added to the formulations of the present invention. Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., liquid glucose, magnesium aluminum silicate, maltodextrin, methyl cellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions may be prepared using the crystalline forms of the present invention and any other solid excipients where the components are dissolved or suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions, aerosols and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting; however, they are not subjected to a final tableting step.

The active ingredient and excipients may be formulated into compositions and dosage forms according to methods known in the art.

In one embodiment, a dosage form may be provided as a kit comprising crystalline form of Compound I and pharmaceutically acceptable excipients and carriers as separate components. In some embodiments, the dosage form kit allow physicians and patients to formulate an oral solution or injection solution prior to use by dissolving, suspending, or mixing the crystalline form of Compound I with pharmaceutically acceptable excipients and carriers. In one embodiment, a dosage form kit which provides crystalline form of Compound I has improved stability of Compound I compared to pre-formulated liquid formulations of Compound I.

It is not necessary that the formulations of the present invention contain only one crystalline form of Compound I. The crystalline forms of the present invention may be used in pharmaceutical formulations or compositions as single components or mixtures together with other crystalline forms of Compound I. In one embodiment, pharmaceutical formulations or compositions of the present invention contain 25-100% or 50-100% by weight, of at least one of crystalline form of Compound I as described herein, in the formulation or composition.

Therapeutic Use

The present invention also provides treatment of disorders related to proliferation of cells. In one aspect, there is provided a method for selectively activating p53 protein comprising contacting a cell afflicted by disorder related to cell proliferation with the present compound. In one embodiment, the method comprises contacting cancer and/or tumor cells with the crystalline form of Compound I, or a pharmaceutically acceptable salt, ester, and/or solvate thereof, as disclosed herein. In another embodiment, the method of contacting cancer and/or tumor cells with the crystalline form of Compound I, or a pharmaceutically acceptable salt, ester, and/or solvate thereof, as disclosed herein, may induce cell apoptosis or alleviate or prevent the progression of the disorder.

Additionally, disclosed are methods for treating cancers, cancer cells, tumors, or tumor cells. Non limiting examples of cancer that may be treated by the methods of this disclosure include cancer or cancer cells of: colorectum, breast, lung, liver, pancreas, lymph node, colon, prostate, brain, head and neck, skin, ovary, cervical, thyroid, bladder, kidney, and blood and heart (e.g., leukemia, lymphoma, and carcinoma). Non limiting examples of tumors that may be treated by the methods of this disclosure include tumors and tumor cells of: colorectum, breast, lung, liver, pancreas, lymph node, colon, prostate, brain, head and neck, skin, kidney, and blood and heart (e.g., leukemia, lymphoma, and carcinoma).

The present invention also provides methods of treating, preventing, ameliorating and/or alleviating the progression of disorders or conditions characterized by cell proliferation in a subject. More particularly, the methods of the present invention involve administration of an effective amount of the crystalline form of the quinolone compounds described herein, in a subject to treat a disorder or a condition characterized by cell proliferation. The crystalline form can be administered in an amount effective selectively activate p53 proteins in cancer and/or tumor cells, which may lead to cell death or apoptosis. The terms "subject" and "patient" are used interchangeably throughout the present application.

As used herein, administering can be effected or performed using any of the various methods known to those skilled in the art. The crystalline form can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed crystalline forms can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the crystalline form is administered (e.g., syrup, elixir, capsule, tablet, foams, emulsion, gel, etc.) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The crystalline form can also be used to coat bioimplantable materials to enhance neurite outgrowth, neural survival, or cellular interaction with the implant surface.

The crystalline forms disclosed herein can be administered together with other biologically active agents, such as anti-cancer agents, analgesics, anti-inflammatory agents, anesthetics and other agents which can control one or more symptoms or causes of a disorder or a condition characterized by cell proliferation.

In one embodiment, the crystalline form of Compound I, or the crystalline form of pharmaceutically acceptable salt, ester, and/or solvate of Compound I, as disclosed herein, can be administered in combination with one or more therapeutically active agent. In one embodiment, the one or more therapeutically active agent is an anticancer agent. In some embodiments, the one or more therapeutically active anticancer agents include, but are not limited to, paclitaxel, vinblastine, vincristine, etoposide, doxorubicin, herceptin, lapatinib, gefitinib, erlotinib, tamoxifen, fulvestrant, anastrazole, lectrozole, exemestane, fadrozole, cyclophosphamide, taxotere, melphalan, chlorambucil, mechlorethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin, C Bleomycin, combinations thereof, and the like. In another embodiment, the one or more therapeutically active anticancer agents include, but are not limited to, PARP (poly (DP-ribose)polymerase) inhibitors. Suitable PARP inhibitors include, but are not limited to, 4-(3-(1-(cyclopropanecarbonyl)piperazine-4-carbonyl)-4-fluorobenzyl)phthalazin-1(2H)-one (olaparib, AZD2281, Ku-0059436), 2-[(2R)-2-methylpyrrolidin-2-yl]-1H-benzimidazole-4-carboxamide (Veliparib, ABT-888), (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (talazoparib, BMN 673), 4-iodo-3-nitrobenzamide (iniparib, BSI-201), 8-fluoro-5-(4-((methylamino)methyl)phenyl)-3,4-dihydro-2H-azepino[5,4,3-cd]indol-1(6H)-one phosphoric acid (Rucaparib, AG-014699, PF-01367338), 2-[4-[(dimethylamino)methyl]phenyl]-5,6-dihydroimidazo[4,5,1-jk][1,4]benzodiazepin-7(4H)-one (AG14361), 3-aminobenzamide (INO-1001), 2-(2-fluoro-4-((S)-pyrrolidin-2-yl)phenyl)-3H-benzo[d]imidazole-4-carboxamide (A-966492), N-(5,6-dihydro-6-oxo-2-phenanthridinyl)-2-acetamide hydrochloride (PJ34, PJ34 HCl), MK-4827, 3,4-dihydro-4-oxo-3,4-dihydro-4-oxo-N-[(1S)-1-phenylethyl]-2-quinazolinepropanamide (NM 0328), 5-(2-oxo-2-phenyl ethoxy)-1(2H)-isoquinolinone (UPF-1069), 4-[[4-fluoro-3-[(4-methoxy-1-piperidinyl)carbonyl]phenyl]methyl]-1(2H)-phthalazinone (AZD 2461), and the like. In another embodiment, the one or more therapeutically active agent is an immunotherapeutic agent. In some embodiments, the one or more immunotherapeutic agents includes, but are not limited to, a monoclonal antibody, an immune effector cell, adoptive cell transfer, an immunotoxin, a vaccine, a cytokine, and the like.

In another embodiment, the crystalline form of Compound I, or the crystalline form of pharmaceutically acceptable salt, ester, and/or solvate of Compound I, as disclosed herein, can be administered in combination with radiotherapy.

Additionally, administration can comprise administering to the subject a plurality of dosages over a suitable period of time. Such administration regimens can be determined according to routine methods, upon a review of the instant disclosure.

Crystalline forms of the invention are generally administered in a dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. Time release preparations may be employed or the dose may be administered in as many divided doses as is convenient. When other methods are used (e.g. intravenous administration), crystalline forms are administered to the affected tissue at a rate from about 0.05 to about 10 mg/kg/hour, alternately from about 0.1 to about 1 mg/kg/hour. Such rates are easily maintained when these crystalline forms are intravenously administered as discussed herein. Generally, topically administered formulations are administered in a dose of about 0.5 mg/kg/dose to about 10 mg/kg/dose range. Alternately, topical formulations are administered at a dose of about 1 mg/kg/dose to about 7.5 mg/kg/dose or even about 1 mg/kg/dose to about 5 mg/kg/dose.

A range of from about 0.1 to about 100 mg/kg is appropriate for a single dose. Continuous administration is appropriate in the range of about 0.05 to about 10 mg/kg.

Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) Cancer Chemother Rep. 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m$^2$.

A dosage form of the present invention may contain Compound I, or a pharmaceutically acceptable salt, ester, and/or solvate thereof, as disclosed herein, in an amount of about 5 mg to about 500 mg. That is, a dosage form of the present invention may contain Compound I in an amount of about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, or 500 mg. In one embodiment, such dosage amount is administered to a patient as a daily dose either in a single dose or in divided portions served multiple times a day, such as twice, three times, or four times a day.

A dosage form of the present invention may be administered, hourly, daily, weekly, or monthly. The dosage form of the present invention may be administered twice a day or once a day. The dosage form of the present invention may be administered with food or without food.

Insofar as the crystalline forms disclosed herein can take the form of a mimetic or fragment thereof, it is to be appreciated that the potency, and therefore dosage of an effective amount can vary. However, one skilled in the art can readily assess the potency of a crystalline form of the type presently envisioned by the present application.

In settings of a gradually progressive disorder or condition characterized by cell proliferation, crystalline forms of the present application are generally administered on an ongoing basis. In certain settings administration of a crystalline form disclosed herein can commence prior to the development of disease symptoms as part of a strategy to delay or prevent the disease. In other settings a crystalline form disclosed herein is administered after the onset of disease symptoms as part of a strategy to slow or reverse the disease process and/or part of a strategy to improve cellular function and reduce symptoms.

It will be appreciated by one of skill in the art that dosage range will depend on the particular crystalline form, and its potency. The dosage range is understood to be large enough to produce the desired effect in which the neurodegenerative or other disorder and the symptoms associated therewith are ameliorated and/or survival of the cells is achieved, but not be so large as to cause unmanageable adverse side effects. It will be understood, however, that the specific dose level for any particular patient will depend on a variety of factors including the activity of the specific crystalline form employed; the age, body weight, general health, sex and diet of the individual being treated; the time and route of administration; the rate of excretion; other drugs which have previously been administered; and the severity of the particular disease undergoing therapy, as is well understood by those skilled in the art. The dosage can also be adjusted by the individual physician in the event of any complication. No unacceptable toxicological effects are expected when crystalline forms disclosed herein are used in accordance with the present application.

An effective amount of the crystalline forms disclosed herein comprise amounts sufficient to produce a measurable biological response. Actual dosage levels of active ingredients in a therapeutic crystalline form of the present application can be varied so as to administer an amount of the active crystalline form that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the present application, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the present application indicate effectiveness with respect to all vertebrate species which are included in the term "subject." In this context, a vertebrate is understood to be any vertebrate species in which treatment of a neurodegenerative disorder is desirable. As used herein, the term "subject" includes both human and animal subjects. Thus, veterinary therapeutic uses are provided in accordance with the present application.

As such, the present application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos or farms. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided are the treatment of livestock, including, but not limited to, domesticated swine, ruminants, ungulates, horses (including race horses), poultry, and the like.

The following examples further illustrate the present invention but should not be construed as in any way limiting its scope.

EXAMPLES

Analytical Methods— various analytical methods, as described below, were applied to the present crystalline forms and their precursors to characterize their physiochemical properties.

Differential Scanning Calorimetry (DSC):

DSC data were collected on DSC-systems (DSC 822e—Mettler Toledo) or on TA Instruments Q2000. In general, samples in the mass range of 1 to 5 mg were placed in a dry aluminum crucible and closed with an aluminum cap with a hole. Generally, the starting temperature was 20° C., the heating rate was 10° C./min, and final temperature was 300° C. using a nitrogen purge flow of 20 mL/min.

Thermogravimetric Analysis (TGA):

TGA data were collected on a TGA 851e apparatus. In general, samples in the mass range of approximately 10 mg were placed in a lean and dry aluminum oxide pan or an aluminum pan. Generally, the sample pan and scanned between −30° C. to about 350° C. at 5° C./minute or at 10° C./minute using a nitrogen purge flow rate at 50 mL/min.

TGA analysis was also performed using a TA Instruments Discovery IR thermogravimetric analyzer. Temperature calibration was performed using nickel and Alumel™. The sample was placed in an aluminum pan. The sample was hermetically sealed, the lid pierced, then inserted into the thermogravimetric furnace. The furnace was heated under nitrogen. The sample was analyzed from ambient to 350° C. with a heating rate of 10° C./min. Trios software v3.1.2.3591 was used to generate thermograms.

$^1$H Nuclear Magnetic Resonance Spectroscopy ($^1$H NMR):

1H NMR spectra was obtained using a Bruker AVANCE 400 MHz instrument in DMSO-$d_6$ or CDCl$_3$ with tetramethylsilane as the internal standard.

Light Microscopy with Hot Stage (HSM):

An Olympus BX41 with Di-Li SMP camera and grab&measure software was used with Hostage Mettler Toledo FP90 with FP 82 heating table. Samples were prepared with brushes onto object holders. Observation was made using unpolarized light or polarized light using two polarization filters at 40, 100, 200 or 400× magnifications. Pictures were taken by software and exported as JPEG, scale is only approximate and not validated.

X-Ray Powder Diffraction (XRPD):

XRPD patterns were obtained using a MiniFlex (Rigaku Corporation) using silicon low background sample holders (diameter 24 mm, pit 0.2 mm). Collection times were nominally 75 minutes. A Cu Kα radiation 1.5406 angstrom source operating at 15 kV was used to irradiate samples. The effective 2θ range was about 2-40° C. and the sampling width was 0.02° C. Samples were ground with mortar and pestle. Solids were positioned on sample holders prepared with grease and flattened with a disc of glass.

HPLC Analysis:

Crystalline forms (i.e., salts and free base) of the present invention were analyzed by total area normalization (TAN).

HPLC Conditions:

HPLC Column: Phenomenex Luna8, 3 μm C18, 4.6×50 mm

Flow Rate: 1.0 mL/min

Injection Volume: 5 μL

Detection: DAD detector, recording at 240 nm

Mobile Phase: A—H$_2$O+0.05% CF$_3$COOH

B—CAN+0.05% CF$_3$COOH

| Gradient Pump Program: | | |
|---|---|---|
| Step Time (minutes) | % A | % B |
| 0.00 | 90.0 | 10.0 |
| 0.10 | 90.0 | 10.0 |
| 10.1 | 10.0 | 90.0 |
| 12.1 | 10.0 | 90.0 |
| 15.0 | 90.0 | 10.0 |

Example 1. Solubility of 2-(4-Methyl-[1,4]diazepan-1-yl)-5-oxo-5H-7-thia-1,11b-diaza-benzo[c]fluorene-6-carboxylic acid (5-methyl-pyrazin-2-ylmethyl)-amide (Compound I, Free Base)

Solubility of Compound I was determined by suspending Compound I in various solvents then heated at an elevated temperature then cooled to room temperature. The mother liquor was sampled and the concentration of Compound I was determined by HPLC.

Example 2. Preparation of Polymorph E of Compound I (Free Base)

Compound I (free base) was dissolved in a solvent mixture to form a solution, which was then concentrated into a suspension. The suspension was then concentrated to dryness. An anti-solvent was added to the suspension, which was concentrated to dryness again. XRPD analysis confirmed formation of polymorph E and revealed polymorph E as crystalline (FIG. 11). The dry content was measured to be 99.97% w/w. $^1$H NMR (FIG. 13) confirmed the structure of this material as the free base of Compound.

Example 3. Preparation of Polymorph A of Compound I (Free Base)

Polymorph E of Compound I (free base) as prepared by Example 2 was suspended in a solvent mixture. The suspension was heated and then cooled down to room temperature. The suspension was filtered, and the resulting filter cake was dried to provide polymorph A. XRPD analysis confirmed formation of polymorph A and revealed polymorph A as crystalline (FIG. 1). The dry content was measured to be 99.86% w/w. $^1$H NMR (FIG. 5) confirmed the structure of this material as the free base of Compound I.

Figure 3:
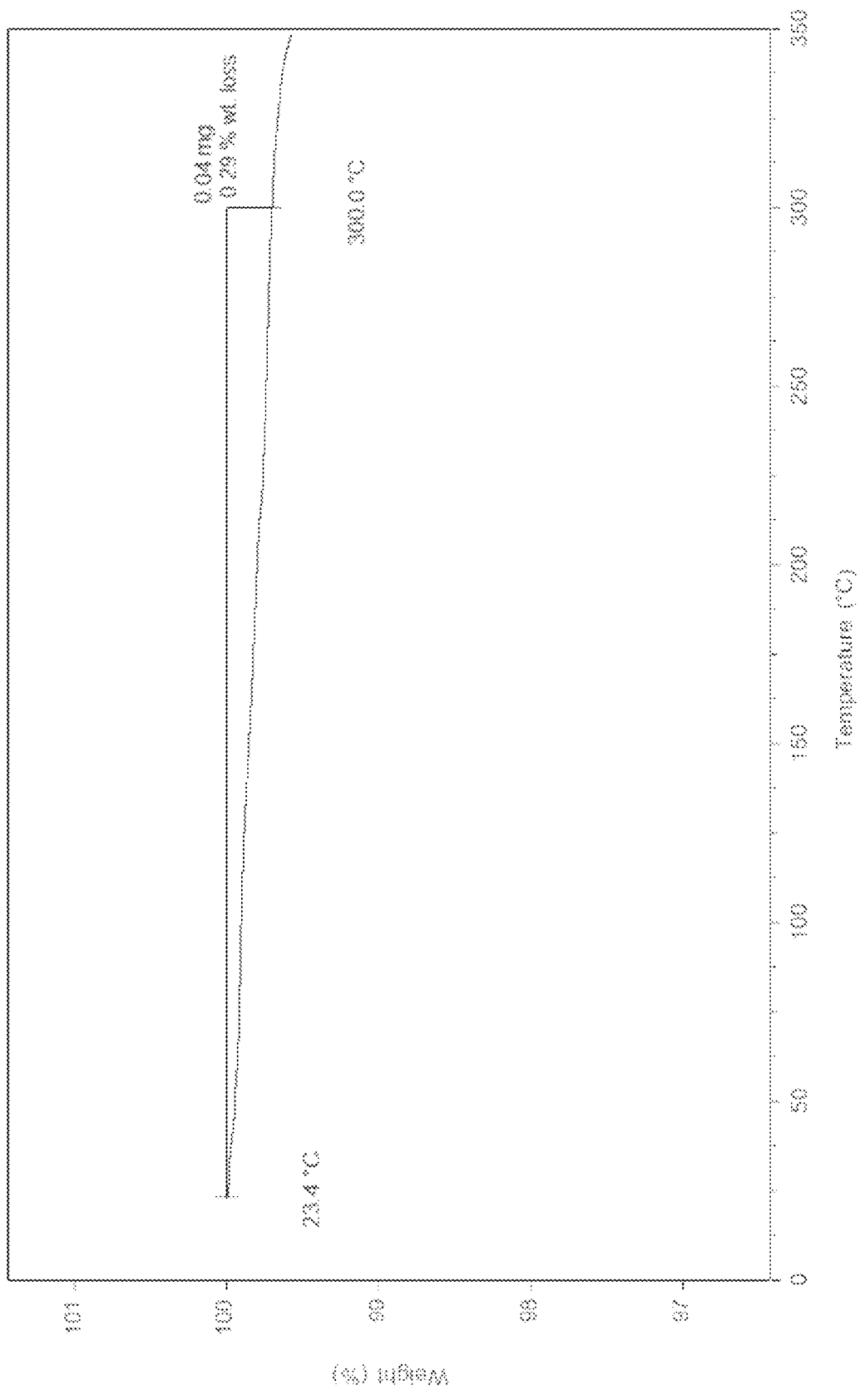
FIG. 3 is a thermogravimetric analysis (TGA) thermogram of polymorph A of Compound I (free base).
Figure 4:
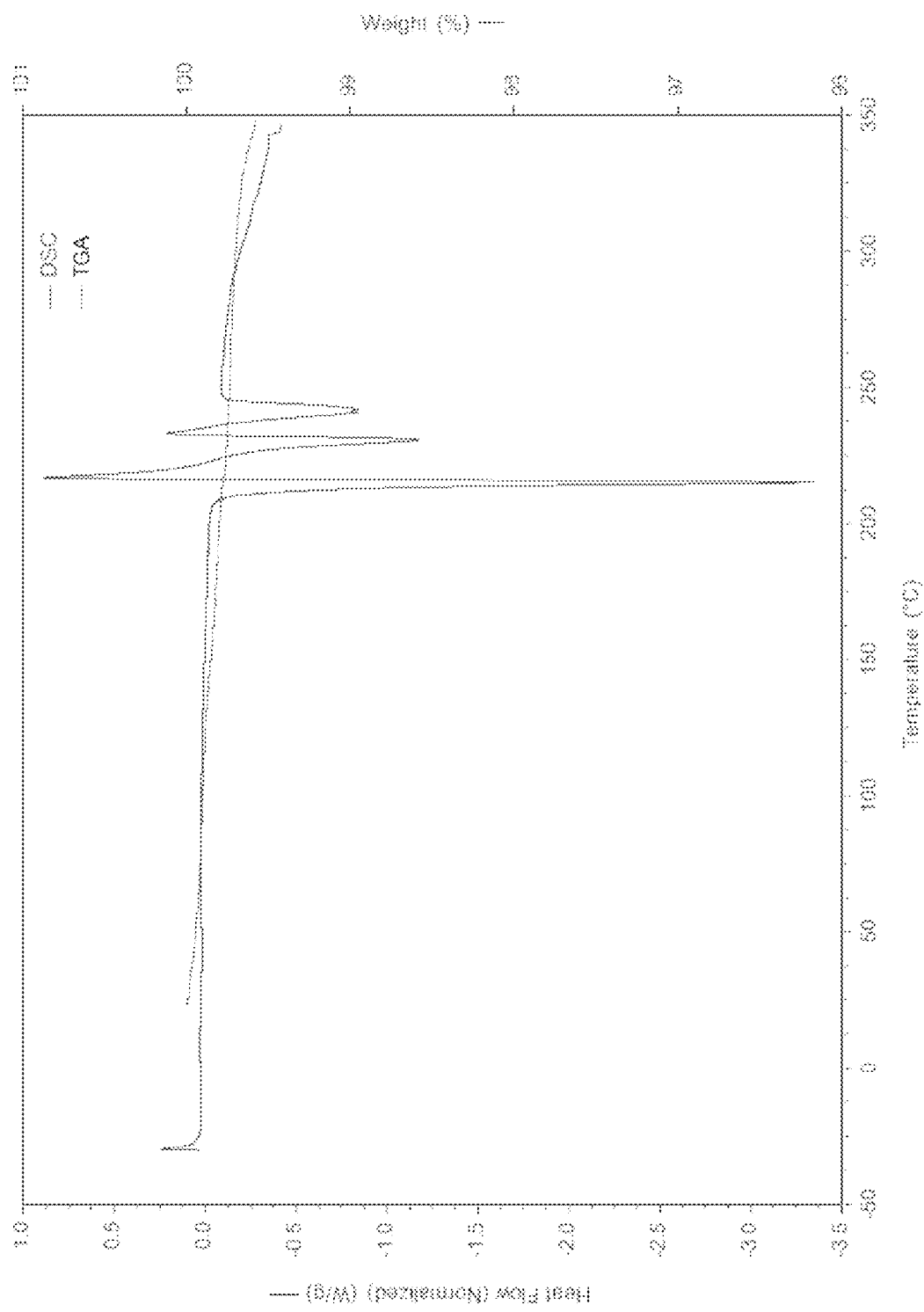
FIG. 4 is an overlay of DSC and TGA thermograms of polymorph A of Compound I (free base).

The DSC thermogram (FIG. 2) exhibits a sharp endotherm at approximately 215° C., followed by an exotherm at approximately 217° C., an endotherm at approximately 231° C., an exotherm at approximately 233° C., and an endotherm at approximately 242° C. Without bound to any theory, these events are consistent with a melt, followed by a recrystallization, another melt and recrystallization, and a final melt event. TGA thermogram (FIG. 3) displays an approximate 0.3% weight loss from ambient to 300° C. FIG. 4 shows an overlay of the DSC and TGA thermograms.

Example 4. Preparation of Polymorph C of Compound I (Free Base)

Polymorph A of Compound I was suspended in an organic solvent at an elevated temperature, filtered and the mother liquor was cooled to form a suspension, which was filtered to obtain white needle like solids. $^1$H NMR (FIG. 9) confirmed the structure of this material as the free base of Compound I.

XRPD analysis revealed polymorph C as crystalline, as shown in FIG. 7.

Example 5. Preparation of Polymorph G of Compound 1 (Free Base)

Polymorph A of Compound I was suspended in another organic solvent at an elevated temperature. The suspension was filtered and the mother liquor was evaporated to form a suspension, which was filtered to obtain slightly yellow solid. $^1$H NMR (FIG. 18) confirmed the structure of this material as the free base of Compound I.

XRPD analysis revealed polymorph G as crystalline, as shown in FIG. 16.

Example 6. Solubility and Stability Test of Polymorph Forms

Solubility of polymorphs A, C, E, and G of Compound I (free base) were determined by suspending approximately 25 mg of each polymorph in organic solvents and the resulting mixtures were stirred at room temperature or elevated temperatures for 1 h. A sample was filtered and the concentration was determined by HPLC. The remaining suspension was evaporated and the solid was analyzed by XRPD to confirm that the polymorph form in the suspension was still the same polymorph form used for the experiment.

Figure 20:
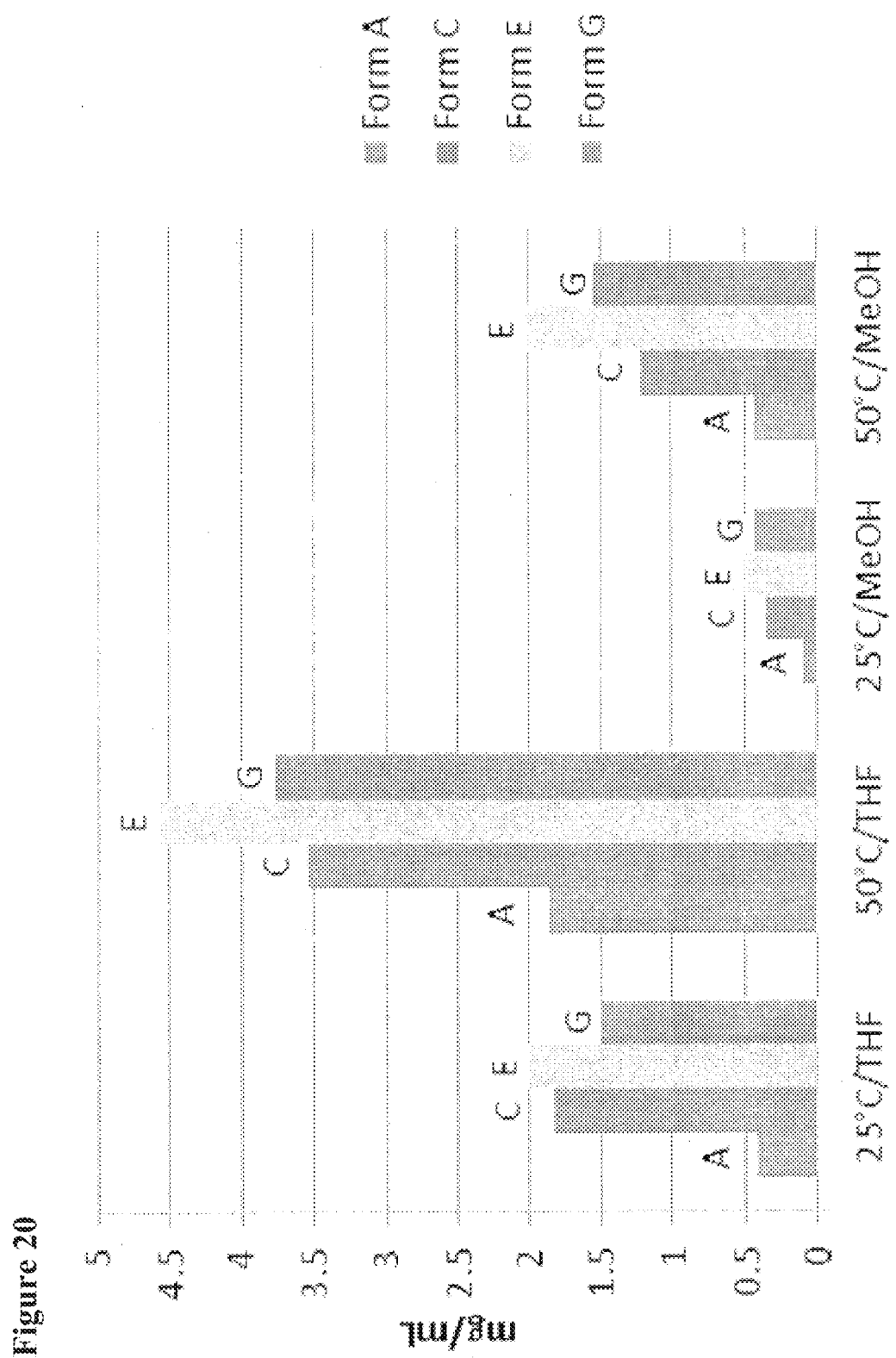
FIG. 20 depicts the solubility of various polymorphs of Compound I (free base) in methanol and THF.

The solubility of each polymorph is shown in FIG. 20. Polymorph A exhibited the lowest solubility, identifying it as the most stable.

Example 7. Preparation of a HCl Salt of Compound I

Figure 25:
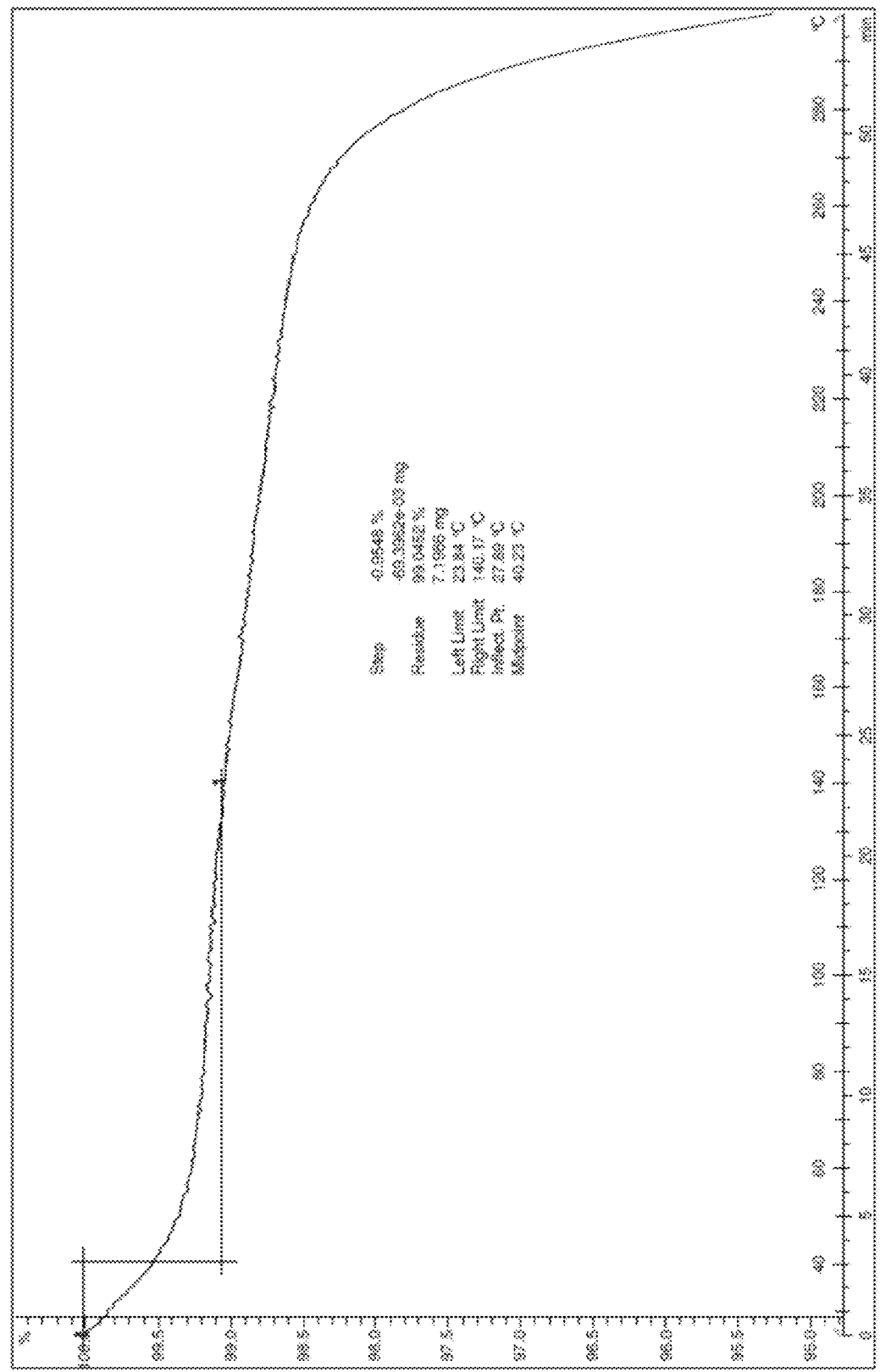
FIG. 25 is a TGA thermogram of HCl salt of Compound I.

Compound I was dissolved in a solvent mixture at an elevated temperature, then HCl was added. The suspension was stirred overnight then filtered and washed to obtain an HCl salt of Compound I as a white powder (62% yield). The resulting salt was characterized by $^1$H NMR (FIG. 23), XRPD (FIG. 21), and TGA (FIG. 25). The TGA showed HCl salt of Compound I demonstrated up to 0.9 wt % loss at 140° C.

Example 8. Preparation of a Maleic Acid Salt of Compound I

Figure 30:
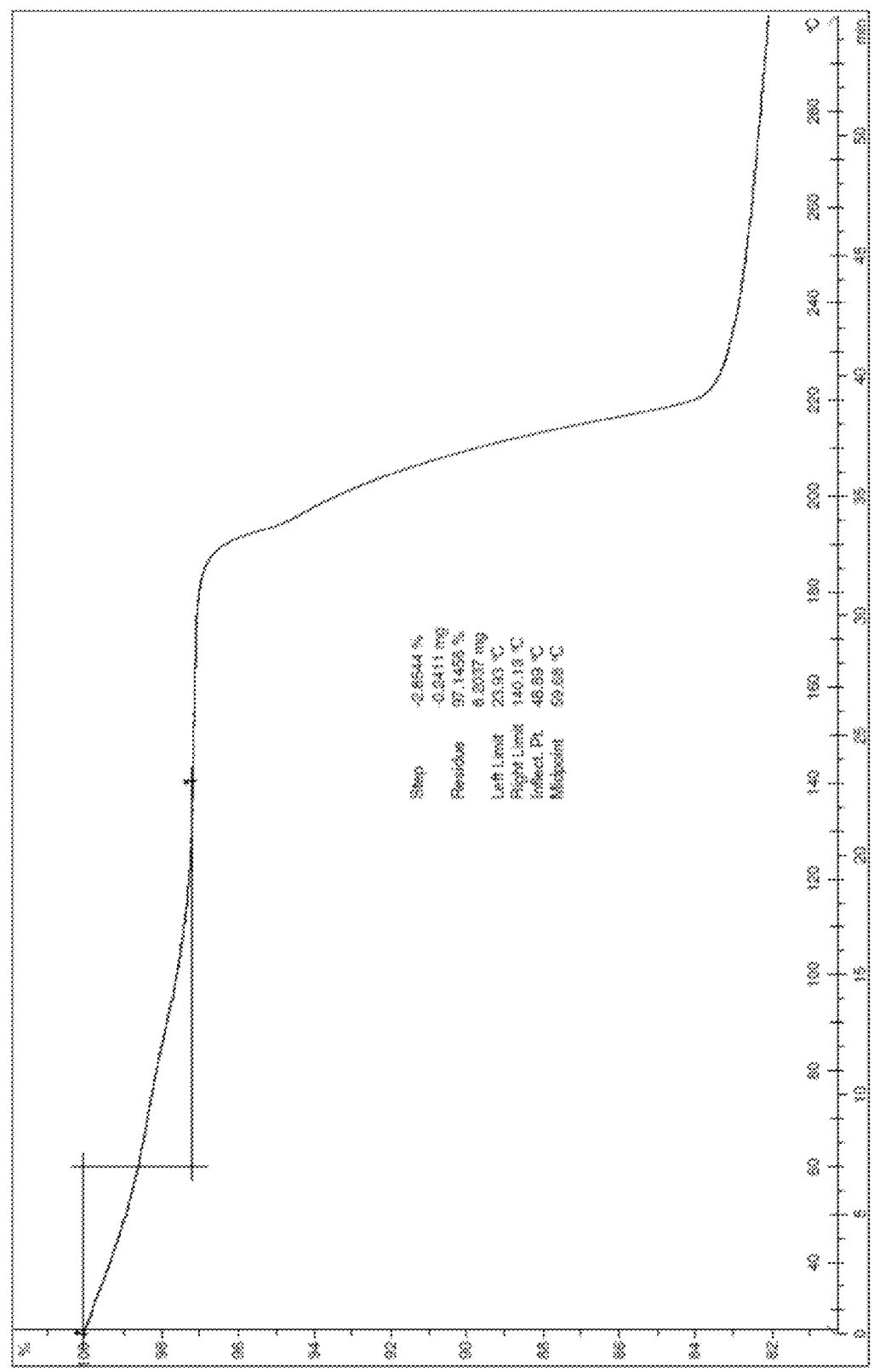
FIG. 30 is a TGA thermogram of maleic acid salt of Compound I.

Compound I was dissolved in a solvent mixture at an elevated temperature, then Maleic acid was added to the mixture. The resulting suspension was cooled and stirred, filtered, and washed to obtain a maleic acid salt of Compound I as a white powder (86% yield). The resulting salt was characterized by $^1$H NMR (FIG. 28), XRPD (FIG. 26), and TGA (FIG. 30). The TGA showed maleic acid salt of Compound I demonstrated up to 2.9 wt % loss at 140° C. Without being bound by any theory, this weight loss may be attributed to solvent loss.

Example 9. Preparation of a Fumaric Acid Salt of Compound I

Figure 35:
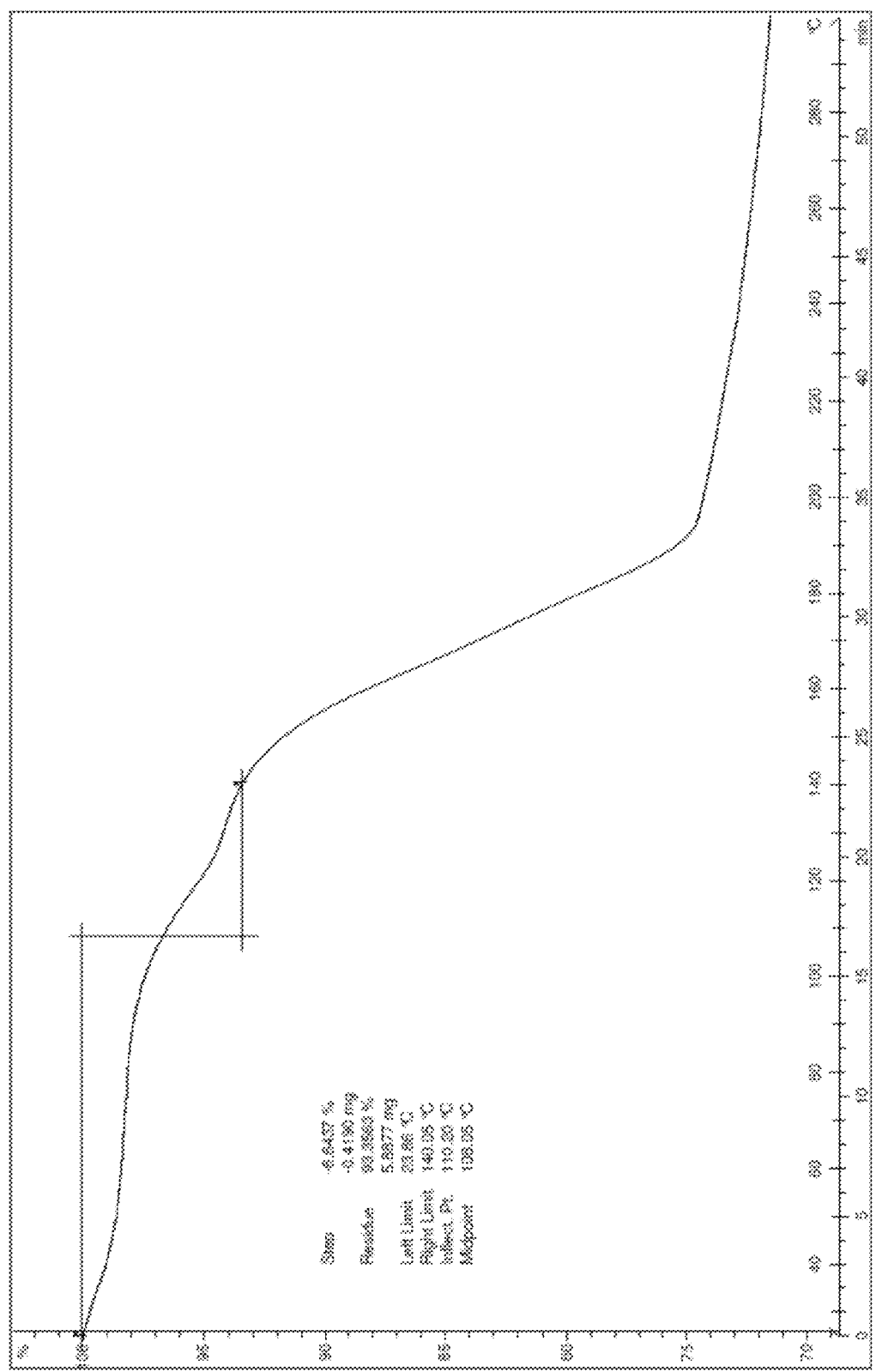
FIG. 35 is a TGA thermogram of fumaric acid salt of Compound I.

Compound I was dissolved in a solvent mixture at an elevated temperature, then Fumaric acid was added to the mixture. The resulting suspension was cooled, stirred, filtered, and washed to obtain a fumaric acid salt of Compound I as a white powder (104% yield). The resulting salt was characterized by $^1$H NMR (FIG. 33), XRPD (FIG. 31), and TGA (FIG. 35). The TGA showed fumaric acid salt of Compound I demonstrated up to 6.6% weight loss at 140° C.

Example 10. Preparation of a Citric Acid Salt of Compound I

Figure 40:
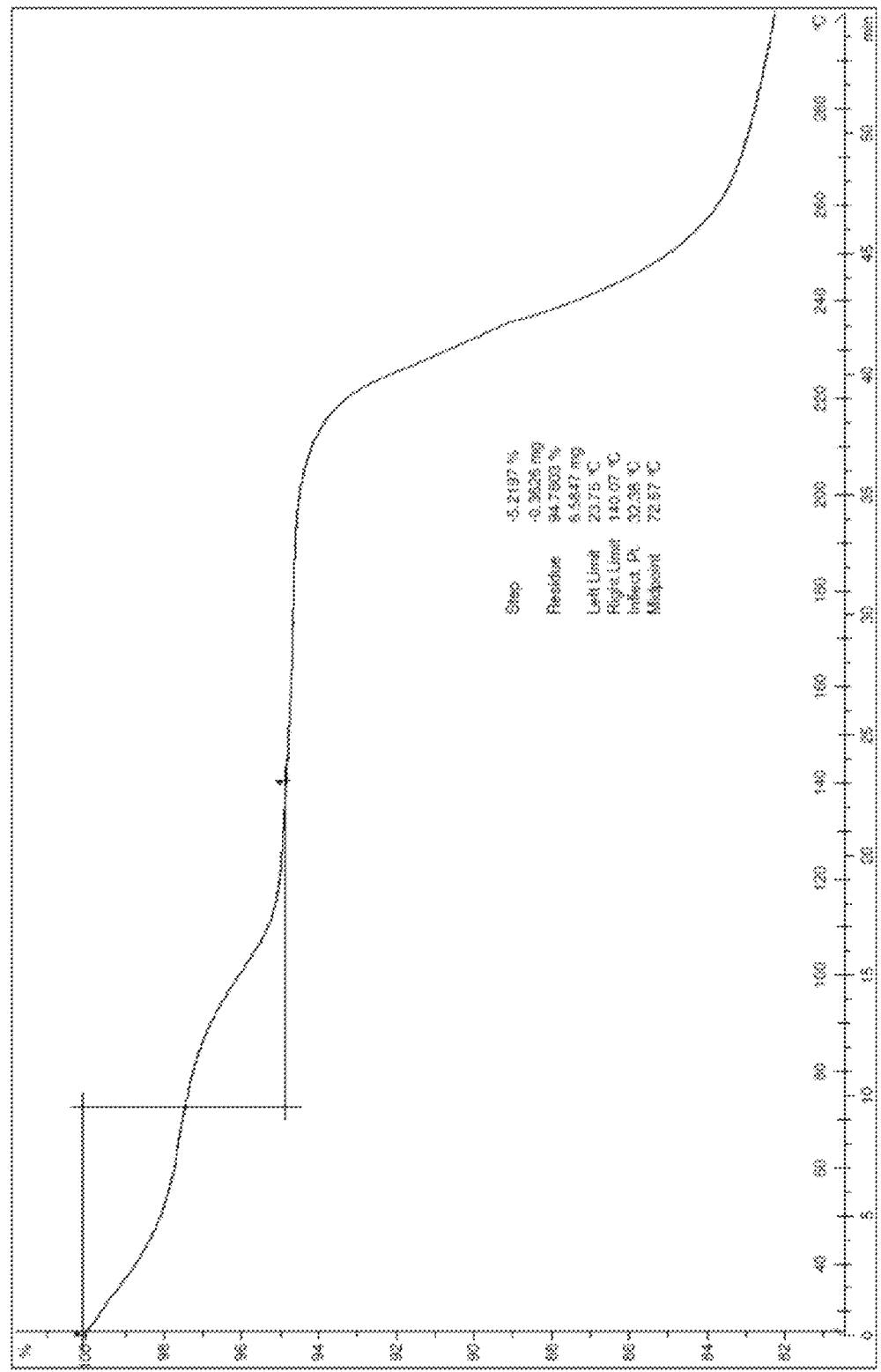
FIG. 40 is a TGA thermogram of citric acid salt of Compound I.

Compound I was dissolved in a solvent mixture at an elevated temperature, then Citric acid was added to the mixture. The resulting suspension was cooled, stirred, filtered, and washed to obtain a citric acid salt of Compound I as a white powder (93% yield). The resulting salt was characterized by $^1$H NMR (FIG. 38), XRPD (FIG. 36), and TGA (FIG. 40). The TGA showed citric acid salt of Compound I demonstrated up to 5.2% weight loss at 140° C.

Example 11. Preparation of an L-Malic Acid Salt of Compound I

Figure 45:
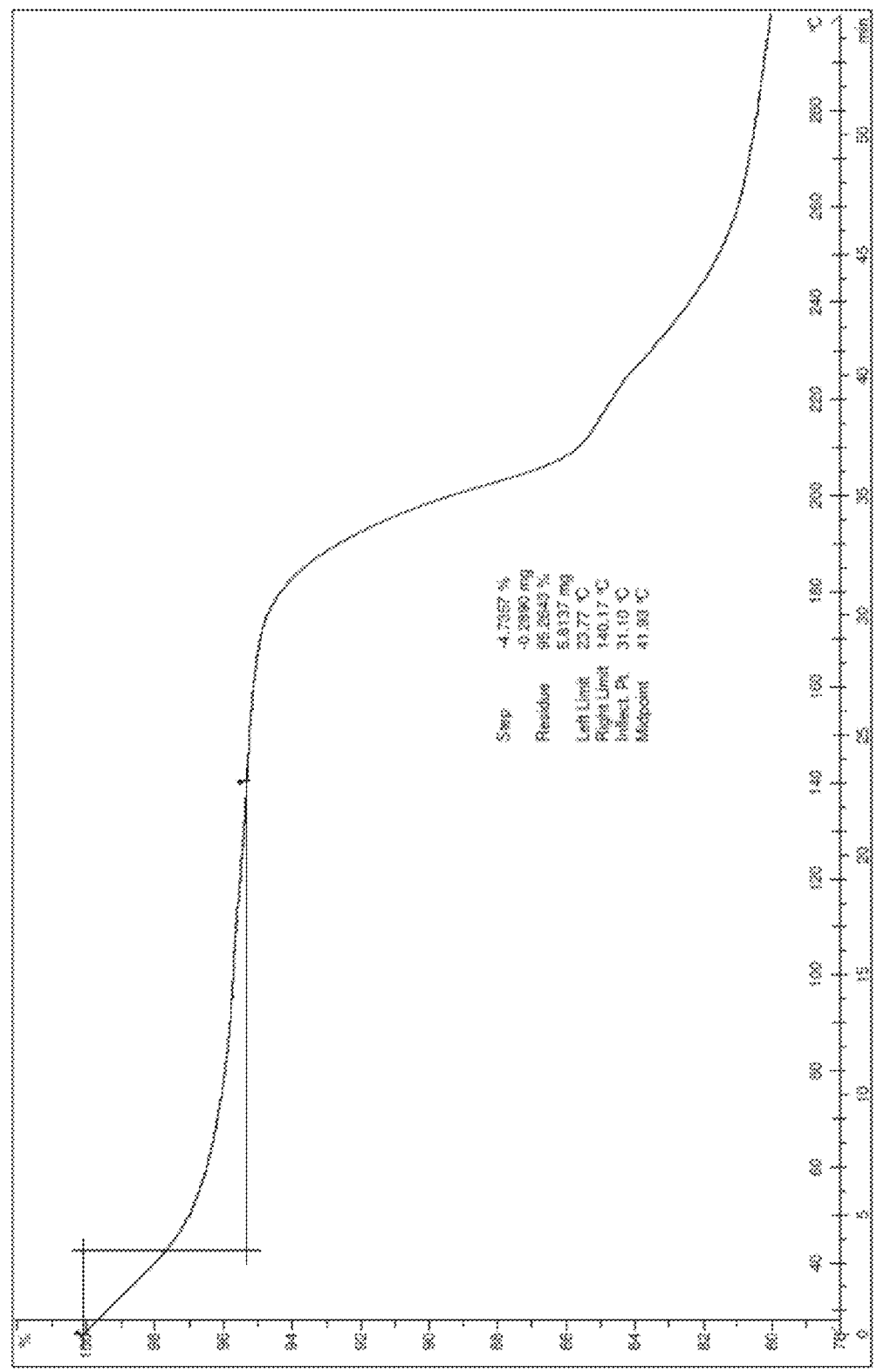
FIG. 45 is a TGA thermogram of L-malic acid salt of Compound I.

Compound I was dissolved in a solvent mixture at an elevated temperature, then L-Malic acid was added to the mixture. The resulting suspension was cooled, stirred, filtered, and washed to obtain an L-malic acid salt of Compound I as a white powder (59% yield). The resulting salt was characterized by $^1$H NMR (FIG. 43), XRPD (FIG. 41), and TGA (FIG. 45). The TGA showed citric acid salt of Compound I demonstrated up to 4.7% weight loss at 140° C.

Example 12. Solubility and Stability Test of Acid Salts of Compound I

Solubility of the HCl salt, maleic acid salt, fumaric acid salt, citric acid salt, and L-malic acid salt of Compound I were determined by suspending approximately 50 mg of each salt in 0.25 mL water (×2, added portion wise). The mixture was stirred at 42° C. for 3 days and each solution was analyzed by HPLC for concentration and purity. The solubility and purity of each salt after 3 day test are shown in Table 11 below.

TABLE 11

Solubility and Purity of Acid Addition Salts

| Acid Salt | Aqueous Solubility (Calculated) | Starting Purity % a/a (HPLC) | Purity % a/a after 3 days (HPLC) |
| --- | --- | --- | --- |
| HCl | >100 mg/mL | 98.78 | 88.62 |
| Maleic Acid | >200 mg/mL | 99.18 | 83.87 |
| Fumaric Acid | <100 mg/mL* | 98.46 | 82.38 |
| Citric Acid | >200 mg/mL | 98.62 | 95.21 |
| L-Malic Acid | <100 mg/mL | 98.07 | 95.08 |
| Free Base | <<100 mg/mL | NT | 99.58 |

*Sample dissolved during 3 day stability test;
NT = not tested

Stability of the acid salts were also tested by storing the salts (solid forms) at an elevated temperature of 45 and 80° C. The results of the stability test are shown in Table 12, below.

TABLE 12

Stability of Acid Addition Salts

| Acid Salt | Purity % a/a after 3 days at 80° C. (HPLC) | Purity % a/a after 3 days at 45° C. (HPLC) |
|---|---|---|
| HCl | 98.71 | 98.48 |
| Maleic Acid | 93.67 | 97.84 |
| Fumaric Acid | 89.36 | NT |
| Citric Acid | 95.17 | NT |
| L-Malic Acid | 95.67 | NT |
| Free Base | 99.67 | NT |

NT = not tested

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. An isolated crystalline form of a Compound I:

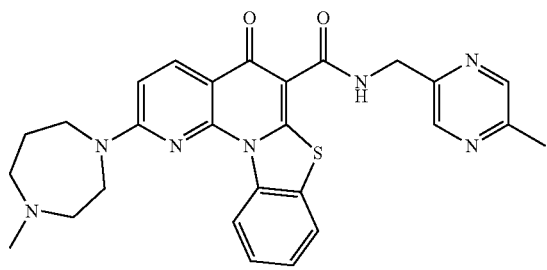

I or a pharmaceutically acceptable salt thereof; wherein the isolated crystalline form of Compound I is:
(a) a Polymorph A which is at least 90% pure;
(b) a Polymorph C which is at least 90% pure;
(c) a Polymorph E which is at least 90% pure;
(d) a Polymorph G which is at least 90% pure;
(e) a hydrochloric acid salt;
(f) a maleic acid salt;
(g) a fumaric acid salt;
(h) a citric acid salt; or
(i) an L-malic acid salt.

2. The isolated crystalline form of claim 1, which is
(a) a Polymorph A which is at least 90% pure;
(b) a Polymorph C which is at least 90% pure;
(c) a Polymorph E which is at least 90% pure; or
(d) a Polymorph G which is at least 90% pure;
of Compound I.

3. The isolated crystalline form of claim 2, which exhibits an X-ray powder diffraction pattern (XRDP) comprising peaks at 7.730±0.3, 22.050±0.3, and 24.550±0.3 degrees two-theta.

4. The isolated crystalline form of claim 3, wherein the XRPD patterns are obtained using a silicon low background sample holder of diameter 24 mm and pit size of 0.2 mm, a Cu Kα radiation of 1.5406 angstrom source operating at 15 kV, collection times of nominally 75 minutes, and an effective two theta range of 2 to 40° C. at a sampling width of 0.02° C.

5. The isolated crystalline form of claim 3, wherein the X-ray powder diffraction pattern further comprising peaks at 9.410±0.3 and 27.700±0.3 degrees two-theta.

6. The isolated crystalline form of claim 2, wherein the X-ray powder diffraction pattern further comprising peaks at 17.950±0.3 and 25.400±0.3 degrees two-theta.

7. The isolated crystalline form of claim 2, wherein the X-ray powder diffraction pattern further comprising one or more peaks selected from peaks at 11.230±0.3, 11.630±0.3, 16.900±0.3, 18.580±0.3, 23.300±0.3, and 26.700±0.3 degrees two-theta.

8. The isolated crystalline claim 2, which exhibits an X-ray powder diffraction pattern comprising three or more peaks selected from the group consisting of 7.730±0.3, 9.410±0.3, 11.230±0.3, 11.630±0.3, 16.900±0.3, 17.950±0.3, 18.580±0.3, 22.050±0.3, 23.300±0.3, 24.550±0.3, 25.400±0.3, 26.700±0.3 and 27.700±0.3 degrees two-theta.

9. The isolated crystalline form of claim 2, which exhibits a Differential Scanning calorimetry (DSC) thermogram having a peak characteristic value at 215.41±2.0° C.

10. The isolated crystalline form of claim 2, which has a purity of 95% or higher.

11. The isolated crystalline form of claim 10, which exhibits purity of 97% or higher.

12. The isolated crystalline form of claim 11, which exhibits purity of 99% or 99.5% or higher.

13. The isolated crystalline form of claim 2, which exhibits an X-ray powder diffraction pattern comprising peaks at 5.720±0.3 degrees two-theta.

14. The isolated crystalline form of claim 13, which exhibits a Differential Scanning calorimetry (DSC) thermogram having a peak characteristic value at 246.47±2.0° C.

15. The isolated crystalline form of claim 13, which is a Polymorph C which is at least 90% pure.

16. The isolated crystalline form of claim 13, which has a purity of 95% or higher.

17. The isolated crystalline form of claim 16, which exhibits purity of 97% or higher.

18. The isolated crystalline form of claim 17, which exhibits purity of 99% or 99.5% or higher.

19. The isolated crystalline form of claim 2, which exhibits an X-ray powder diffraction pattern comprising peaks at 5.680±0.2 degrees two-theta.

20. The isolated crystalline form of claim 19, wherein the X-ray powder diffraction pattern further comprising peaks at 12.200±0.2, 12.600±0.3, 25.360±0.3 and 27.560±0.3 degrees two-theta.

21. The isolated crystalline form of claim 19, which exhibits an X-ray powder diffraction pattern comprising two or more peaks selected from the group consisting of 5.680±0.2, 12.200±0.2, 12.600±0.3, 25.360±0.3 and 27.560±0.3.

22. The isolated crystalline form of claim 19, which exhibits a Differential Scanning calorimetry (DSC) thermogram having a peak characteristic value at 231.99±2.0° C.

23. The isolated crystalline form of claim 19, which has a purity of 95% or higher.

24. The isolated crystalline form of claim 23, which exhibits purity of 97% or higher.

25. The isolated crystalline form of claim 24, which exhibits purity of 99% or 99.5% or higher.

26. The isolated crystalline form of claim 2, which exhibits an X-ray powder diffraction pattern comprising peaks at 5.000±0.3 and 6.060±0.4 degrees two-theta.

27. The isolated crystalline form of claim 26, which exhibits a Differential Scanning calorimetry (DSC) thermogram having a peak characteristic value at 222.11±2.0° C.

28. The isolated crystalline form of claim 26, which is a Polymorph G which is at least 90% pure.

29. The isolated crystalline form of claim 26, which has a purity of 95% or higher.

30. The isolated crystalline form of claim 29, which exhibits purity of 97% or higher.

31. The isolated crystalline form of claim 29, which exhibits purity of 99% or 99.5% or higher.

32. The isolated crystalline form of claim 1, wherein the salt is selected from the group consisting of: hydrochloric acid salt, maleic acid salt, fumaric acid salt, citric acid salt, malic acid salt, acetic acid salt, sulfuric acid salt, phosphoric acid salt, L-(+)-tartaric acid salt, D-glucuronic acid salt, benzoic acid salt, succinic acid salt, ethane sulfonic acid salt, methane sulfonic acid salt, p-toluene sulfonic acid salt, malonic acid salt, benzene sulfonic acid salt, and 1-hydroxy-2-naphthoic acid salt.

33. The isolated crystalline form of claim 1, wherein the salt is selected from the group consisting of: hydrochloric acid salt, maleic acid salt, fumaric acid salt, citric acid salt, and L-malic acid salt.

34. The isolated crystalline form of claim 33, which is an isolated crystalline form of maleic acid salt of Compound I.

35. The isolated crystalline form of claim 34, which exhibits an X-ray powder diffraction pattern (XRDP) comprising peaks at 7.400±0.3, 18.440±0.5, and 26.500±0.4 degrees two-theta.

36. The isolated crystalline form of claim 35, wherein the X-ray powder diffraction pattern further comprising one or more peaks at 22.320±0.4, 23.920±0.3, 24.300±0.4, and 25.240±0.7 degrees two-theta.

37. The isolated crystalline form of claim 34, wherein the X-ray powder diffraction pattern further comprising one or more peaks at 5.040±0.3, 15.080±0.3, 15.880±0.4, 20.860±0.4, and 28.540±0.3 degrees two-theta.

38. The isolated crystalline form of claim 34, which exhibits a Differential Scanning calorimetry (DSC) thermogram having a peak characteristic value at 217.32±2.0° C.

39. The isolated crystalline form of claim 33, which is an isolated crystalline form of fumaric acid salt of Compound I.

40. The isolated crystalline form of claim 39, which exhibits an X-ray powder diffraction pattern (XRDP) comprising peaks at 6.360±0.3 and 24.800±0.3 degrees two-theta.

41. The isolated crystalline form of claim 40, wherein the X-ray powder diffraction pattern further comprising one or more peaks at 19.660±0.3, 20.420±0.3, and 26.860±0.3 degrees two-theta.

42. The isolated crystalline form of claim 39, wherein the X-ray powder diffraction pattern further comprising one or more peaks at 12.680±0.3, 17.020±0.2, 25.180±0.2, and 28.280±0.3 degrees two-theta.

43. The isolated crystalline form of claim 39, which exhibits a Differential Scanning calorimetry (DSC) thermogram having a peak characteristic value at 222.40±2.0° C.

44. The isolated crystalline form of claim 33, which is an isolated crystalline form of citric acid salt of Compound I.

45. The isolated crystalline form of claim 44, which exhibits an X-ray powder diffraction pattern (XRDP) comprising peaks at 4.900±0.3, 25.380±0.3, and 27.500±0.4 degrees two-theta.

46. The isolated crystalline form of claim 45, wherein the X-ray powder diffraction pattern further comprising one or more peaks at 15.360±0.3, 18.100±0.3, 19.300±0.3, and 26.140±0.4 degrees two-theta.

47. The isolated crystalline form of claim 44, wherein the X-ray powder diffraction pattern further comprising one or more peaks at 17.400±0.3, 18.680±0.4, 24.040±0.4, and 26.740±0.3 degrees two-theta.

48. The isolated crystalline form of claim 44, which exhibits a Differential Scanning calorimetry (DSC) thermogram having a peak characteristic value at 196.86±2.0° C.

49. The isolated crystalline form of claim 33, which is an isolated crystalline form of L-malic acid salt of Compound I.

50. The isolated crystalline form of claim 49, which exhibits an X-ray powder diffraction pattern (XRDP) comprising peaks at 6.580±0.2, 6.780±0.3, and 25.560±0.4 degrees two-theta.

51. The isolated crystalline form of claim 50, wherein the X-ray powder diffraction pattern further comprising one or more peaks at 19.560±0.4, 23.660±0.4, 26.060±0.7, and 26.960±0.7 degrees two-theta.

52. The isolated crystalline form of claim 49, wherein the X-ray powder diffraction pattern further comprising one or more peaks at 8.800±0.3, 11.800±0.3, 18.600±0.3, 24.460±0.5, and 25.080±0.3 degrees two-theta.

53. The isolated crystalline form of claim 49, which exhibits a Differential Scanning calorimetry (DSC) thermogram having a peak characteristic value at 209.67±2.0° C.

54. The isolated crystalline form of claim 33, which is an isolated crystalline form of HCl salt of Compound I.

55. The isolated crystalline form of claim 54, which exhibits an X-ray powder diffraction pattern (XRDP) comprising peaks at 4.660±0.3 and 24.540±0.3 degrees two-theta.

56. The isolated crystalline form of claim 55, wherein the X-ray powder diffraction pattern further comprising one or more peaks at 19.260±0.4, 20.160±0.4, 24.920±0.3, and 26.360±0.35 degrees two-theta.

57. The isolated crystalline form of claim 54, wherein the X-ray powder diffraction pattern further comprising one or more peaks at 13.980±0.4, 14.540±0.3, 25.380±0.3, and 28.940±0.3 degrees two-theta.

58. The isolated crystalline form of claim 54, which exhibits a Differential Scanning calorimetry (DSC) thermogram having a peak characteristic value at 266.27±2.0° C.

59. A composition comprising an isolated crystalline form of claim 1.

60. The composition of claim 59, wherein the composition comprises at least one pharmaceutically acceptable carrier.

61. A method for stabilizing G-quadruplexes (G4s) in a subject, the method comprising administering to the subject a therapeutically effective amount of an isolated crystalline form of claim 1.

62. A method for modulating p53 activity in a subject, the method comprising administering to the subject a therapeutically effective amount of an isolated crystalline form of claim 1.

63. A method for treating or ameliorating cell proliferation disorder in a subject, said method comprising administering to a subject in need thereof a therapeutically effective amount of an isolated crystalline form of claim 1, wherein the cell proliferation disorder is cancer selected from one or more of the group consisting of heme cancer, colorectum cancer, breast cancer, lung cancer, liver cancer, ovarian cancer, cervical cancer, Ewing's sarcoma, pancreatic cancer, cancer of the lymph nodes, colon cancer, prostate cancer, brain cancer, cancer of the head and neck, skin cancer, kidney cancer, and cancer of the heart.

64. The method of claim 63, wherein said heme cancer is selected from the group consisting of: leukemia, lymphoma, myeloma, and multiple myeloma.

65. The method of claim 63, wherein the cancer is homologous recombination (HR) dependent double strand break (DSB) repair deficient cancer or non-homologous end joining (NHEJ) DSB repair deficient cancer.

66. The method of claim 63, wherein the cancer comprises cancer cells harboring defects in breast cancer 1 (BRCA1), breast cancer 2 (BRCA2), and/or other members of the homologous recombination pathway.

67. The method of claim 66, wherein the cancer cells are deficient in BRCA1 and/or BRCA2.

68. The method of claim 67, wherein the cancer cells are homozygous for a mutation in BRCA1 and/or BRCA2.

69. The method of claim 67, wherein the cancer cells are heterozygous for a mutation in BRCA1 and/or BRCA2.

70. The method of claim 63, wherein the method further comprises co-administering one or more additional therapeutic agents and/or radio therapy.

71. The method of claim 70, wherein said one or more additional therapeutic agent is an anticancer agent or immunotherapeutic agent.

72. A method for reducing or inhibiting cell proliferation, said method comprising contacting cells with a therapeutically effective amount of an isolated crystalline form of claim 1, wherein the cells are one or more of cancer cells selected from the group consisting of heme cancer cells, colorectum cancer cells, breast cancer cells, lung cancer cells, liver cancer cells, pancreatic cancer cells, cells of cancer of the lymph nodes, colon cancer cells, prostate cancer cells, brain cancer cells, cells of cancer of the head and neck, skin cancer cells, ovarian cancer cells, cervical cancer cells, Ewing's sarcoma cells, kidney cancer cells, and cells of cancer of the heart.

73. The method of claim 72, wherein the cells are in a cancer cell line or in a cancer in a subject.

74. The method of claim 73, wherein the cancer cells harboring defects in homologous recombination (HR) dependent double strand break (DSB) repair or non-homologous end joining (NHEJ) DSB repair.

75. The method of claim 73, wherein the cancer comprise cancer cells harboring defects in breast cancer 1 (BRCA1), breast cancer 2 (BRCA2), and/or other members of the homologous recombination pathway.

76. The method of claim 75, wherein the cancer cells are deficient in BRCA1 and/or BRCA2.

77. The method of claim 76, wherein the cancer cells are homozygous for a mutation in BRCA1 and/or BRCA2.

78. The method of claim 76, wherein the cancer cells are heterozygous for a mutation in BRCA1 and/or BRCA2.

79. The method of claim 72, wherein said heme cancer cell is selected from the group consisting of: leukemia, lymphoma, myeloma, and multiple myeloma.

80. The isolated crystalline form of claim 1, which is a Polymorph A which is at least 90% pure.

81. The isolated crystalline form of claim 1, which is a Polymorph E which is at least 90% pure.

\* \* \* \* \*